(12) United States Patent
Kim et al.

(10) Patent No.: US 11,335,859 B2
(45) Date of Patent: May 17, 2022

(54) COMPOUND, COATING COMPOSITION COMPRISING SAME, AND ORGANIC LIGHT EMITTING ELEMENT COMPRISING SAME

(71) Applicant: LG Chem, Ltd., Seoul (KR)

(72) Inventors: Yongwook Kim, Daejeon (KR); Jaechol Lee, Daejeon (KR); Jaesoon Bae, Daejeon (KR); Daeho Kim, Daejeon (KR); Seokhee Yoon, Daejeon (KR); Sungkyoung Kang, Daejeon (KR); Kwanghyun Kim, Daejeon (KR)

(73) Assignee: LG Chem, Ltd.

( * ) Notice: Subject to any disclaimer, the term of this patent is extended or adjusted under 35 U.S.C. 154(b) by 357 days.

(21) Appl. No.: 16/486,350

(22) PCT Filed: Jun. 20, 2018

(86) PCT No.: PCT/KR2018/006966
§ 371 (c)(1),
(2) Date: Aug. 15, 2019

(87) PCT Pub. No.: WO2018/236146
PCT Pub. Date: Dec. 27, 2018

(65) Prior Publication Data
US 2019/0386219 A1    Dec. 19, 2019

(30) Foreign Application Priority Data

Jun. 20, 2017 (KR) .................. 10-2017-0077893
Jun. 19, 2018 (KR) .................. 10-2018-0070242

(51) Int. Cl.
| | | |
|---|---|---|
| *H01L 51/00* | (2006.01) | |
| *C07D 307/91* | (2006.01) | |
| *C07F 7/08* | (2006.01) | |
| *C09D 5/22* | (2006.01) | |
| *C09D 5/24* | (2006.01) | |

(Continued)

(52) U.S. Cl.
CPC .......... *H01L 51/006* (2013.01); *C07D 307/91* (2013.01); *C07F 7/0812* (2013.01);
(Continued)

(58) Field of Classification Search
None
See application file for complete search history.

(56) References Cited

U.S. PATENT DOCUMENTS 8,173,272 B2 * 5/2012 Jang .................. C07F 7/30
428/690
8,502,201 B2 * 8/2013 Nagao .............. H01L 51/0073
257/40

(Continued)

FOREIGN PATENT DOCUMENTS

| JP | H08179526 A | 7/1996 |
|---|---|---|
| JP | 2004204238 A | 7/2004 |

(Continued)

OTHER PUBLICATIONS

International Search Report for Application No. PCT/KR2018/006966 dated Oct. 4, 2018, 2 pages.

*Primary Examiner* — Robert S Loewe
(74) *Attorney, Agent, or Firm* — Lerner, David, Littenberg, Krumholz & Mentlik, LLP

(57) ABSTRACT

The present disclosure relates to a compound of Chemical Formula 1, a coating composition including the same, and an organic light emitting device including the same.

20 Claims, 7 Drawing Sheets

(51) Int. Cl.
  *C09K 11/06* (2006.01)
  *H01L 51/50* (2006.01)
(52) U.S. Cl.
  CPC ............... *C09D 5/22* (2013.01); *C09D 5/24* (2013.01); *C09K 11/06* (2013.01); *H01L 51/0061* (2013.01); *H01L 51/0094* (2013.01); *C09K 2211/1018* (2013.01); *H01L 51/0054* (2013.01); *H01L 51/0058* (2013.01); *H01L 51/0073* (2013.01); *H01L 51/5012* (2013.01); *H01L 51/5016* (2013.01); *H01L 51/5056* (2013.01); *H01L 51/5088* (2013.01)

(56) References Cited

U.S. PATENT DOCUMENTS

| | | | |
|---|---|---|---|
| 9,876,176 B2* | 1/2018 | Kim | H01L 51/0067 |
| 2004/0137270 A1 | 7/2004 | Seo et al. | |
| 2009/0001874 A1* | 1/2009 | Yen | H01L 51/006 |
| | | | 313/504 |
| 2009/0058270 A1 | 3/2009 | Ito et al. | |
| 2010/0109517 A1* | 5/2010 | Fukushima | H01L 51/0035 |
| | | | 313/504 |
| 2010/0187504 A1 | 7/2010 | Jang et al. | |
| 2017/0229648 A1 | 8/2017 | Kawakami et al. | |
| 2020/0091435 A1* | 3/2020 | Masuda | H01L 51/0061 |

FOREIGN PATENT DOCUMENTS

| | | |
|---|---|---|
| JP | 2011173973 A | 9/2011 |
| JP | 2013155294 A | 8/2013 |
| KR | 20080052594 A | 6/2008 |
| KR | 20080096440 A | 10/2008 |
| KR | 20140096227 A | 8/2014 |
| KR | 20150052989 A | 5/2015 |
| KR | 20160034937 A | 3/2016 |

* cited by examiner

[FIG. 1]
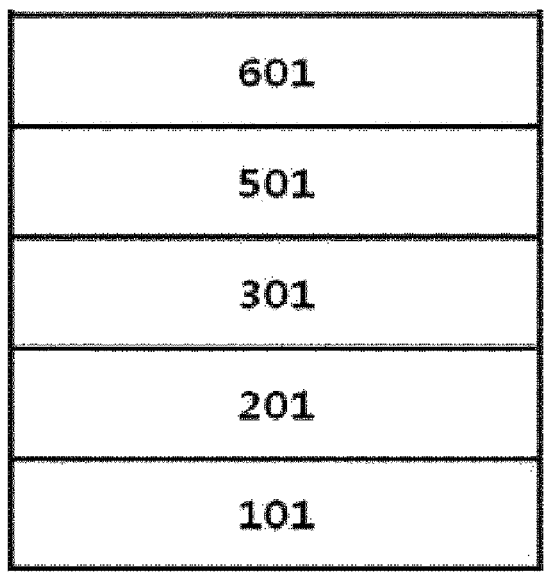
[FIG. 2]
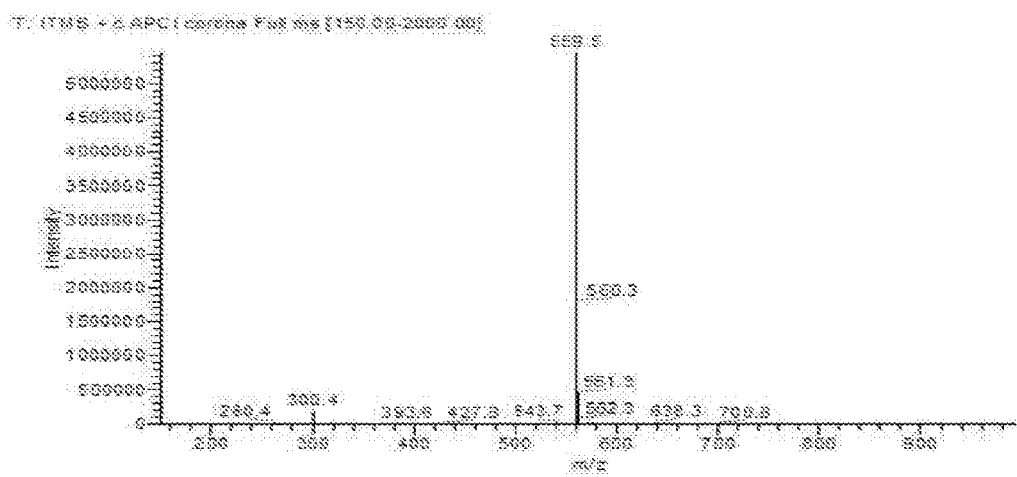

[FIG. 3]
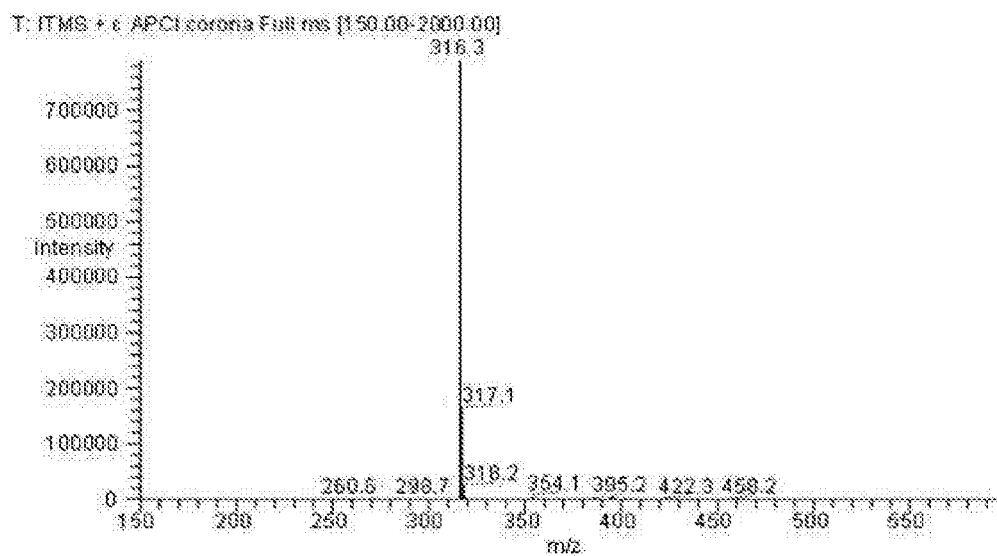
[FIG. 4]
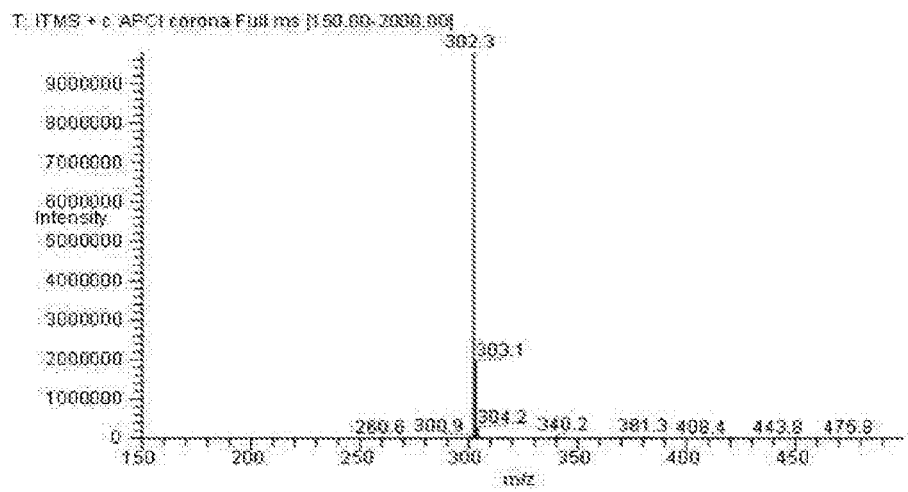

[FIG. 5]
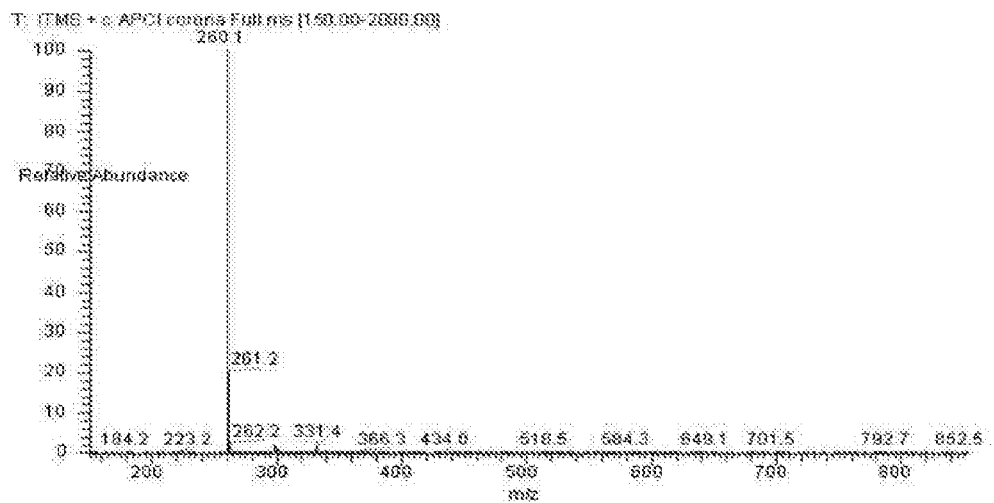
[FIG. 6]
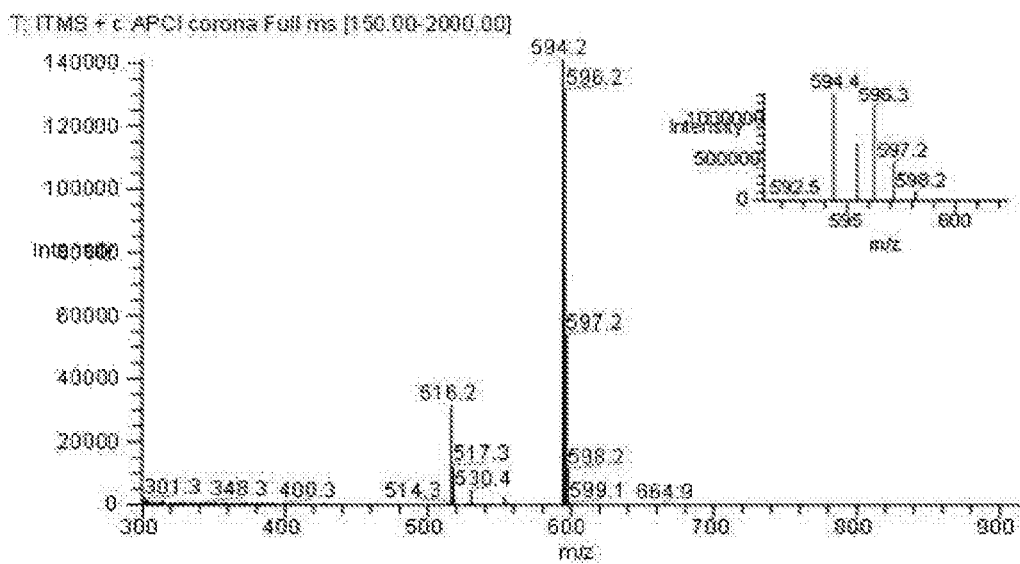

[FIG. 7]
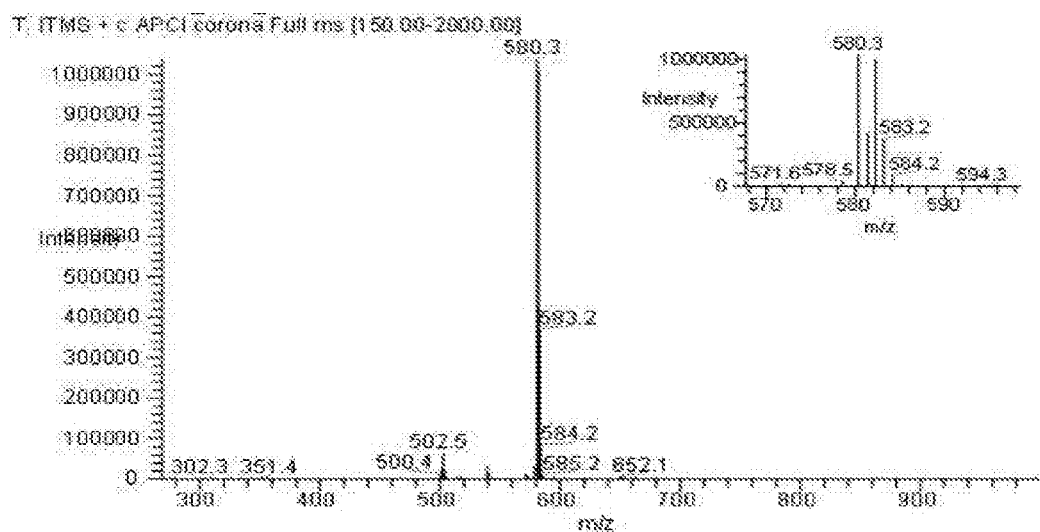
[FIG. 8]
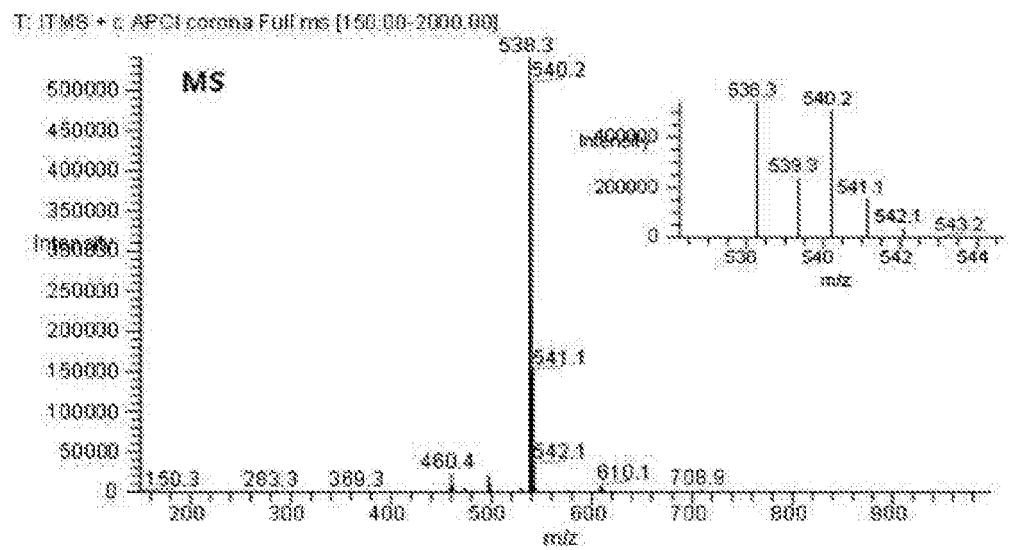

[FIG. 9]
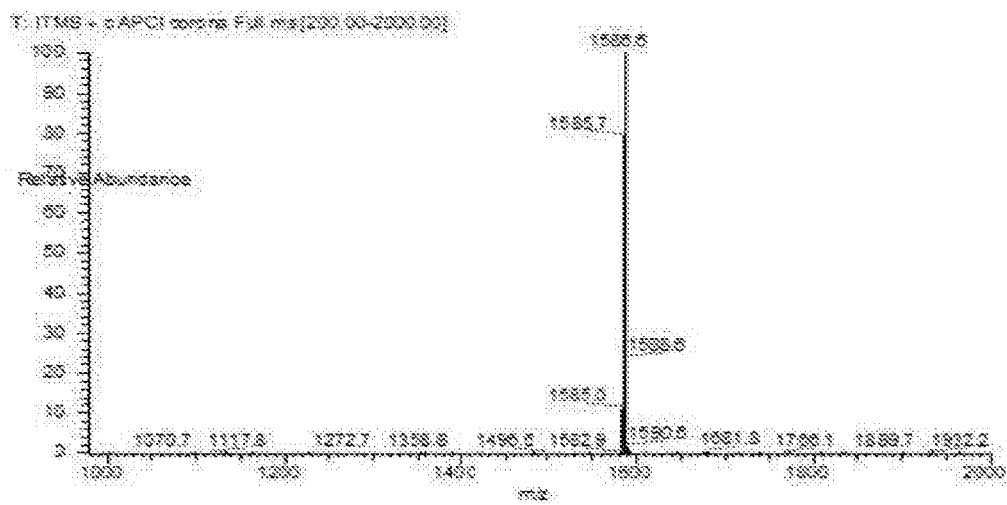
[FIG. 10]
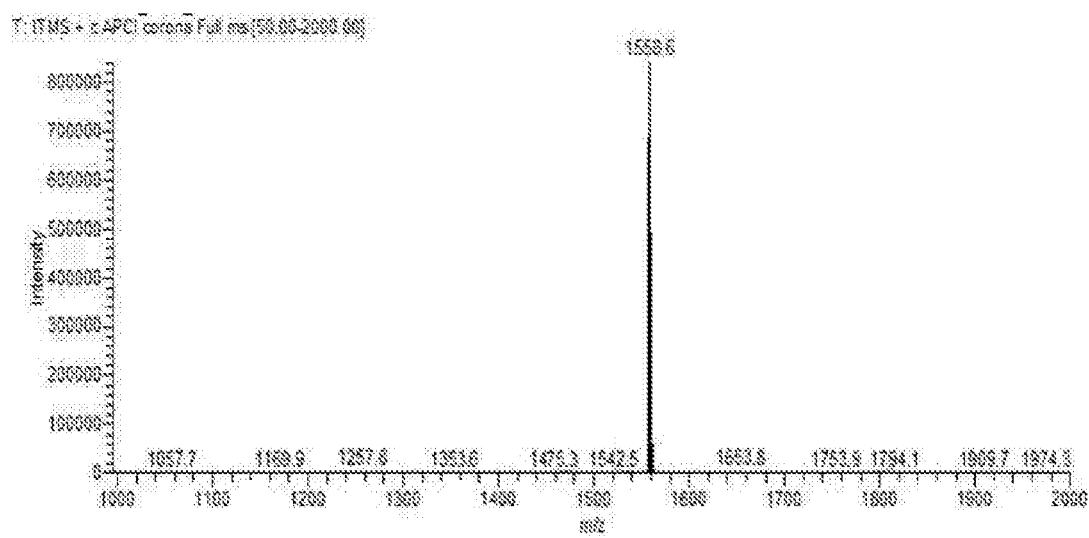

【FIG. 11】
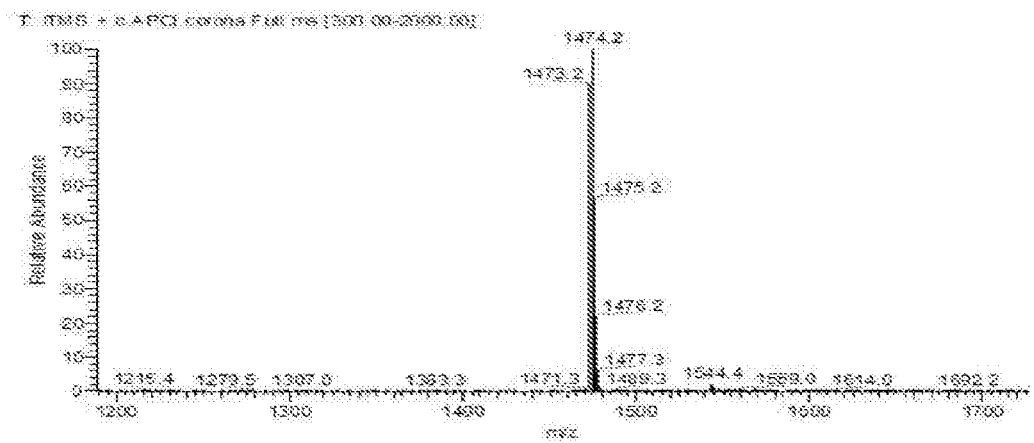
【FIG. 12】
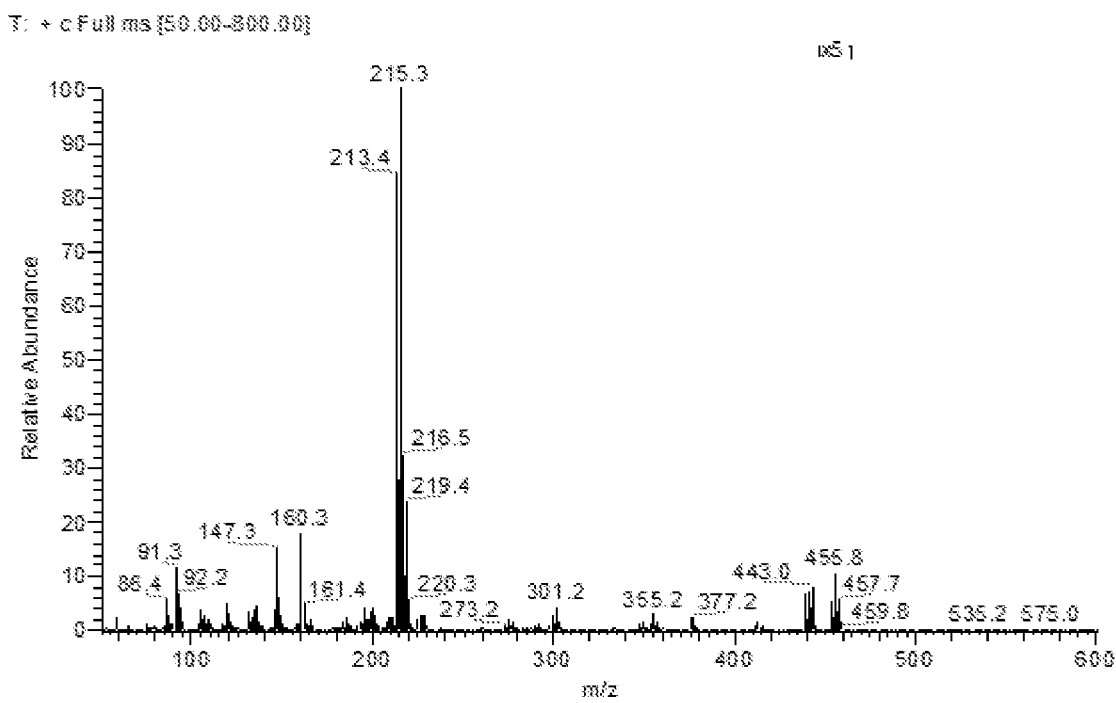

【FIG. 13】
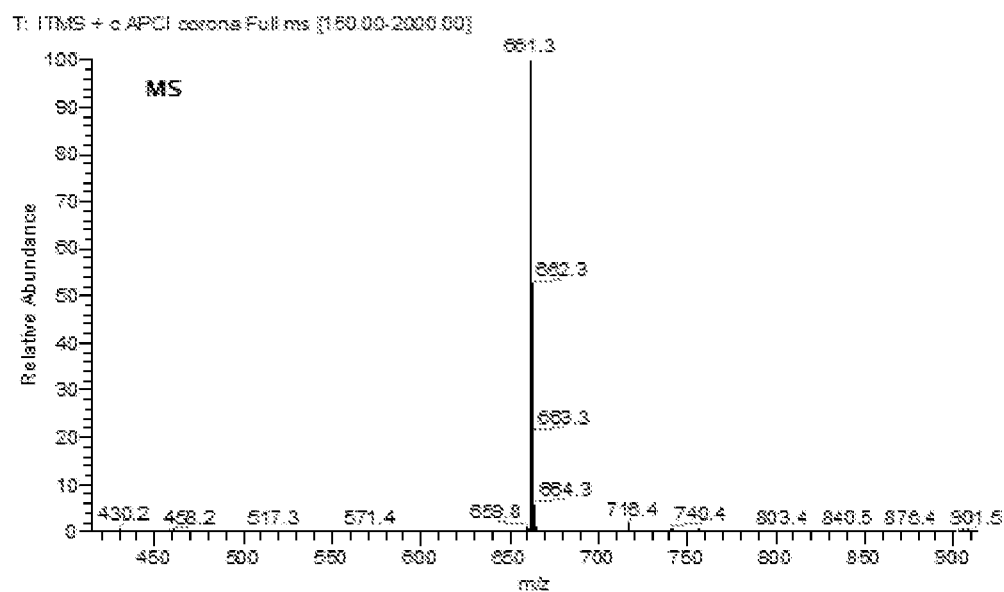
【FIG. 14】
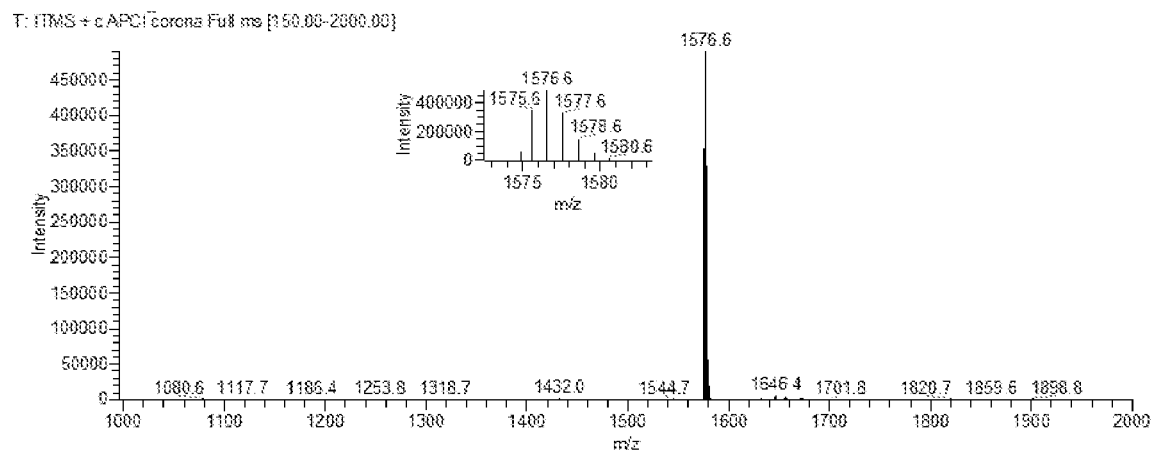

COMPOUND, COATING COMPOSITION COMPRISING SAME, AND ORGANIC LIGHT EMITTING ELEMENT COMPRISING SAME

CROSS-REFERENCE TO RELATED APPLICATIONS

The present application is a national phase entry under 35 U.S.C. § 371 of International Application No. PCT/KR2018/006966 filed Jun. 20, 2018, which claims priority from Korean Patent Application No. 10-2017-0077893 filed Jun. 20, 2017 and Korean Patent Application No. 10-2018-0070242 filed Jun. 19, 2018, all of which are incorporated herein by reference.

TECHNICAL FIELD

The present specification relates to a compound, a coating composition including the compound, and an organic light emitting device including the same.

BACKGROUND ART

An organic light emission phenomenon is one of examples converting a current to visible light by an internal process of specific organic molecules. A principle of an organic light emission phenomenon is as follows. When an organic material layer is placed between an anode and a cathode and a current is applied between the two electrodes, electrons and holes are injected to the organic material layer from the cathode and the anode, respectively. The holes and the electrons injected to the organic material layer recombine to form excitons, and light emits when these excitons fall back to the ground state. An organic light emitting device using such a principle may be generally formed with a cathode, an anode, and an organic material layer placed therebetween, for example, an organic material layer including a hole injection layer, a hole transfer layer, a light emitting layer and an electron transfer layer.

Materials used in an organic light emitting device are mostly pure organic materials or complex compounds in which organic materials and metals form complexes, and may be divided into hole injection materials, hole transfer materials, light emitting materials, electron transfer materials, electron injection materials and the like depending on the application. Herein, as the hole injection material or the hole transfer material, organic materials having a p-type property, that is, organic materials readily oxidized and having an electrochemically stable state when oxidized, are generally used. Meanwhile, as the electron injection material or the electron transfer material, organic materials having an n-type property, that is, organic materials readily reduced and having an electrochemically stable state when reduced, are generally used. As the light emitting layer material, materials having both a p-type property and an n-type property, that is, materials having a stable form in both oxidized and reduced states, are preferred, and materials having high light emission efficiency converting, when excitons are formed, the excitons to light are preferred.

In addition to the properties described above, it is preferred that materials used in an organic light emitting device additionally have properties as follows.

First, materials used in an organic light emitting device preferably have excellent thermal stability. This is due to joule heat produced by charge migration in the organic light emitting device. NPB normally used as a hole transfer layer material currently has a glass transition temperature of 100° C. or lower, and has a problem in that it is difficult to use in organic light emitting devices requiring a high current.

Second, in order to obtain a highly efficient organic light emitting device capable of low voltage driving, holes or electrons injected into the organic light emitting device need to be smoothly transferred to a light emitting layer, and at the same time, the injected holes and electrons need to be kept from escaping out of the light emitting layer. For this, materials used in the organic light emitting device need to have a proper band gap and a HOMO or LUMO energy level. PEDOT:PSS currently used as a hole transfer material in an organic light emitting device manufactured using a solution coating method has a lower LUMO energy level compared to a LUMO energy level of organic materials used as a light emitting layer material, and therefore, has a problem in manufacturing an organic light emitting device with high efficiency and long lifetime.

In addition thereto, materials used in an organic light emitting device need to have excellent chemical stability, charge mobility, and interface property with electrodes or adjacent layers. In other words, materials used in an organic light emitting device need to undergo less material deformation caused by moisture or oxygen. In addition, by having proper hole or electron mobility, the materials need to maximize exciton formation through balancing hole and electron density in a light emitting layer of the organic light emitting device. For device stability, the materials also need to improve an interface with electrodes including metals or metal oxides.

Accordingly, development of organic materials fulfilling such requirements has been required in the art.

DISCLOSURE

Technical Problem

The present specification is directed to providing a compound, a coating composition including the same, and an organic light emitting device including the same.

Technical Solution

One embodiment of the present specification provides a compound represented by the following Chemical Formula 1.

[Chemical Formula 1]

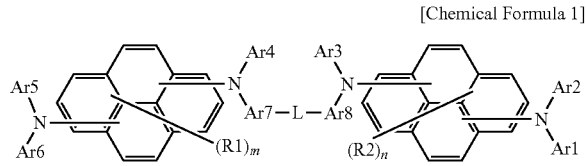

In Chemical Formula 1,

Ar1 to Ar6 are the same as or different from each other, and each independently a substituted or unsubstituted aryl group; or a substituted or unsubstituted heterocyclic group, Ar7 and Ar8 are the same as or different from each other, and each independently a substituted or unsubstituted arylene group; or a substituted or unsubstituted divalent heterocyclic group, R1 and R2 are the same as or different from each other, and each independently hydrogen; or a substituted or unsubstituted alkyl group, m and n are the same as or different from each other, and each independently an integer of 0 to 8, and when m is 2 or greater, R1s are the same as or different from each other, and when n is 2 or greater, R2s are the same as or different from each other, and L is a substituted or unsubstituted alkylene group; a substituted or unsubstituted cycloalkylene group; or selected from among the following structural formulae,

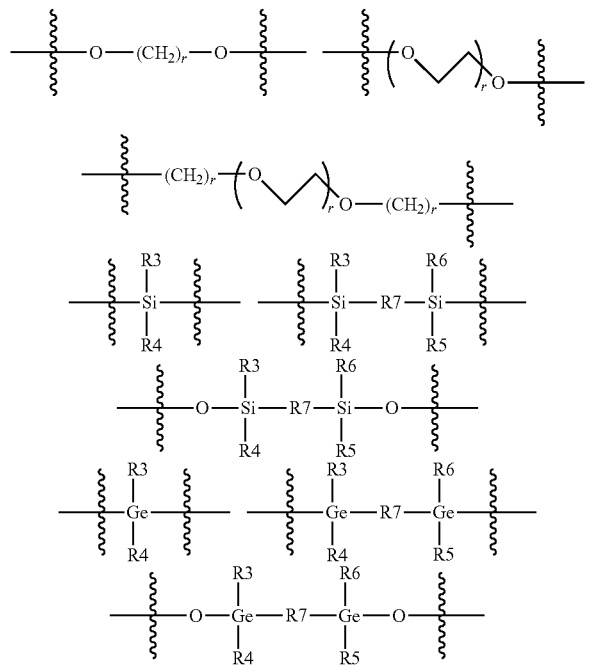

in the structural formulae, r is an integer of 1 to 20,

R3 to R6 are the same as or different from each other, and each independently a substituted or unsubstituted alkyl group, or a substituted or unsubstituted aryl group, R7 is a direct bond; a substituted or unsubstituted alkylene group; a substituted or unsubstituted cycloalkylene group; or a substituted or unsubstituted arylene group, and

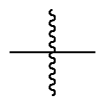

means a site bonding to Ar7 and Ar8.

Another embodiment of the present specification provides a coating composition including the compound described above.

Another embodiment of the present specification provides an organic light emitting device including a first electrode; a second electrode provided opposite to the first electrode; and one or more organic material layers provided between the first electrode and the second electrode, wherein one or more layers of the organic material layers include the coating composition described above.

Advantageous Effects

A compound according to the present disclosure can be used as a material of an organic material layer of an organic light emitting device. The compound can be prepared using a solution process, and therefore, large area devices can be manufactured. Particularly, a light emitting layer of an organic light emitting device can be formed using a solution process by using the compound as a material capable of increasing solubility and linking a light emitting material thereto, which can greatly improve processability as a result.

A compound according to one embodiment of the present specification can be used as a material of an organic material layer of an organic light emitting device, and is capable of providing low driving voltage, high light emission efficiency and long lifetime properties.

DESCRIPTION OF DRAWINGS

FIG. 1 illustrates an example of an organic light emitting device according to one embodiment of the present specification.

FIG. 2 shows Mass data of Compound 3 according to Preparation Example 1 of the present specification.

FIG. 3 shows Mass data of Compound 5 according to Preparation Example 2 of the present specification.

FIG. 4 shows Mass data of Compound 7 according to Preparation Example 3 of the present specification.

FIG. 5 shows Mass data of Compound 9 according to Preparation Example 4 of the present specification.

FIG. 6 shows Mass data of Compound 11 according to Preparation Example 5 of the present specification.

FIG. 7 shows Mass data of Compound 12 according to Preparation Example 6 of the present specification.

FIG. 8 shows Mass data of Compound 13 according to Preparation Example 7 of the present specification.

FIG. 9 shows Mass data of Compound 14 according to Preparation Example 1-1 of the present specification.

FIG. 10 shows Mass data of Compound 15 according to Preparation Example 1-2 of the present specification.

FIG. 11 shows Mass data of Compound 16 according to Preparation Example 1-3 of the present specification.

FIG. 12 shows Mass data of Compound 24 according to Preparation Example 2-1 of the present specification.

FIG. 13 shows Mass data of Compound 27 according to Preparation Example 2-1 of the present specification.

FIG. 14 shows Mass data of Compound 28 according to Preparation Example 2-1 of the present specification.

REFERENCE NUMERAL

101: Substrate
201: Anode
301: Hole Injection and Transfer Layer
501: Light Emitting Layer
601: Cathode

MODE FOR DISCLOSURE

Hereinafter, the present specification will be described in more detail.

In the present specification, a description of a certain member being placed "on" another member includes not only a case of the one member adjoining the another member but a case of still another member being present between the two members.

In the present specification, a description of a certain part "including" certain constituents means capable of further including other constituents, and does not exclude other constituents unless particularly stated on the contrary.

Throughout the specification of the present application, the term "a combination thereof" included in a Markush-type expression means a mixture or a combination of one or more selected from the group consisting of constituents described in the Markush-type expression, and means including one or more selected from the group consisting of the constituents.

One embodiment of the present specification provides a compound represented by the following Chemical Formula 1.

[Chemical Formula 1]

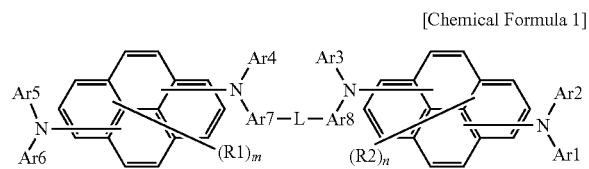

In Chemical Formula 1,

Ar1 to Ar6 are the same as or different from each other, and each independently a substituted or unsubstituted aryl group; or a substituted or unsubstituted heterocyclic group, Ar7 and Ar8 are the same as or different from each other, and each independently a substituted or unsubstituted arylene group; or a substituted or unsubstituted divalent heterocyclic group, R1 and R2 are the same as or different from each other, and each independently hydrogen; or a substituted or unsubstituted alkyl group, m and n are the same as or different from each other, and each independently an integer of 0 to 8, and when m is 2 or greater, R1s are the same as or different from each other, and when n is 2 or greater, R2s are the same as or different from each other, and L is a substituted or unsubstituted alkylene group; a substituted or unsubstituted cycloalkylene group; or selected from among the following structural formulae,

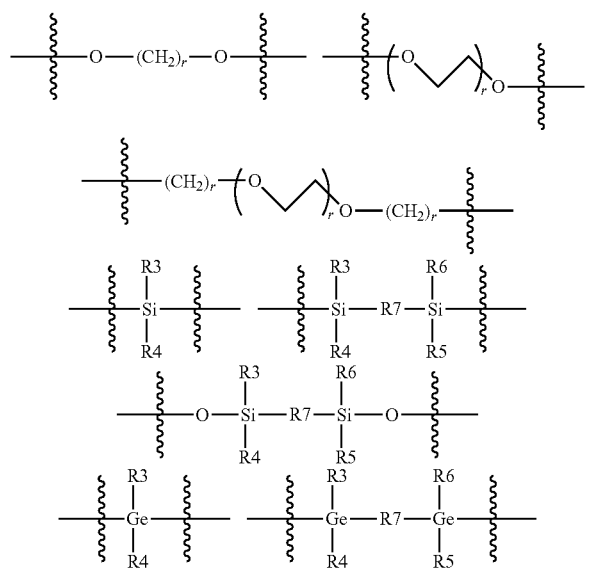

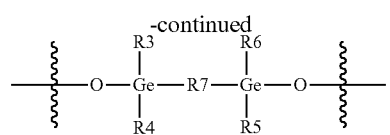

in the structural formulae, r is an integer of 1 to 20,

R3 to R6 are the same as or different from each other, and each independently a substituted or unsubstituted alkyl group, or a substituted or unsubstituted aryl group, R7 is a direct bond; a substituted or unsubstituted alkylene group; a substituted or unsubstituted cycloalkylene group; or a substituted or unsubstituted arylene group, and

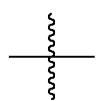

means a site bonding to Ar7 and Ar8.

In one embodiment of the present specification, the compound of Chemical Formula 1 preferably includes compounds having solubility for proper organic solvents.

The compound according to one embodiment of the present specification has strengthened symmetry by the presence of the amine group on both sides of the pyrenyl group, and thereby has properties of high light emission efficiency and long lifetime when manufacturing an organic light emitting device, and since the pyrenyl group is present as a dimer, solubility and coating properties are enhanced compared to compounds present as a monomer, and as a result, processability may be enhanced by allowing a solution process. In addition, by having the linker (L), the compound according to one embodiment of the present specification is suited to be used as a blue dopant since a light emission wavelength moves to a shorter wavelength compared to compounds without a linker, and is suited to be used as a blue dopant since a conjugation length decreases moving a light emission wavelength to a shorter wavelength compared to when the linker is an aryl group.

Hereinafter, substituents of the present specification will be described in detail, however, the substituents are not limited thereto.

In the present specification,

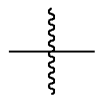

means a site bonding to other substituents or bonding sites.

In the present specification, the term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the term "substituted or unsubstituted" means being substituted with one or more substituents selected from the group consisting of hydrogen; deuterium; a halogen group; a cyano group; an alkyl group; a cycloalkyl group; a fluoroalkyl group; an aryl group; and a heterocyclic group, or being unsubstituted, or being substituted with a substituent linking two or more substituents among the substituents illustrated above, or being unsubstituted.

In the present specification, examples of the halogen group may include fluorine, chlorine, bromine or iodine.

In the present specification, the alkyl group may be linear, branched or cyclic, and although not particularly limited thereto, the number of carbon atoms is preferably from 1 to 50. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

The alkyl group may be substituted with an aryl group or a heteroaryl group to function as an arylalkyl group or a heteroarylalkyl group. The aryl group and the heterocyclic group may be selected from among examples of the aryl group or the heterocyclic group to describe below.

In the present specification, the cycloalkyl group is not particularly limited, but preferably has 3 to 60 carbon atoms. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the fluoroalkyl group means hydrogen of the alkyl group being substituted with fluorine, and may include a trifluoromethyl group, a perfluoroethyl group and the like, but are not limited thereto.

In the present specification, when the aryl group is a monocyclic aryl group, the number of carbon atoms is not particularly limited, but is preferably from 6 to 25. Specific examples of the monocyclic aryl group may include a phenyl group, a biphenyl group, a terphenyl group, a quaterphenyl group and the like, but are not limited thereto.

When the aryl group is a polycyclic aryl group, the number of carbon atoms is not particularly limited, but is preferably from 10 to 30. Specific examples of the polycyclic aryl group may include a naphthyl group, an anthracenyl group, a phenanthryl group, a pyrenyl group, a perylenyl group, a chrysenyl group, a fluorenyl group and the like, but are not limited thereto.

In the present specification, the fluorenyl group may be substituted, and adjacent substituents may bond to each other to form a ring.

When the fluorenyl group is substituted,

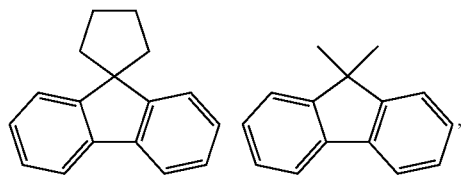

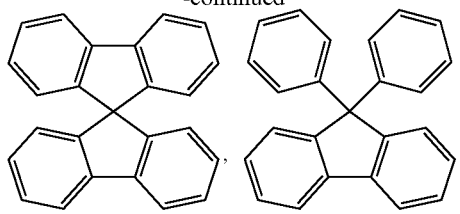

and the like may be included. However, the compound is not limited thereto.

The aryl group may be substituted with an alkyl group to function as an alkylaryl group. The alkyl group may be selected from among the examples described above.

In the present specification, the heterocyclic group is a group including one or more atoms that are not carbon, that is, heteroatoms, and specifically, the heteroatom may include one or more atoms selected from the group consisting of O, N, Se, S and the like. The number of carbon atoms is not particularly limited, but is preferably from 2 to 30, and the heterocyclic group may be monocyclic or polycyclic. Examples of the heterocyclic group may include a thiophene group, a furan group, a pyrrole group, an imidazole group, a thiazole group, an oxazole group, an oxadiazole group, a pyridine group, a pyrimidine group, a triazine group, a triazole group, a quinolinyl group, a quinazoline group, a carbazole group, a benzoxazole group, a benzimidazole group, a benzothiazole group, a benzocarbazole group, a benzofuran group, a phenanthroline group, an isoxazole group, a thiadiazole group, a dibenzofuran group and the like, but are not limited thereto.

In the present specification, the arylene group means the aryl group having two bonding sites, that is, a divalent group. Descriptions on the aryl group provided above may be applied thereto except for each being a divalent group.

In one embodiment of the present specification, Ar1 to Ar6 are the same as or different from each other, and each independently a substituted or unsubstituted aryl group having 6 to 30 carbon atoms; or a substituted or unsubstituted heterocyclic group having 2 to 30 carbon atoms.

In one embodiment of the present specification, Ar1 to Ar6 are the same as or different from each other, and each independently a substituted or unsubstituted phenyl group; a substituted or unsubstituted biphenyl group; a substituted or unsubstituted naphthyl group; a substituted or unsubstituted dibenzofuran group; a substituted or unsubstituted dibenzothiophene group; or a substituted or unsubstituted fluorene group.

In one embodiment of the present specification, Ar1 to Ar6 are the same as or different from each other, and each independently a phenyl group unsubstituted or substituted with deuterium, an alkyl group, a cycloalkyl group, a silyl group or an aryl group; a biphenyl group unsubstituted or substituted with deuterium, an alkyl group, a cycloalkyl group, a silyl group or an aryl group; a naphthyl group unsubstituted or substituted with deuterium, an alkyl group, a cycloalkyl group, a silyl group or an aryl group; or a dibenzofuran group unsubstituted or substituted with deuterium, an alkyl group, a cycloalkyl group, a silyl group or an aryl group.

In one embodiment of the present specification, Ar1 to Ar6 are the same as or different from each other, and each independently a phenyl group unsubstituted or substituted with deuterium, an alkyl group or a silyl group; a biphenyl group; a naphthyl group; or a dibenzofuran group unsubstituted or substituted with an alkyl group, a cycloalkyl group, a silyl group or an aryl group.

In one embodiment of the present specification, Ar1 to Ar6 are the same as or different from each other, and each independently a phenyl group unsubstituted or substituted with deuterium, a methyl group, an ethyl group, a propyl group, a butyl group, a butyldiphenylsilyl group or a trimethylsilyl group; a biphenyl group; a naphthyl group; or a dibenzofuran group unsubstituted or substituted with a butyl group, a cyclohexyl group, a trimethylsilyl group or a phenyl group.

In one embodiment of the present specification, Ar7 and Ar8 are the same as or different from each other, and each independently a substituted or unsubstituted arylene group having 6 to 30 carbon atoms; or a substituted or unsubstituted divalent heterocyclic group having 2 to 30 carbon atoms.

In one embodiment of the present specification, Ar7 and Ar8 are the same as or different from each other, and each independently a substituted or unsubstituted phenylene group; a substituted or unsubstituted biphenylylene group; a substituted or unsubstituted divalent naphthalene group; a substituted or unsubstituted divalent dibenzofuran group; a substituted or unsubstituted divalent dibenzothiophene group; or a substituted or unsubstituted divalent fluorene group.

In one embodiment of the present specification, Ar7 and Ar8 are the same as or different from each other, and each independently a phenylene group unsubstituted or substituted with deuterium; a biphenylylene group; a divalent naphthalene group; a divalent dibenzofuran group; a divalent dibenzothiophene group; or a divalent fluorene group.

In one embodiment of the present specification, Ar7 and Ar8 are the same as or different from each other, and each independently a substituted or unsubstituted phenylene group; or a substituted or unsubstituted naphthalene group.

In one embodiment of the present specification, Ar7 and Ar8 are the same as or different from each other, and each independently a phenylene group unsubstituted or substituted with deuterium; or a divalent naphthalene group unsubstituted or substituted with deuterium.

In one embodiment of the present specification, Ar7 and Ar8 are the same as or different from each other, and each independently a phenylene group unsubstituted or substituted with deuterium; or a divalent naphthalene group.

In one embodiment of the present specification, "substituted or unsubstituted" in Ar1 to Ar8 means being substituted with one or more substituents selected from the group consisting of a halogen group, a cyano group, an alkyl group, a fluoroalkyl group, a silyl group, a cycloalkyl group, an aryl group and a heterocyclic group, or being unsubstituted.

In one embodiment of the present specification, "substituted or unsubstituted" in Ar1 to Ar8 means being substituted with one or more substituents selected from the group consisting of a methyl group, an ethyl group, an isopropyl group, a tert-butyl group, a 2-ethylhexyl group, a trimethylsilyl group, a triphenylsilyl group, a tert-butyldimethylsilyl group, a cyclopropyl group, a cyclobutyl group, a cyclopentyl group, a cyclohexyl group, fluorine, a cyano group, a trifluoromethyl group, a phenyl group, a naphthyl group and a dibenzofuran group, or being unsubstituted.

In one embodiment of the present specification, Ar1 to Ar6 are the same as or different from each other, and each independently selected from among the following structural formulae,

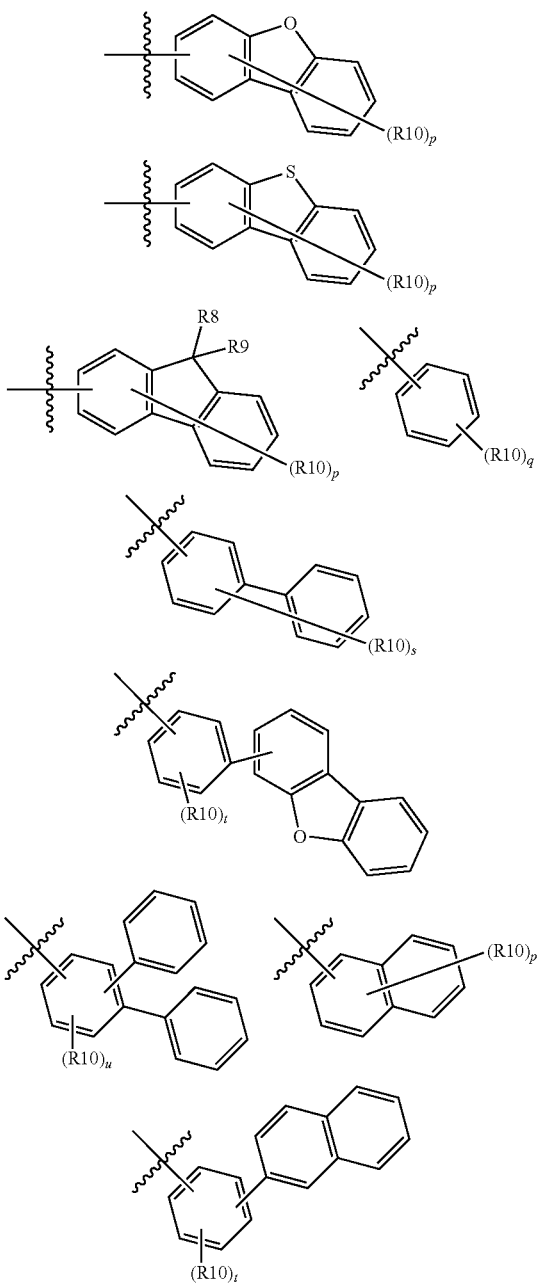

in the structural formulae, R8 and R9 are the same as or different from each other, and each independently a substituted or unsubstituted alkyl group; or a substituted or unsubstituted aryl group, R10 is hydrogen; deuterium; a halogen group; a cyano group; a substituted or unsubstituted alkyl group; a substituted or unsubstituted fluoroalkyl group; a substituted or unsubstituted silyl group; a substituted or unsubstituted aryl group; or a substituted or unsubstituted cycloalkyl group, p is an integer of 1 to 7, q is an integer of 1 to 5, s is an integer of 1 to 9, t is an integer of 1 to 4, u is an integer of 1 to 3, and when p, q, s, t and u are 2 or greater, R10s are the same as or different from each other,

means site bonding to N of Chemical Formula 1,

Ar7 and Ar8 are the same as or different from each other, and each independently selected from among the above-mentioned structural formulae, and in the structural formulae, one of R10s bonds to L of Chemical Formula 1.

In one embodiment of the present specification, R8 and R9 are the same as or different from each other, and each independently a substituted or unsubstituted alkyl group having 1 to 20 carbon atoms.

In one embodiment of the present specification, R8 and R9 are the same as or different from each other, and each independently an alkyl group having 1 to 20 carbon atoms.

In one embodiment of the present specification, R8 and R9 are the same as or different from each other, and each independently a methyl group or an ethyl group.

In one embodiment of the present specification, R10 is hydrogen; deuterium; a halogen group; a cyano group; a substituted or unsubstituted alkyl group having 1 to 20 carbon atoms; a substituted or unsubstituted fluoroalkyl group having 1 to 20 carbon atoms; a substituted or unsubstituted silyl group; or a substituted or unsubstituted cycloalkyl group having 3 to 20 carbon atoms.

In one embodiment of the present specification, R10 is hydrogen; deuterium; a methyl group; an ethyl group; an isopropyl group; a tert-butyl group; a 2-ethylhexyl group; a trimethylsilyl group; a triphenylsilyl group; a tert-butyldimethylsilyl group; a cyclopropyl group; a cyclobutyl group; a cyclopentyl group; a cyclohexyl group; fluorine; a cyano group; or a trifluoromethyl group.

In one embodiment of the present specification, R1 and R2 are hydrogen.

In one embodiment of the present specification, R1 and R2 are the same as or different from each other, and each independently hydrogen or an alkyl group.

In one embodiment of the present specification, R1 and R2 are the same as or different from each other, and each independently hydrogen; a methyl group; an ethyl group; a propyl group; or a butyl group.

In one embodiment of the present specification, R1 and R2 are the same as or different from each other, and each independently hydrogen; or a propyl group.

In one embodiment of the present specification, R1 and R2 are the same as or different from each other, and each independently hydrogen; or an isopropyl group.

In one embodiment of the present specification, Ar2 to Ar5 are the same as each other, Ar1 and Ar6 are the same as each other, and Ar7 and Ar8 are the same as each other.

In one embodiment of the present specification, at least one of Ar1 and Ar2 is a substituted or unsubstituted dibenzofuran group; a substituted or unsubstituted dibenzothiophene group; or a substituted or unsubstituted fluorene group, and the rest is a substituted or unsubstituted phenyl group; or a substituted or unsubstituted naphthyl group.

In one embodiment of the present specification, L is an alkylene group; or selected from among the following structural formulae.

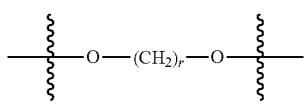

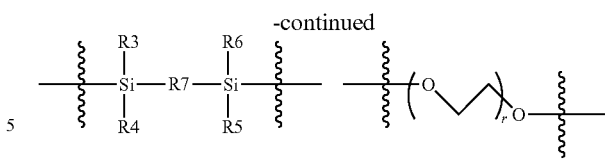

In one embodiment of the present specification, L is a methylene group; an ethylene group; a propylene group; a butylene group; a cyclopentylene group; a cyclohexylene group; or selected from among the following structural formulae.

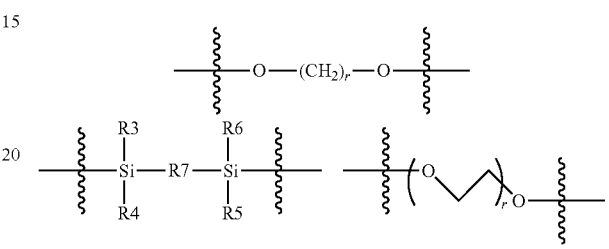

In one embodiment of the present specification, r is an integer of 1 to 5.

In one embodiment of the present specification, r is 2 or 3.

In one embodiment of the present specification, R7 is a direct bond, an ethylene group, a cyclohexylene group or a phenylene group.

In one embodiment of the present specification, R3 to R6 are the same as or different from each other, and each independently a methyl group or a phenyl group.

In one embodiment of the present specification, L is selected from among the following structural formulae.

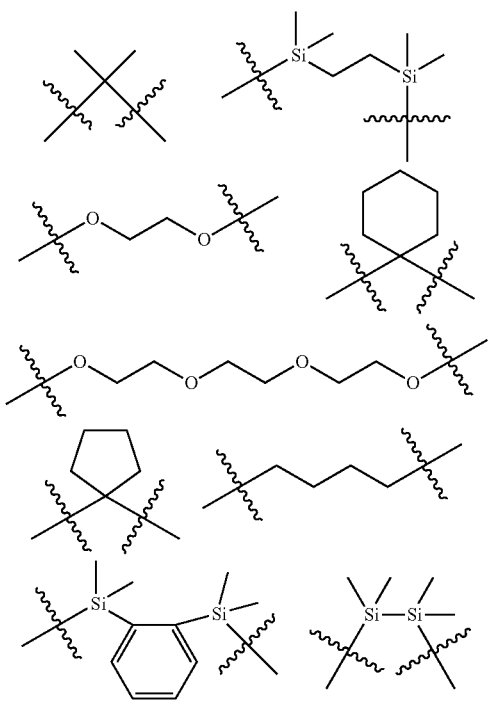

13
-continued
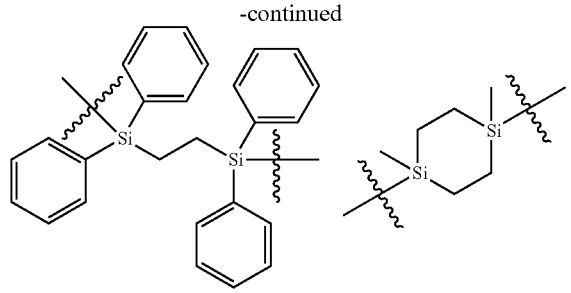
14
-continued
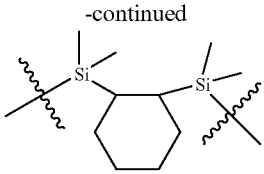
In one embodiment of the present specification, Chemical Formula 1 is represented by any one of the following structural formulae.
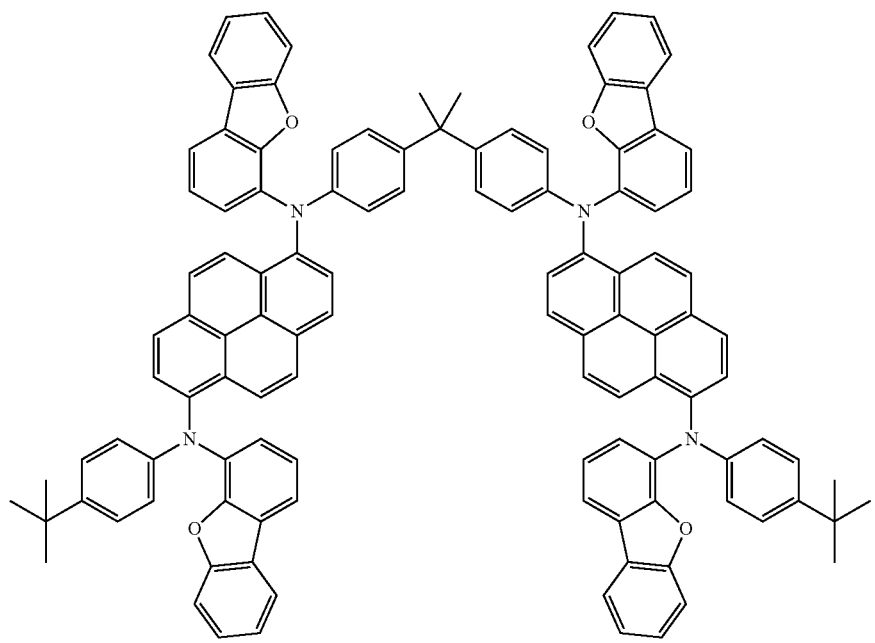
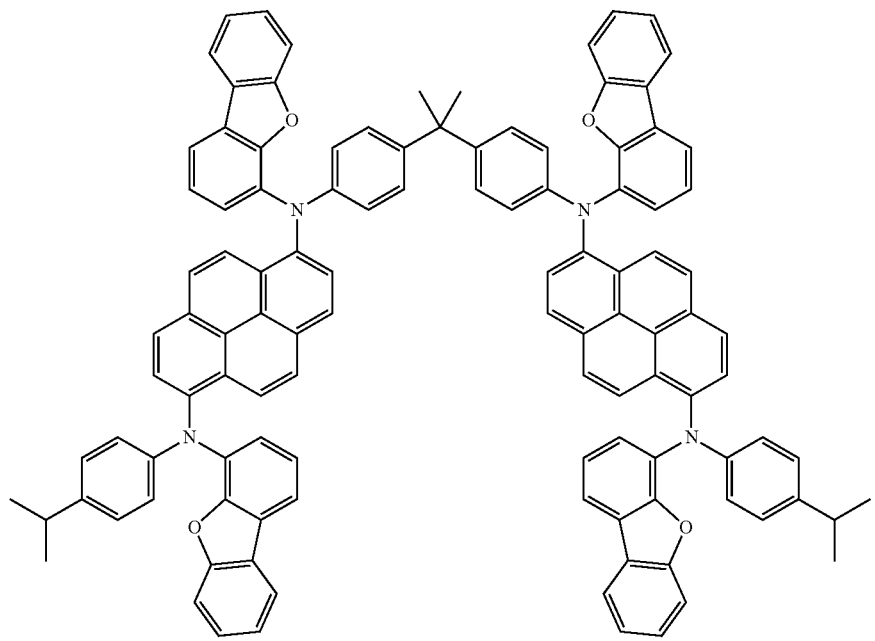

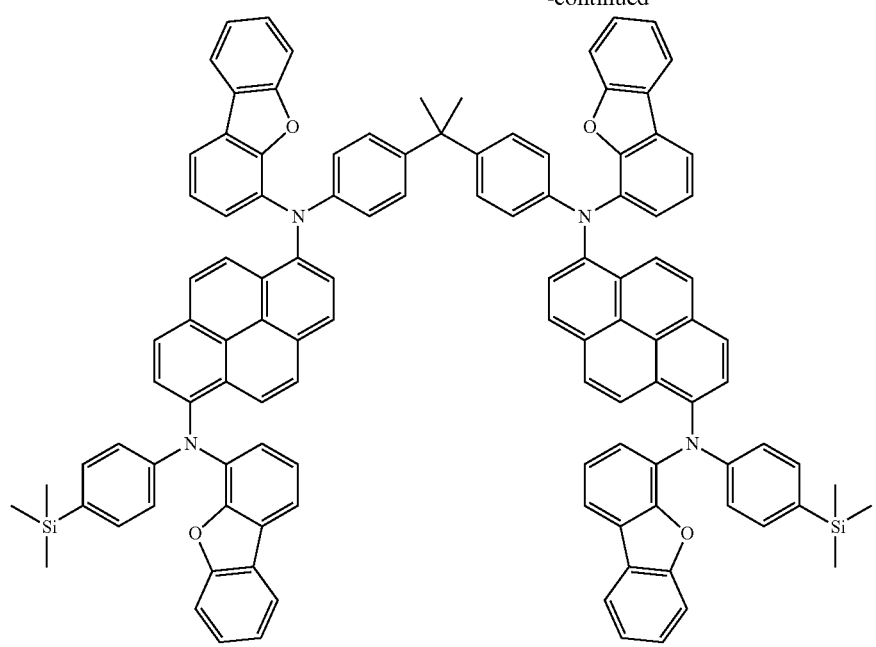
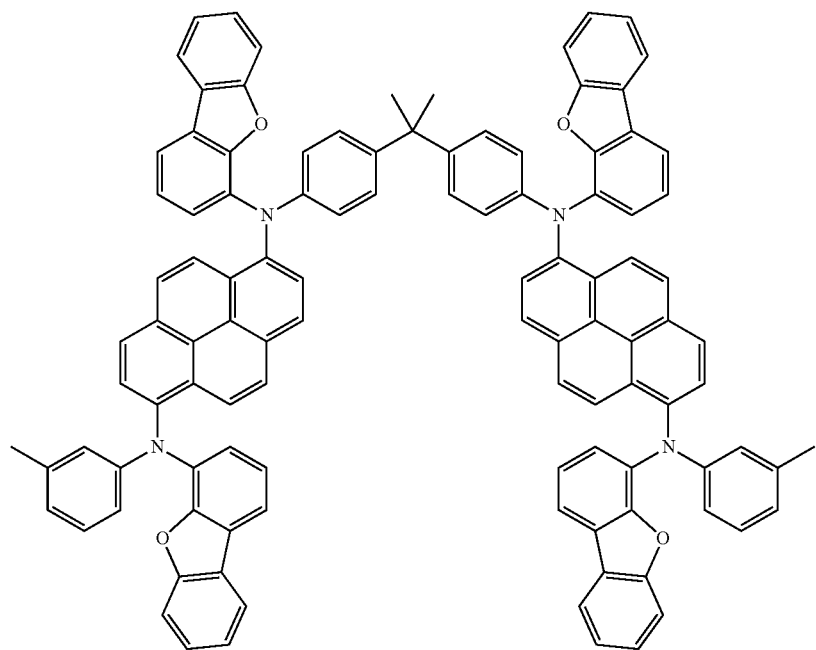

-continued
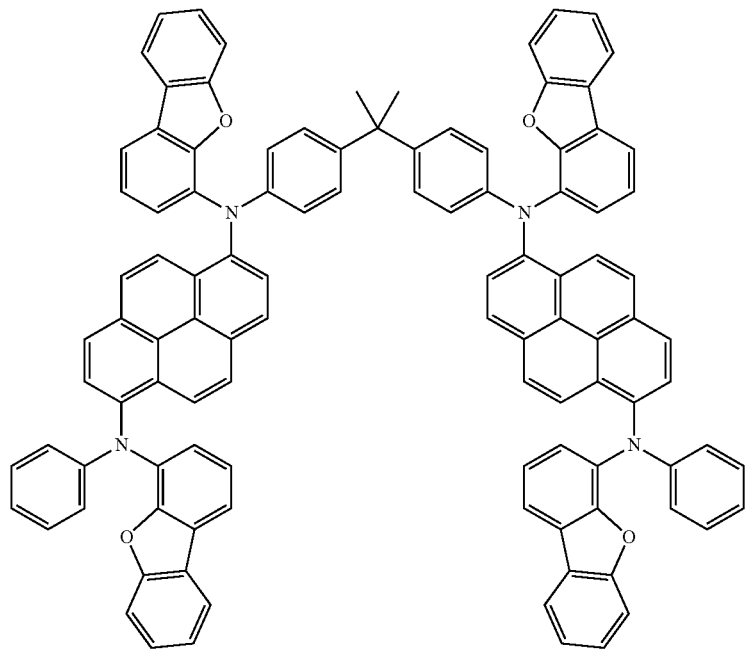
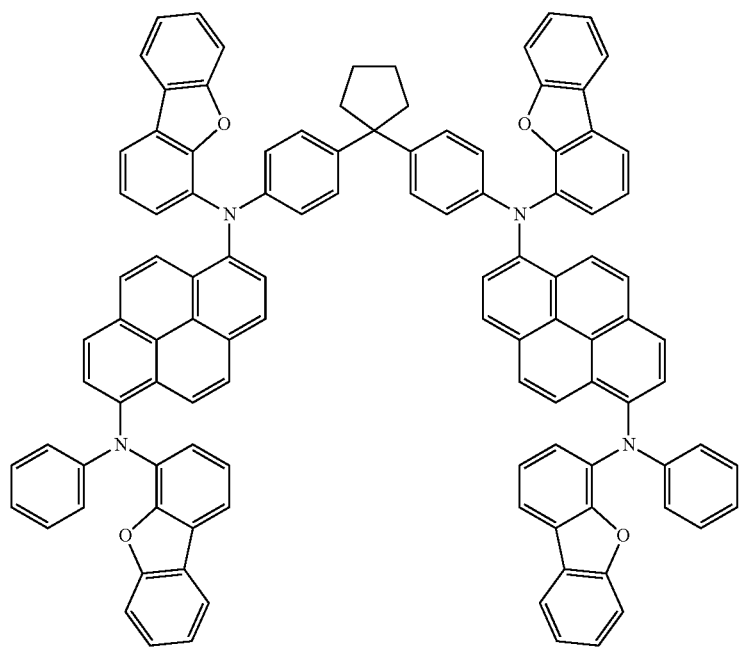

-continued
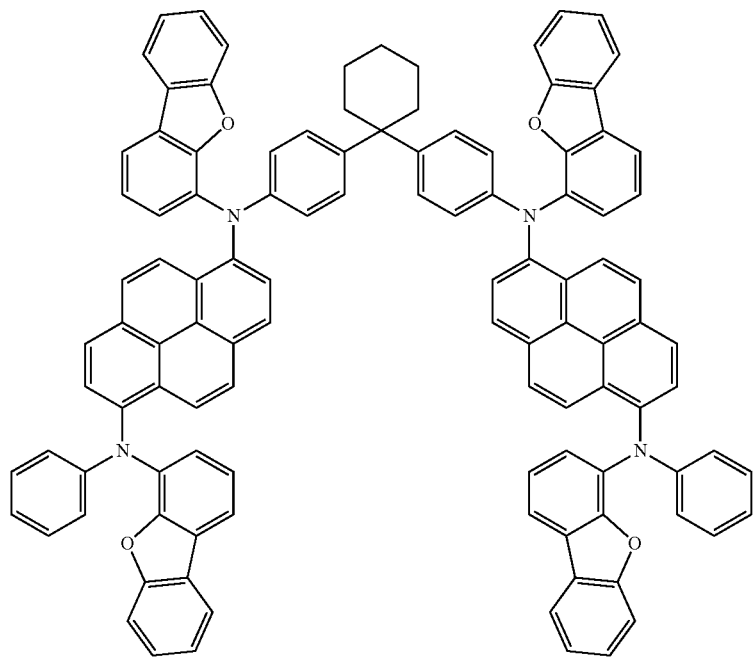
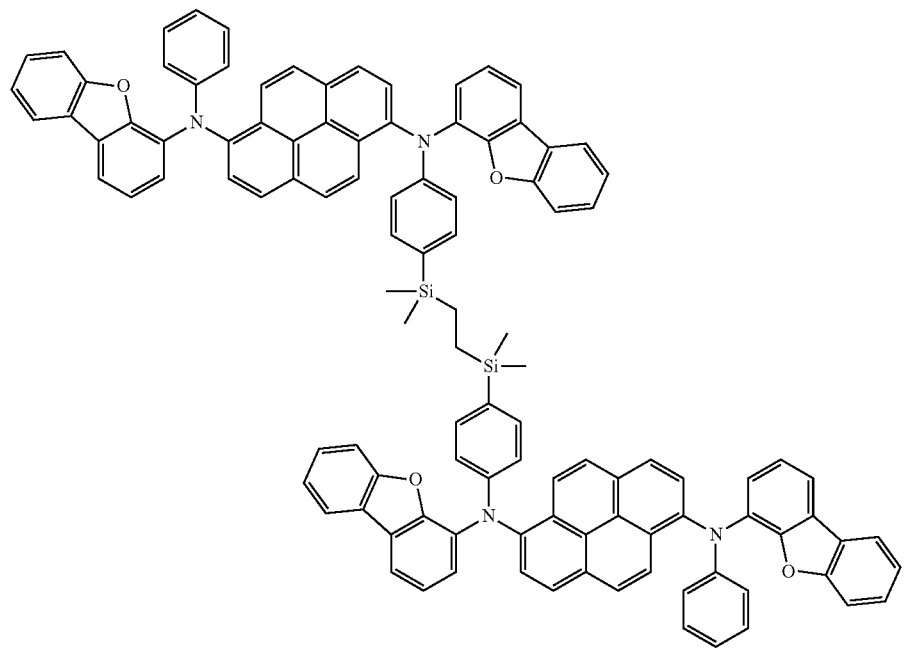

-continued
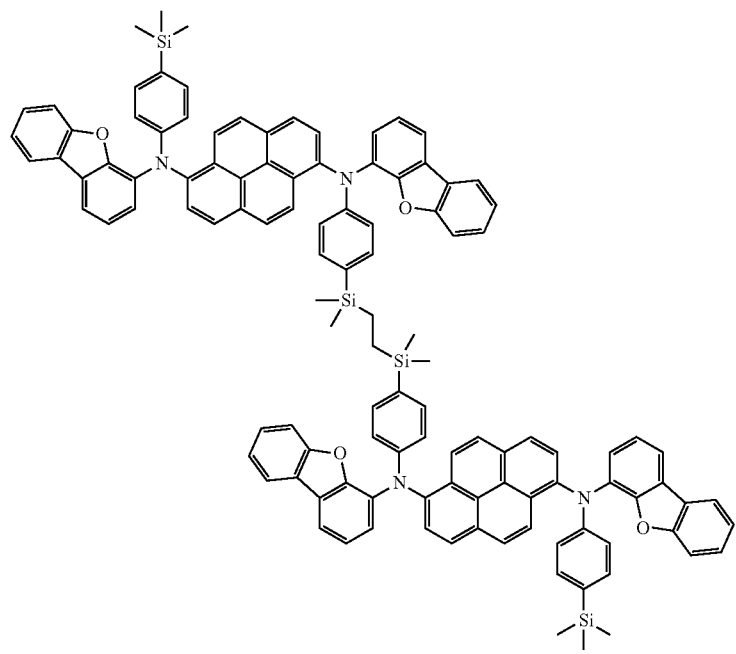
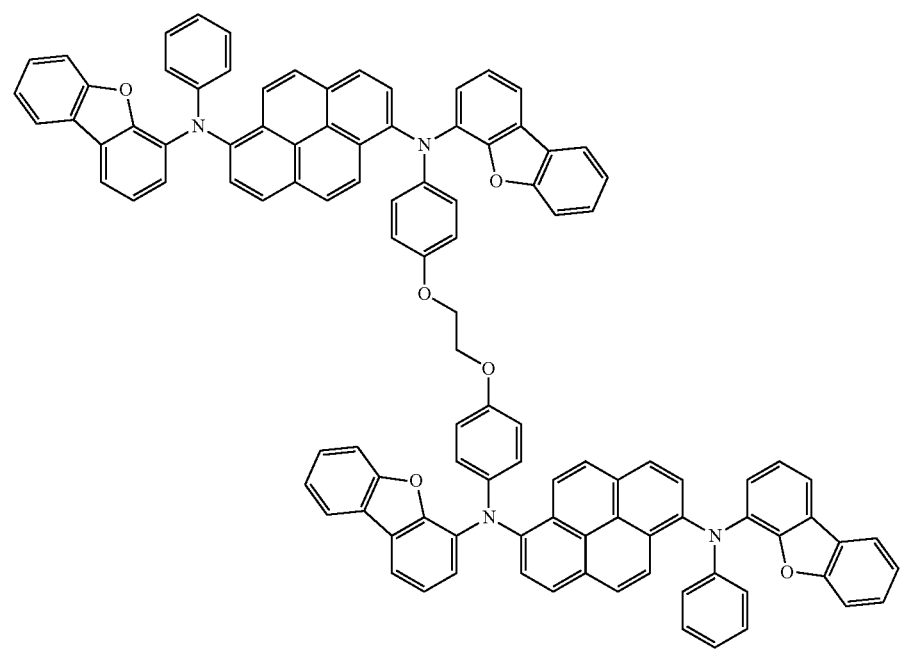

-continued
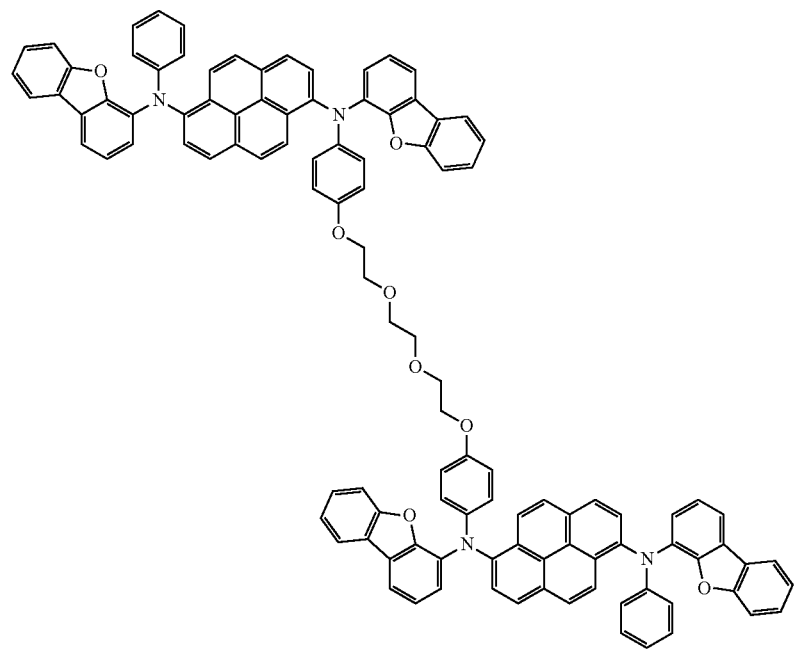
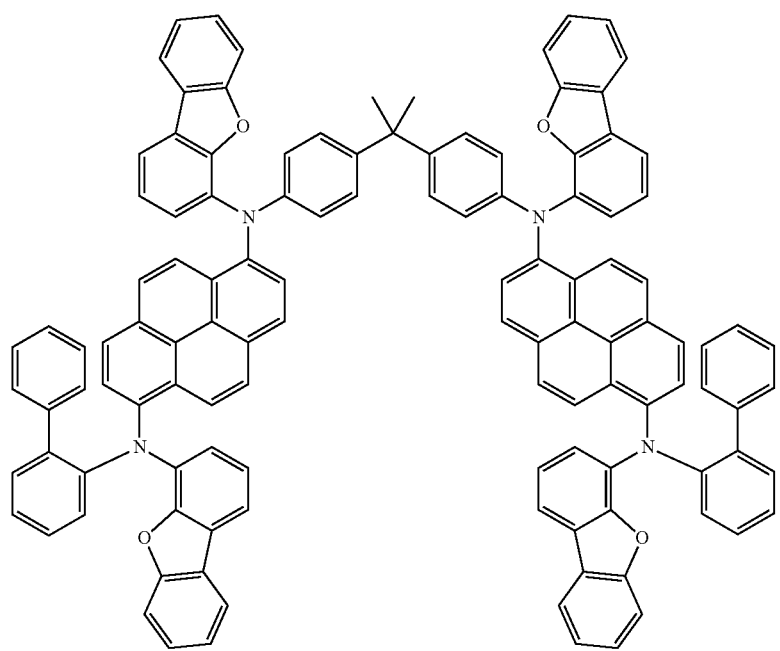

-continued
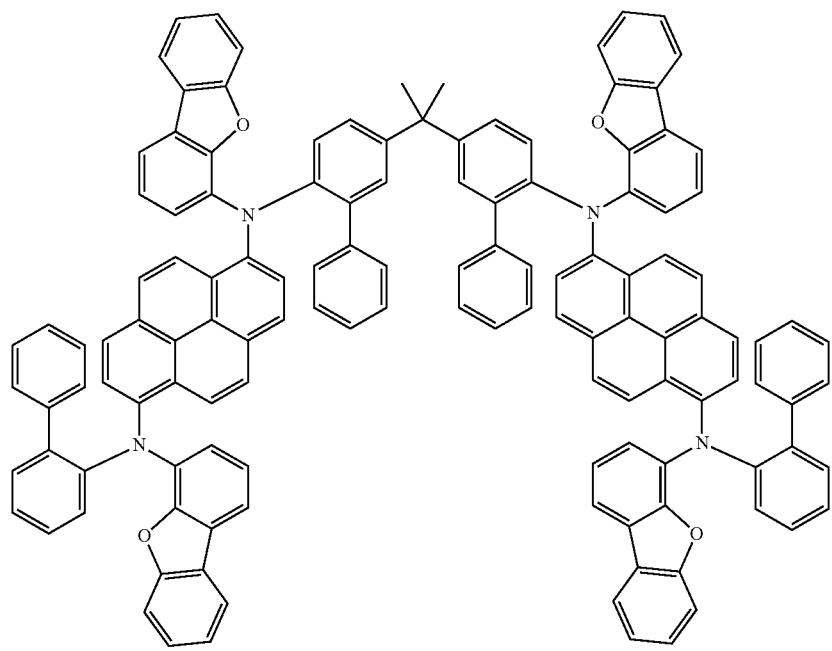
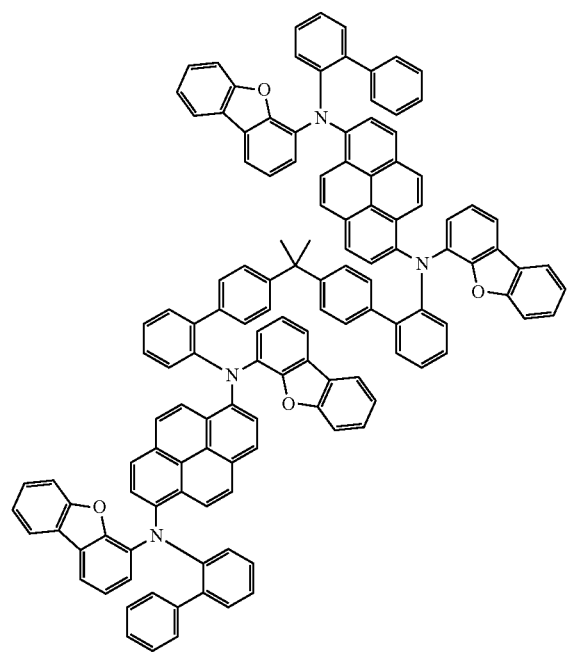

-continued
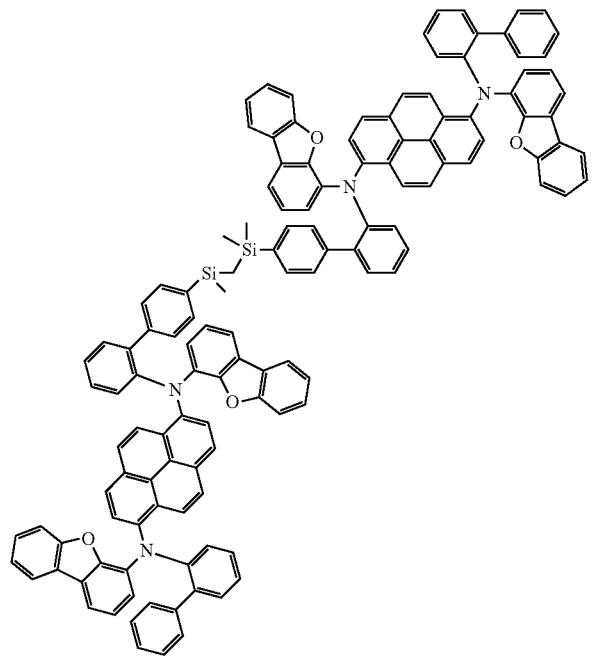
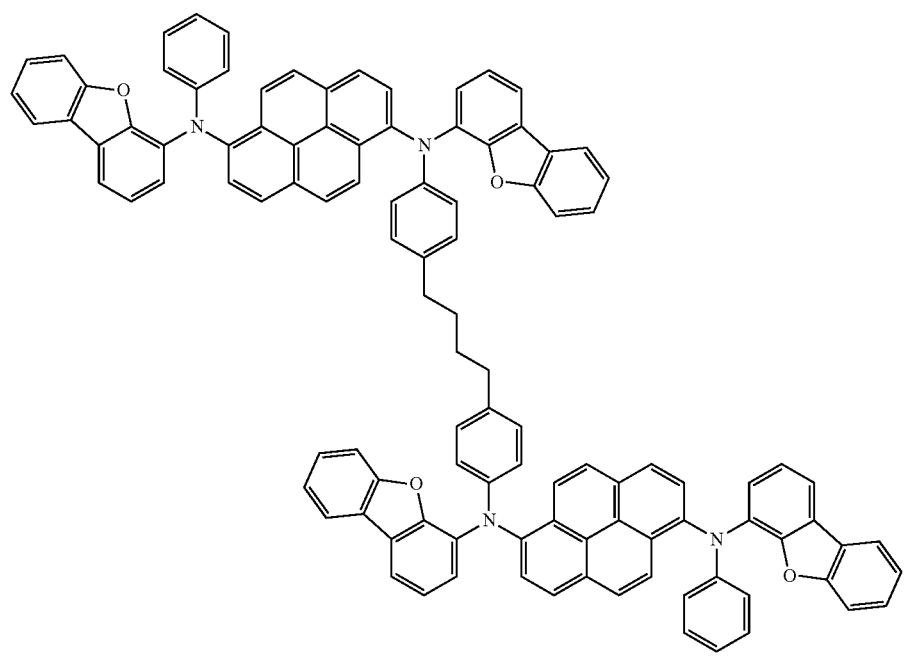

-continued
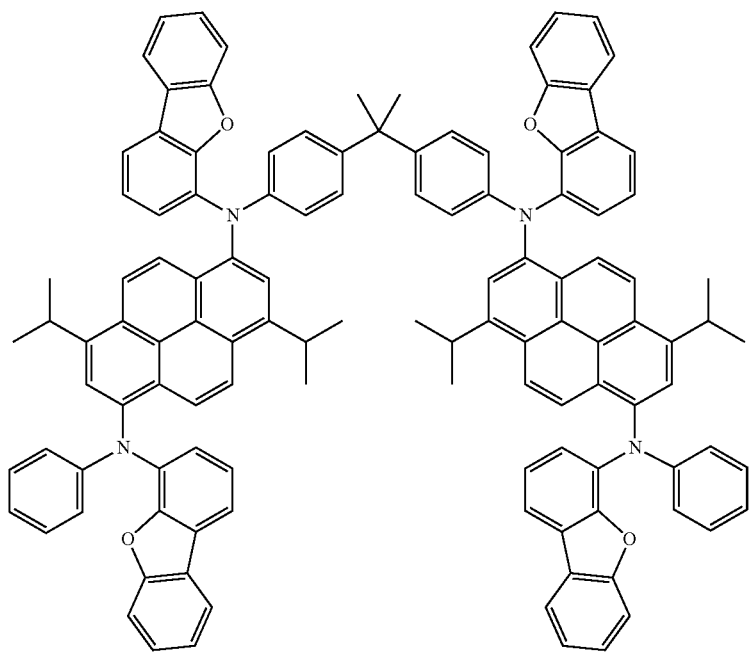
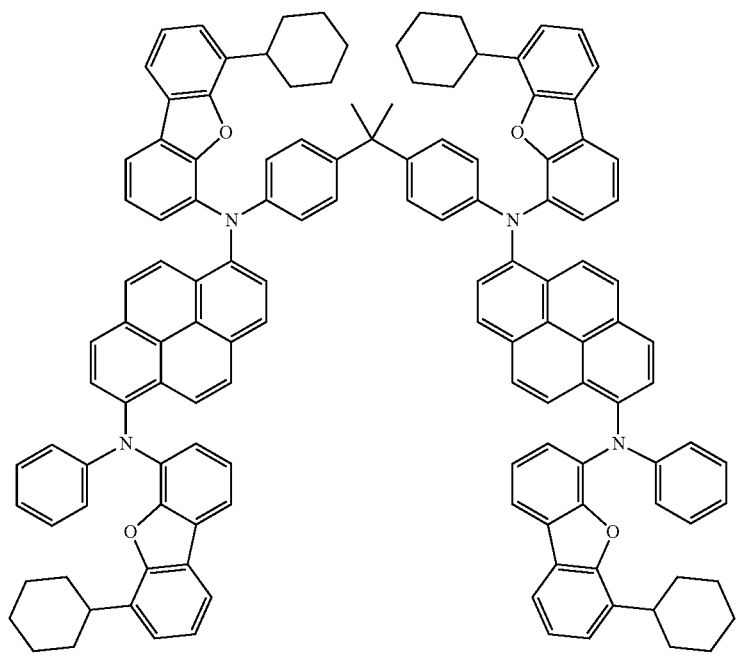

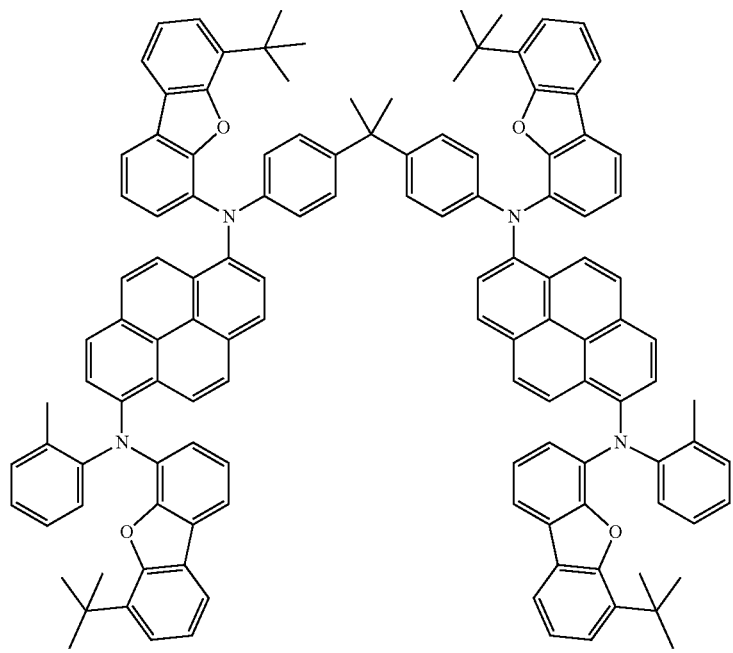
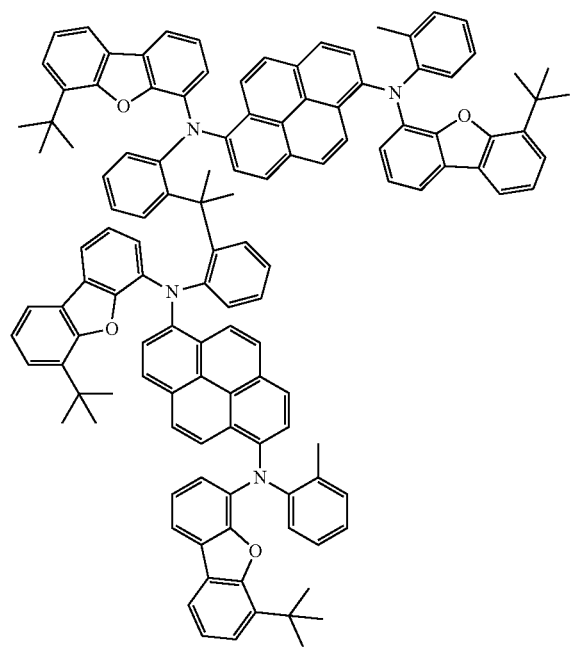

-continued
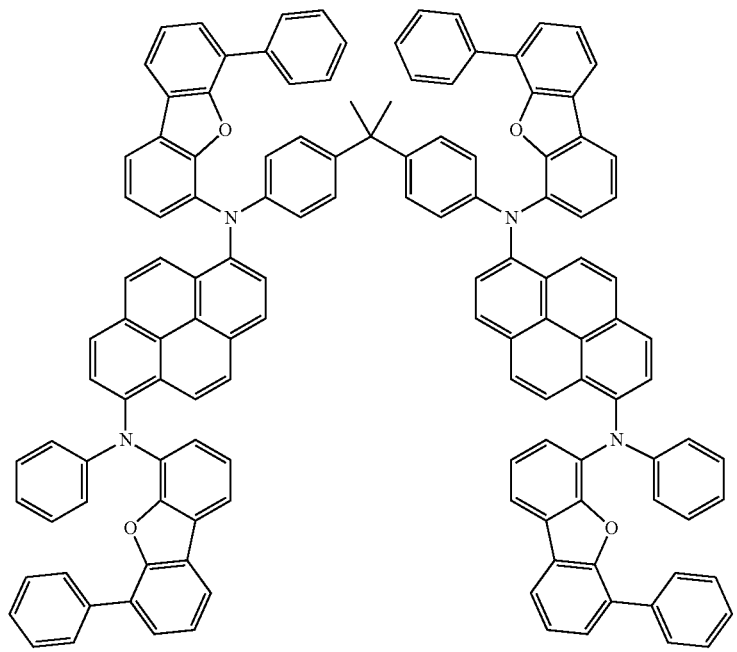
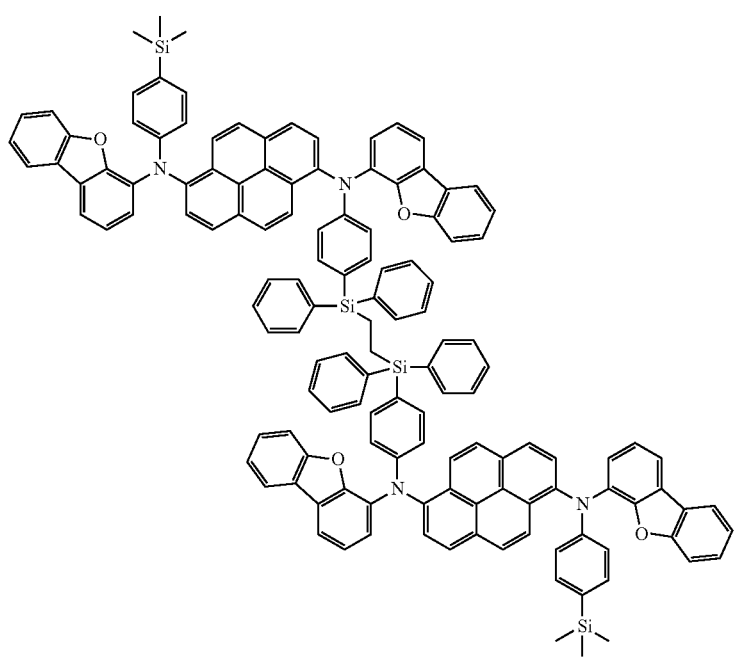

35
36
-continued
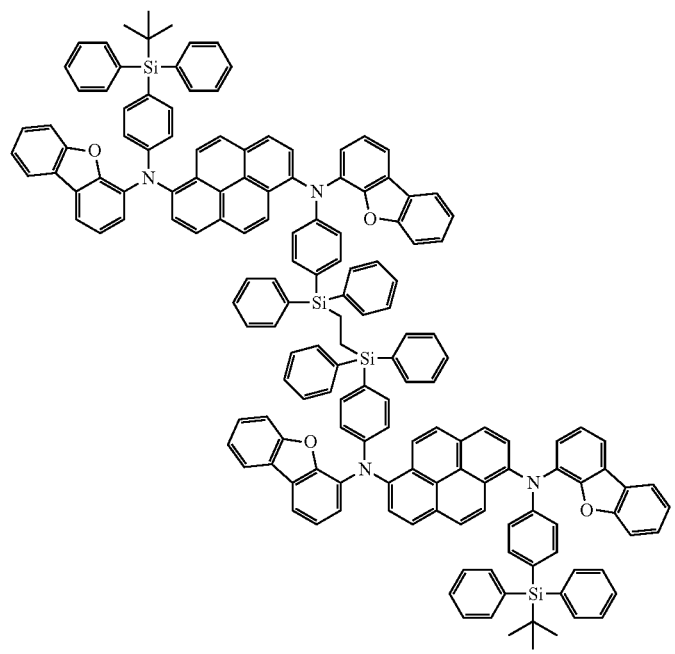
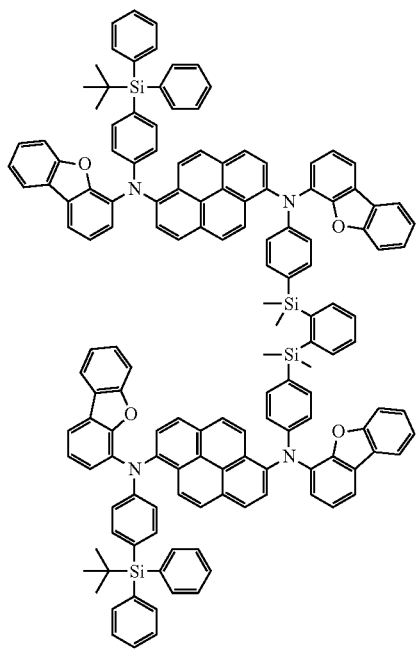
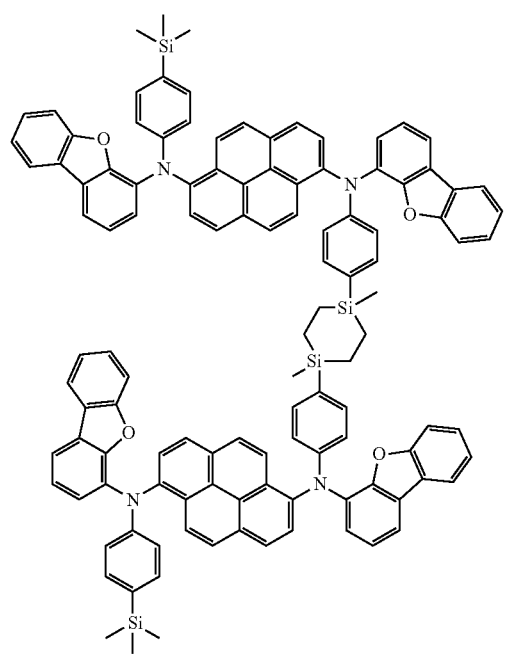

-continued
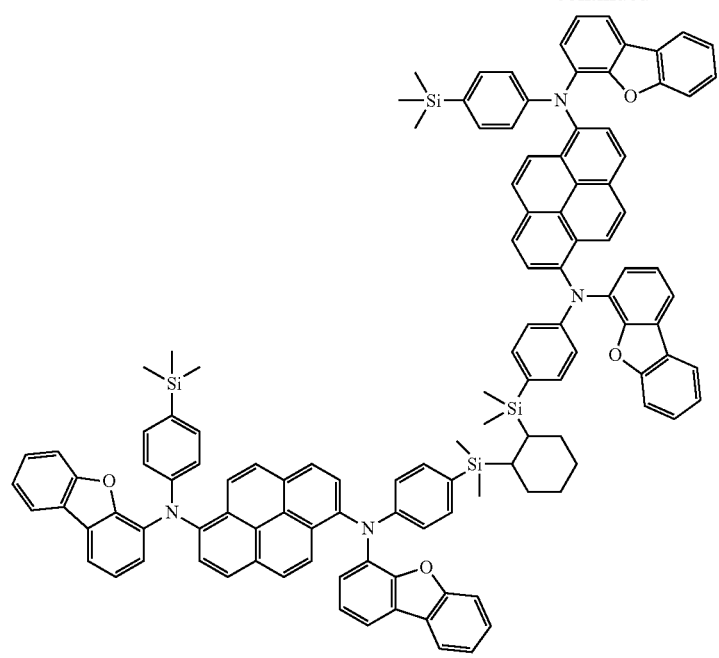
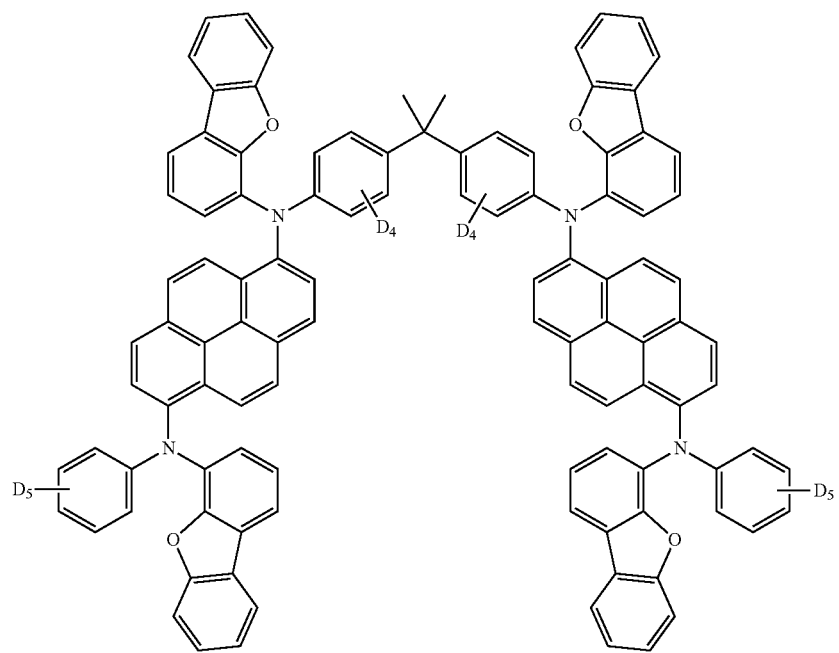

-continued
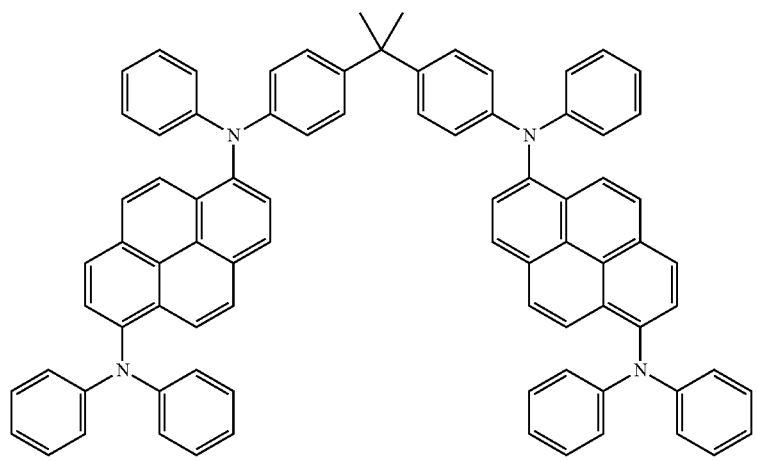
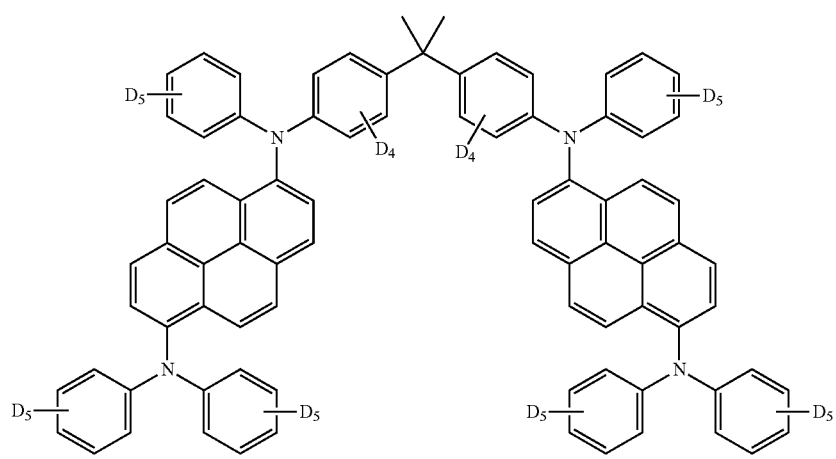
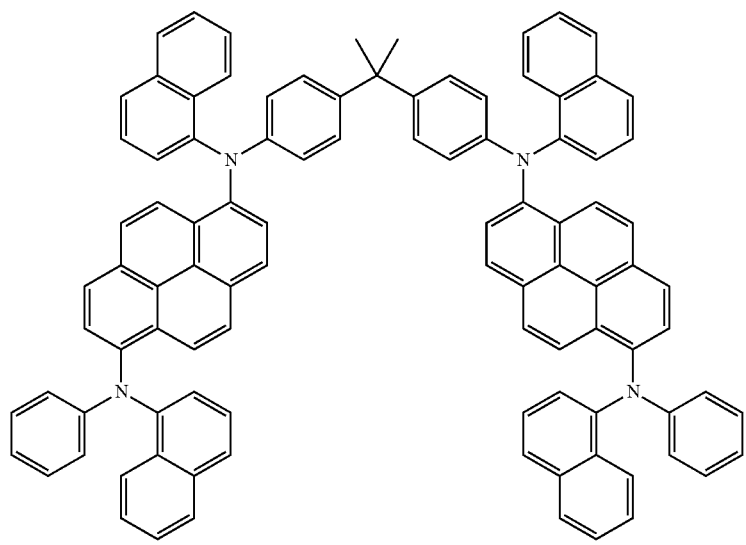

-continued
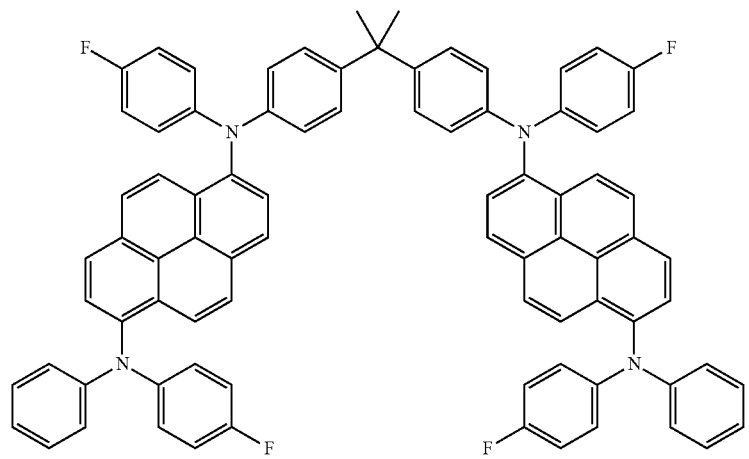
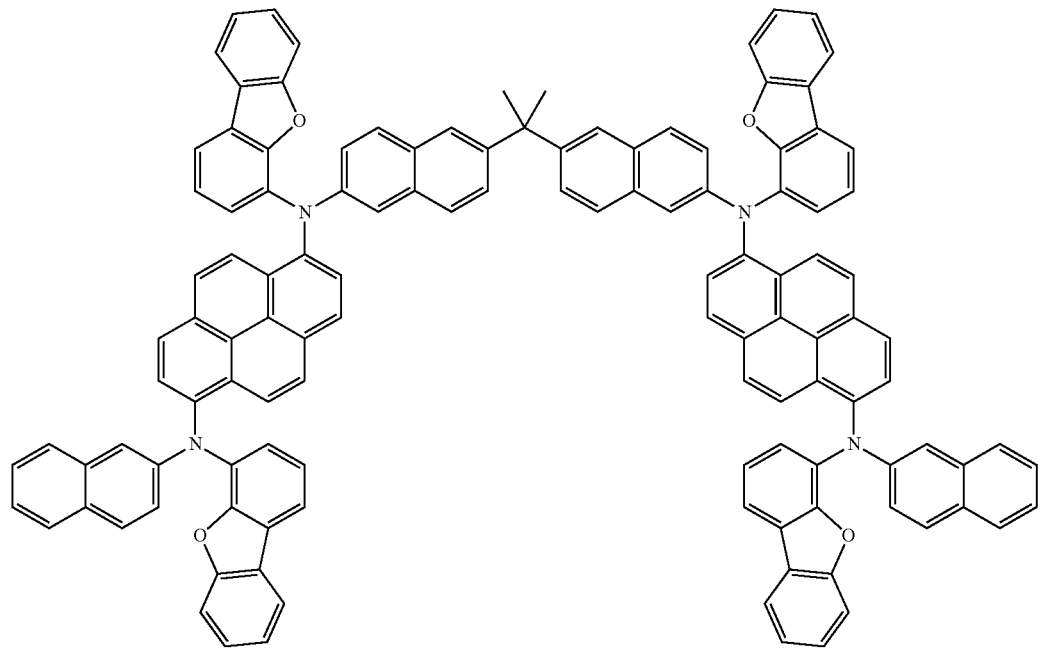

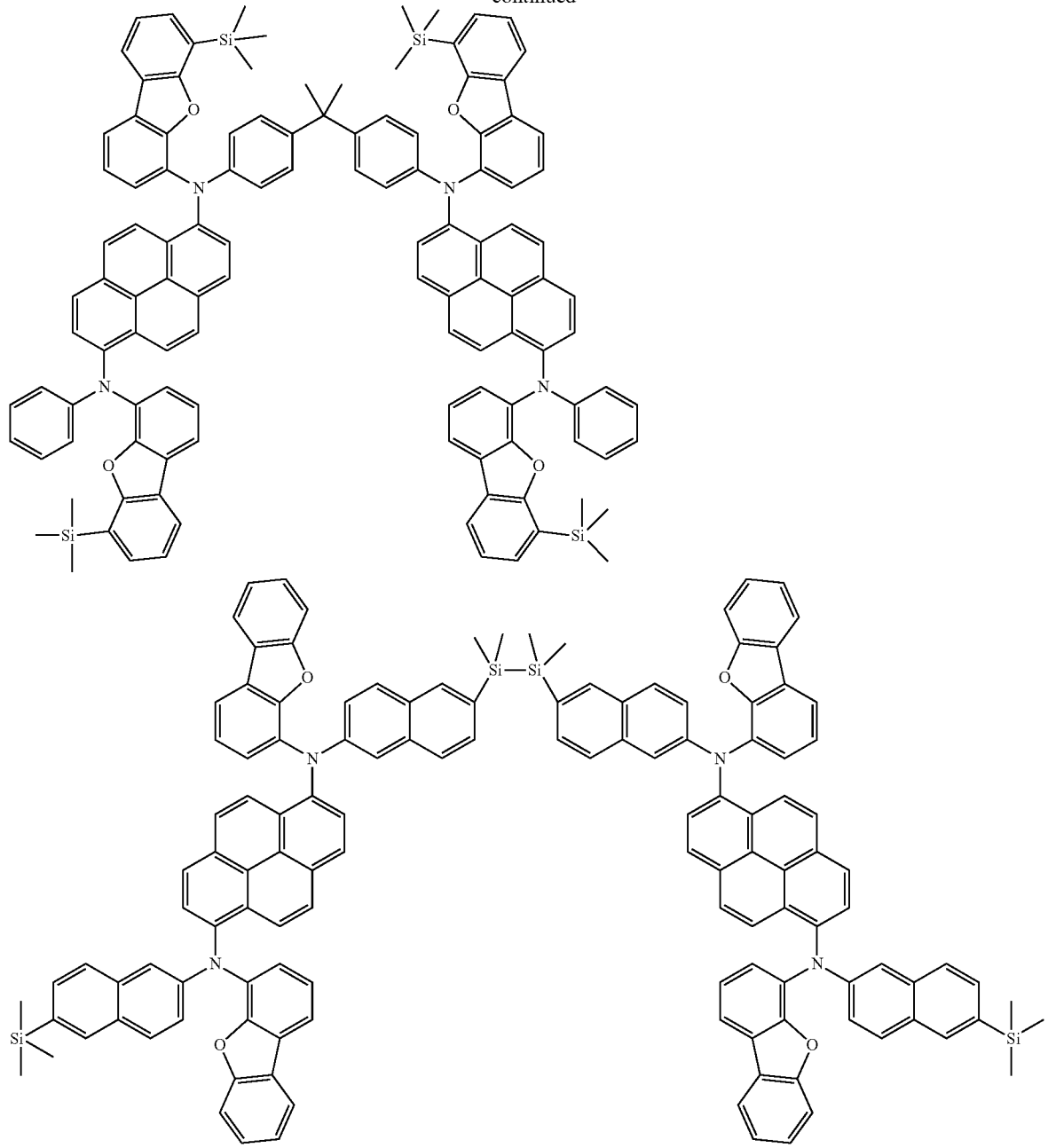

One embodiment of the present specification provides a coating composition including the compound of Chemical Formula 1.

In one embodiment of the present specification, the coating composition is for an organic light emitting device.

In one embodiment of the present specification, the coating composition includes the compound of Chemical Formula 1 and a solvent.

In one embodiment of the present specification, the coating composition may be a liquid phase. The "liquid phase" means in a liquid state at room temperature and atmospheric pressure.

In one embodiment of the present specification, examples of the solvent may include chlorine-based solvents such as chloroform, methylene chloride, 1,2-dichloroethane, 1,1,2-trichloroethane, chlorobenzene or o-dichlorobenzene; ether-based solvents such as tetrahydrofuran or dioxane; aromatic hydrocarbon-based solvents such as toluene, xylene, trimethylbenzene or mesitylene; aliphatic hydrocarbon-based solvents such as cyclohexane, methylcyclohexane, n-pentane, n-hexane, n-heptane, n-octane, n-nonane or n-decane; ketone-based solvents such as acetone, methyl ethyl ketone or cyclohexanone; ester-based solvents such as ethyl acetate, butyl acetate or ethyl cellosolve acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin or 1,2-hexanediol, and derivatives thereof; alcohol-based solvents such as methanol, ethanol, propanol, isopropanol or cyclohexanol; sulfoxide-based solvents such as dimethyl sulfoxide; amide-based solvents such as N-methyl-2-pyrrolidone or N,N-dimethylformamide; benzoate-based solvents such as methyl benzoate, butyl benzoate or 3-phenoxybenzoate; tetraline, and the like, however, the solvent is not limited thereto as long as it is a solvent capable of dissolving or dispersing the compound according to one embodiment of the present disclosure.

In another embodiment, the solvent may be used either alone as one type, or as a mixture of two or more solvent types.

In another embodiment, the solvent has a boiling point of preferably 40° C. to 250° C. and more preferably 60° C. to 230° C., however, the boiling point is not limited thereto.

In another embodiment, the single or mixed solvent has viscosity of preferably 1 cP to 10 cP and more preferably 3 CP to 8 CP, however, the viscosity is not limited thereto.

In another embodiment, the coating composition has a concentration of preferably 0.1 wt/v % to 20 wt/v % and more preferably 0.5 wt/v % to 5 wt/v %, however, the concentration is not limited thereto.

Another embodiment of the present specification provides an organic light emitting device including the coating composition.

In one embodiment of the present specification, the organic light emitting device includes a first electrode; a second electrode; and one or more organic material layers provided between the first electrode and the second electrode, wherein one or more layers of the organic material layers include the coating composition including the compound of Chemical Formula 1.

In one embodiment of the present specification, the organic material layer including the coating composition is a hole transfer layer, a hole injection layer, or a layer carrying out hole transfer and hole injection at the same time.

In another embodiment, the organic material layer including the coating composition is a light emitting layer.

In another embodiment, the organic material layer including the coating composition is a light emitting layer, and the light emitting layer includes the compound as a host of the light emitting layer.

In an embodiment of the present specification, the organic material layer including the coating composition is a light emitting layer, and the light emitting layer includes the compound as a dopant of the light emitting layer.

In an embodiment of the present specification, the organic material layer including the coating composition is a light emitting layer, and the light emitting layer includes the compound as a dopant of the light emitting layer, and includes a fluorene derivative as a host.

In an embodiment of the present specification, the organic material layer including the coating composition is a light emitting layer, and the light emitting layer includes the compound as a dopant of the light emitting layer, and includes poly(9,9-di-n-octylfluorenyl-2,7-diyl) as a host.

In an embodiment of the present specification, the organic material layer including the coating composition is a light emitting layer, and the light emitting layer includes the compound as a dopant of the light emitting layer, and includes a fluorene derivative as a host in a weight ratio of 1:1 to 1:50.

In an embodiment of the present specification, the organic material layer including the coating composition is a light emitting layer, and the light emitting layer includes the compound as a dopant of the light emitting layer, and includes a fluorene derivative as a host in a weight ratio of 6:100.

In one embodiment of the present specification, the organic light emitting device further includes one, two or more layers selected from the group consisting of a hole injection layer, a hole transfer layer. an electron transfer layer, an electron injection layer, an electron blocking layer and a hole blocking layer.

In one embodiment of the present specification, the first electrode is a cathode, and the second electrode is an anode.

In one embodiment of the present specification, the first electrode is an anode, and the second electrode is a cathode.

In another embodiment, the organic light emitting device may be an organic light emitting device having a structure in which an anode, one or more organic material layers and a cathode are consecutively laminated on a substrate (normal type).

In another embodiment, the organic light emitting device may be an organic light emitting device having a structure in a reverse direction in which a cathode, one or more organic material layers and an anode are consecutively laminated on a substrate (inverted type).

The organic material layer of the organic light emitting device of the present specification may be formed in a single layer structure, but may also be formed in a multilayer structure in which two or more organic material layers are laminated. For example, the organic light emitting device of the present disclosure may have a structure including a hole injection layer, a hole transfer layer, a light emitting layer, an electron transfer layer, an electron injection layer and the like as the organic material layer. However, the structure of the organic light emitting device is not limited thereto, and may include less numbers of organic material layers.

For example, a structure of the organic light emitting device according to one embodiment of the present specification is illustrated in FIG. 1.

FIG. 1 illustrates a structure of the organic light emitting device in which an anode (201), a hole injection and transfer layer (301), a light emitting layer (501) and a cathode (601) are consecutively laminated on a substrate (101).

In FIG. 1, the hole injection and transfer layer (301), or the light emitting layer (501) includes the coating composition including the compound represented by Chemical Formula 1.

FIG. 1 illustrates the organic light emitting device, however, the organic light emitting device is not limited thereto.

When the organic light emitting device includes a plurality of organic material layers, the organic material layers may be formed with materials that are the same as or different from each other.

The organic light emitting device of the present specification may be manufactured using materials and methods known in the art, except that one or more layers of the organic material layers include the coating composition including the compound.

For example, the organic light emitting device of the present specification may be manufactured by consecutively laminating an anode, an organic material layer and a cathode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

In addition, one embodiment of the present specification also provides a method for manufacturing an organic light emitting device including the coating composition.

Specifically, the method for manufacturing an organic light emitting device in one embodiment of the present specification includes preparing a substrate; forming a cathode or an anode on the substrate; forming one or more organic material layers on the cathode or the anode; and forming an anode or a cathode on the organic material layers, wherein one or more layers of the organic material layers include the coating composition.

In one embodiment of the present specification, the organic material layer including the coating composition is formed using spin coating.

In another embodiment, the organic material layer including the coating composition is formed using a printing method.

In an embodiment of the present specification, examples of the printing method include inkjet printing, nozzle printing, offset printing, transfer printing, screen printing or the like, but are not limited thereto.

The coating composition according to one embodiment of the present specification is suited for a solution process due to its structural properties and may be formed using a printing method, and therefore, is economically effective in terms of time and costs when manufacturing a device.

In one embodiment of the present specification, the forming of an organic material layer including the coating composition includes coating the coating composition on the cathode or the anode; and heat treating or light treating the coated coating composition.

In one embodiment of the present specification, the coating composition is heat treated and dried.

In one embodiment of the present specification, the time of heat treating the organic material layer including the coating composition is preferably within 1 hour and more preferably within 30 minutes.

In one embodiment of the present specification, the atmosphere of heat treating the organic material layer formed using the coating composition is preferably inert gas such as argon or nitrogen.

When the heat treatment or the light treatment is included in the forming of an organic material layer formed using the coating composition, an organic material layer including a thin-filmed structure by a plurality of the fluorene groups included in the coating composition forming crosslinkage may be provided. In this case, the organic material layer formed using the coating composition may be prevented from being dissolved by a solvent deposited on the surface, or being morphologically affected or decomposed.

Accordingly, when the organic material layer including the coating composition is formed including the heat treatment or the light treatment, resistance for the solvent increases, and multiple layers may be formed by repeatedly carrying out solution deposition and crosslinking methods, and as a result, lifetime properties of a device may be enhanced by increasing stability.

In one embodiment of the present specification, the coating composition including the compound may use a coating composition mixed with and dispersed to a polymer binder.

As the polymer binder in one embodiment of the present specification, those that do not extremely inhibit charge transfer are preferred, and those that do not exhibit strong absorption for visible light are preferably used. Examples of the polymer binder include poly(N-vinylcarbazole), polyaniline and derivatives thereof, polythiophene and derivatives thereof, poly(p-phenylenevinylene) and derivatives thereof, poly(2,5-thienylenevinylene) and derivatives thereof, polycarbonate, polyacrylate, polymethyl acrylate, polymethyl methacrylate, polystyrene, polyvinyl chloride, polysiloxane and the like.

In addition, by including carbazole and an amine group, the compound according to one embodiment of the present specification may be included alone in the organic material layer, may be thin-filmed through heat treating or light treating a coating composition including the compound, or may be included as a copolymer using a coating composition mixed with other monomers. In addition, a copolymer or a mixture may be included using a coating composition mixed with other polymers.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxy-quinoline aluminum complexes ($Alq_3$); carbazole-based compounds; dimerized styryl compounds; BAlq; 10-hydroxybenzo quinoline-metal compounds; benzoxazole-, benzothiazole- and benzimidazole-based compounds; poly(p-phenylenevinylene) (PPV)-based polymers; spiro compounds; polyfluorene, rubrene, or the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, however, the material is not limited thereto. In addition, a polymer compound may be used, and polymer compounds such as poly-1,4-phenylene or polyfluorene may be included, however, the polymer compound is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group and includes arylamino group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, however, the styrylamine compound is not limited thereto. In addition, the metal complex includes iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof include Al complexes of 8-hydroxyquinoline; complexes including $Alq_3$; organic radical compounds; hydroxyflavon-metal complexes, or the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited there.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)berylium, bis (10-hydroxybenzo[h]quinolinato)zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)gallium and the like, but is not limited thereto.

The hole blocking layer is a layer blocking holes from reaching a cathode, and generally, may be formed under the same condition as the hole injection layer. Specifically, oxadiazole derivatives or triazole derivatives, phenanthroline derivatives, BCP, aluminum complexes and the like are included, however, the material is not limited thereto.

The organic light emitting device according to the present specification may be a top-emission type, a bottom-emission type or a dual-emission type depending on the materials used.

In one embodiment of the present specification, the coating composition may be included in organic solar cells or organic transistors in addition to organic light emitting devices.

DETAILED IMPLEMENTATION FOR THE INVENTION

Hereinafter, the present specification will be described in detail with reference to examples in order to specifically describe the present specification. However, the examples according to the present specification may be modified to various different forms, and the scope of the present specification is not to be construed as being limited to the examples described below. Examples of the present specification are provided in order to more fully describe the present specification to those having average knowledge in the art.

Preparation Example 1

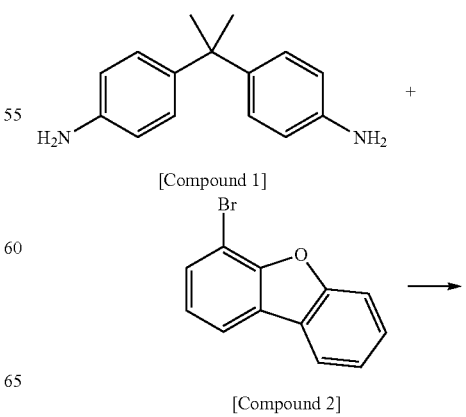

[Compound 1]

[Compound 2]

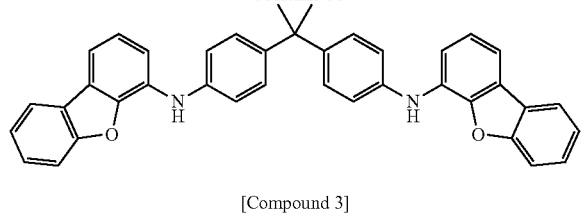

[Compound 3]

Compound 1 (11.3 g), Compound 2 (24.7 g), tris(dibenzylideneacetone)dipalladium (Pd$_2$(dba)$_3$, 2.75 g), 2,2'-bis(diphenylphosphino)-1,1''-binaphthalene (BINAP, 5.60 g) and sodium tert-butoxide (9.61 g) were placed in a round flask, and dissolved by introducing toluene (500 mL) thereto, and then the result was stirred for 2 hours at 80° C. The result was cooled to room temperature, then passed through a celite pad, and extracted with ethyl acetate in a separatory funnel, and the solvent was removed using a rotary evaporator. 19.5 g (yield: 70%) of Compound 3 was obtained through column chromatography. A Mass graph of Compound 3 is shown in FIG. 2.

Preparation Example 2

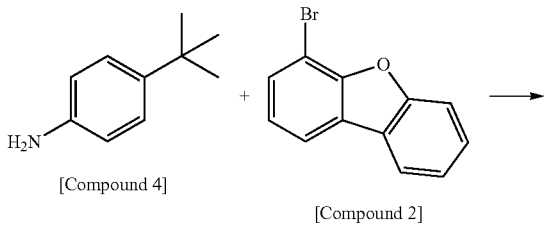

[Compound 4]  [Compound 2]

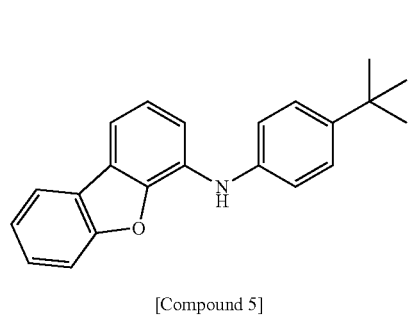

[Compound 5]

Compound 4 (6.0 g), Compound 2 (5.0 g), Pd$_2$(dba)$_3$ (915 mg), BINAP (1.87 g) and sodium tert-butoxide (2.88 g) were placed in a round flask, and dissolved by introducing toluene (50 mL) thereto, and then the result was stirred for 2 hours at 80° C. The result was cooled to room temperature, then passed through a celite pad, and extracted with ethyl acetate in a separatory funnel, and the solvent was removed using a rotary evaporator. 5.17 g (yield: 82%) of Compound 5 was obtained through column chromatography. A Mass graph of Compound 5 is shown in FIG. 3.

Preparation Example 3

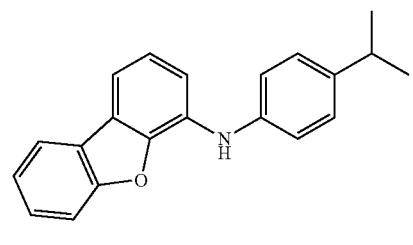

[Compound 6]  [Compound 2]

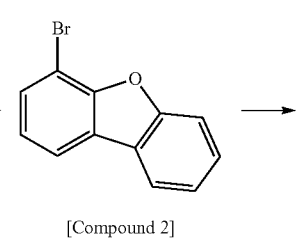

[Compound 7]

Compound 7 (3.7 g, 62%) was obtained in the same manner as in the method of Preparation Example 2 except that Compound 6 (5.4 g) was used instead of Compound 4. A Mass graph of Compound 7 is shown in FIG. 4.

Preparation Example 4

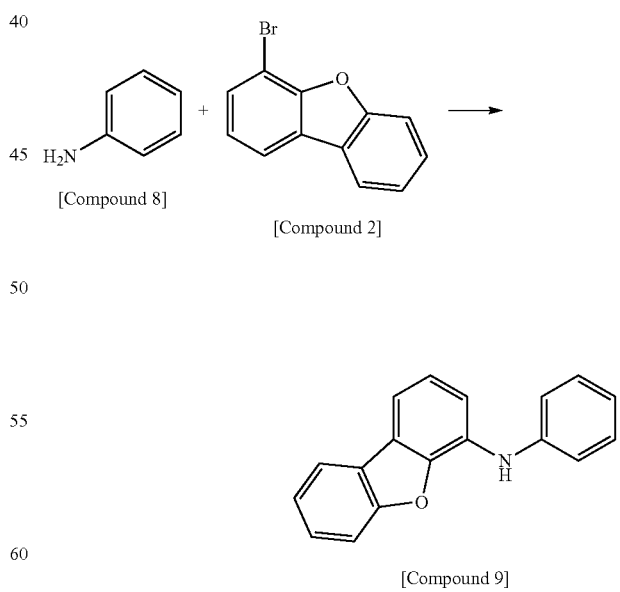

[Compound 8]  [Compound 2]

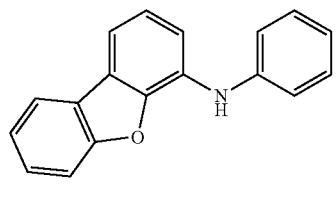

[Compound 9]

Compound 9 (3.57 g, 69%) was obtained in the same manner as in the method of Preparation Example 2 except that Compound 8 (3.73 g) was used instead of Compound 4. A Mass graph of Compound 9 is shown in FIG. 5.

Preparation Example 5

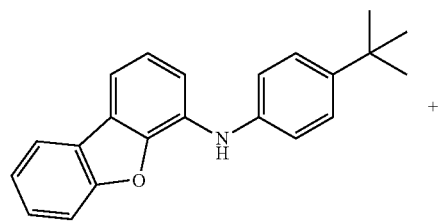

[Compound 5]

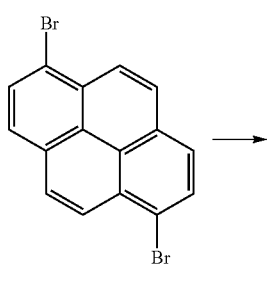

[Compound 10]

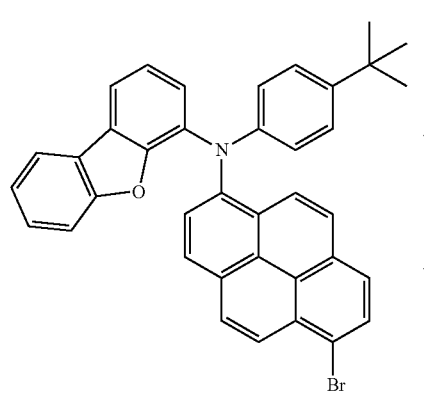

[Compound 11]

Compound 5 (3.15 g), Compound 10 (10.8 g), Pd$_2$(dba)$_3$ (1.37 g), P(tBu)$_3$ (910 mg) and sodium tert-butoxide (2.88 g) were placed in a round flask, and dissolved by introducing toluene (100 mL) thereto, and then the result was stirred for 30 minutes at 80° C. The result was cooled to room temperature, then passed through a celite pad, and extracted with ethyl acetate in a separatory funnel, and the solvent was removed using a rotary evaporator. 1.90 g (yield: 32%) of Compound 11 was obtained through column chromatography. A Mass graph of Compound 11 is shown in FIG. 6.

Preparation Example 6

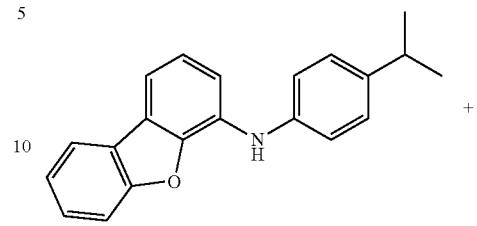

[Compound 7]

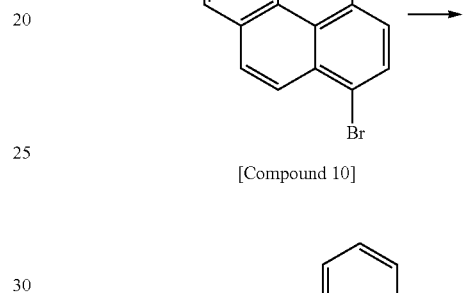

[Compound 10]

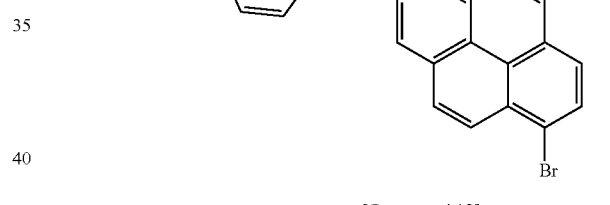

[Compound 12]

Compound 12 (1.45 g, 25%) was obtained in the same manner as in the method of Preparation Example 5 except that Compound 7 (3.01 g) was used instead of Compound 5. A Mass graph of Compound 12 is shown in FIG. 7.

Preparation Example 7

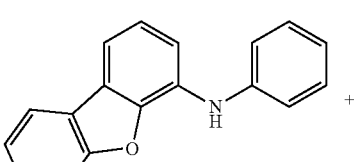

[Compound 9]

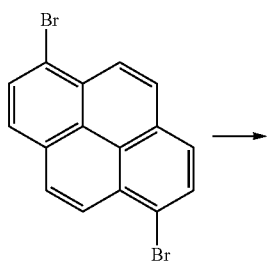
[Compound 10]
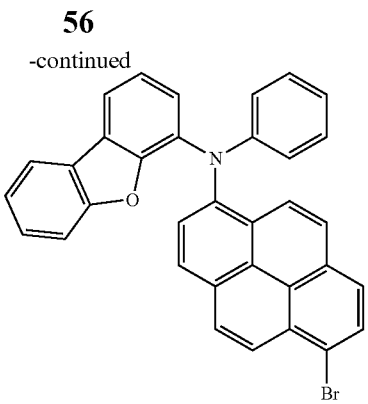
[Compound 13]
Compound 13 (1.99 g, 37%) was obtained in the same manner as in the method of Preparation Example 5 except that Compound 9 (2.59 g) was used instead of Compound 5. A Mass graph of Compound 13 is shown in FIG. 8.
Preparation Example 1-1
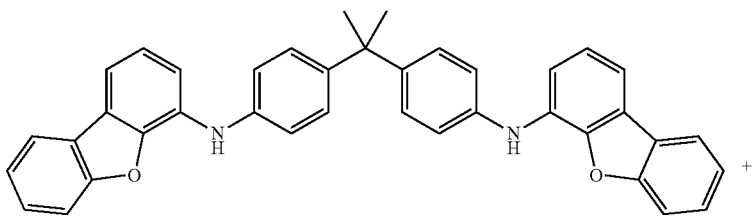
[Compound 3]
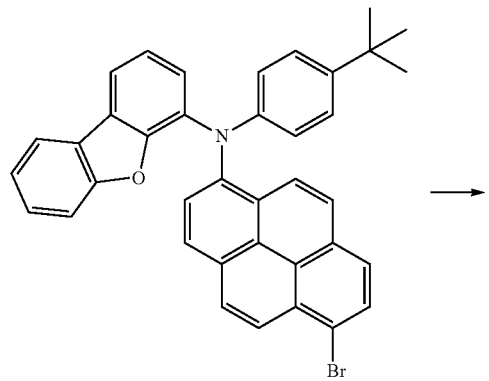
[Compound 11]

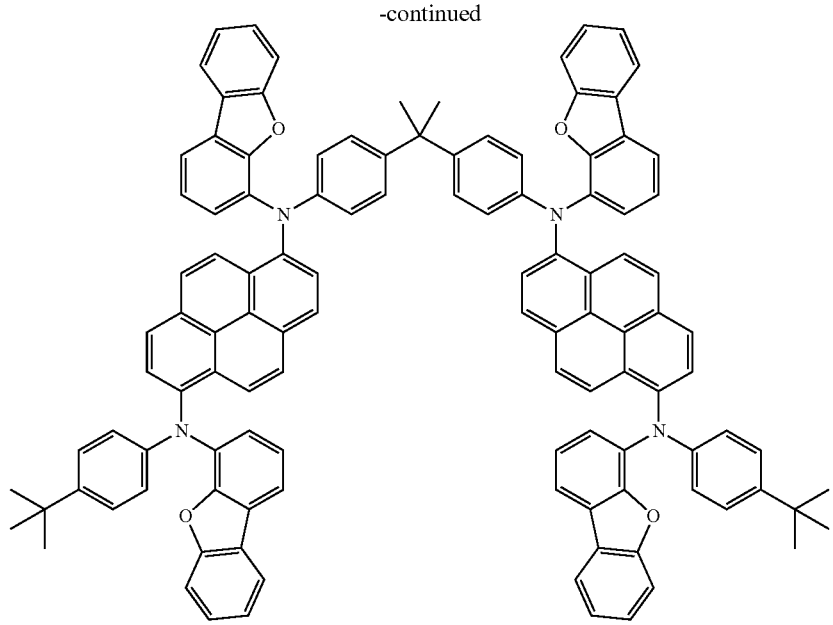

[Compound 14]

Compound 3 (2.23 g), Compound 11 (5.95 g), Pd$_2$(dba)$_3$ (366 mg), P(tBu)$_3$ (243 mg) and sodium tert-butoxide (1.15 g) were placed in a round flask, and dissolved by introducing toluene (20 mL) thereto, and then the result was stirred for 30 minutes at 80° C. The result was cooled to room temperature, then passed through a celite pad, and extracted with ethyl acetate in a separatory funnel, and the solvent was removed using a rotary evaporator. 2.66 g (yield: 42%) of Compound 14 was obtained through column chromatography. A Mass graph of Compound 14 is shown in FIG. 9.

Preparation Example 1-2

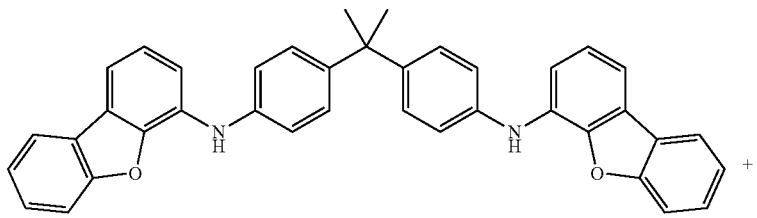

[Compound 3]

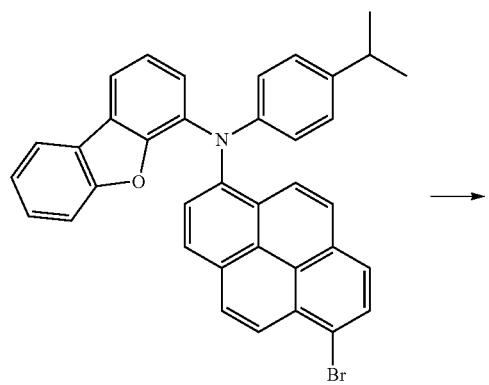

[Compound 12]

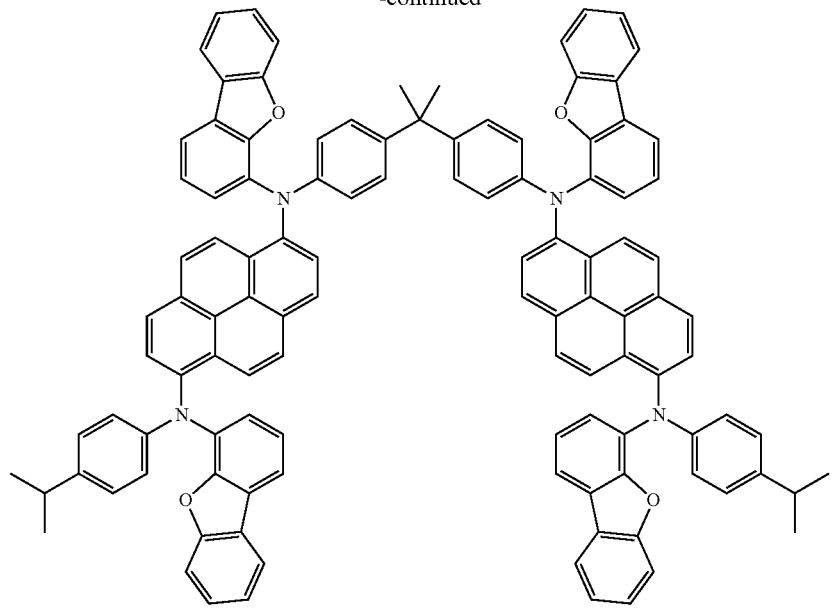

[Compound 15]

Compound 15 (2.43 g, 39%) was obtained in the same manner as in the method of Preparation Example 1-1 except that Compound 12 (5.80 g) was used instead of Compound 11. A Mass graph of Compound 15 is shown in FIG. 10.

Preparation Example 1-3

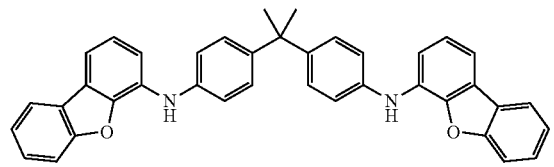

[Compound 3]

+

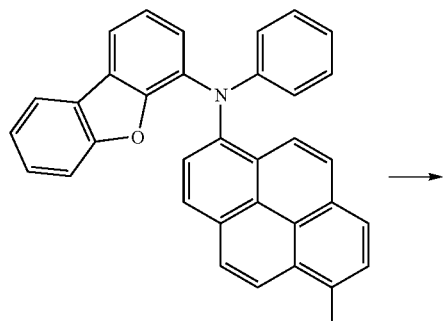

[Compound 13]

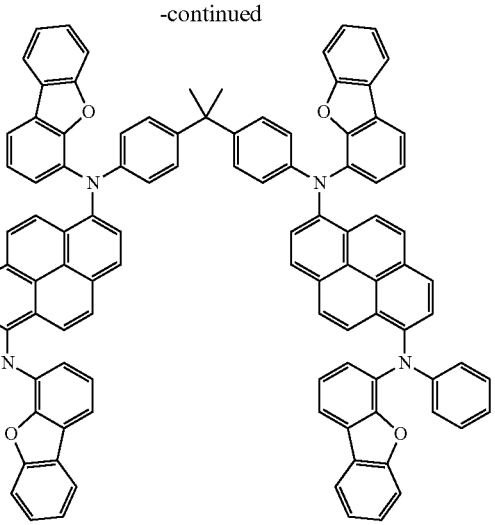

[Compound 16]

Compound 16 (2.71 g, 46%) was obtained in the same manner as in the method of Preparation Example 1-1 except that Compound 13 (5.38 g) was used instead of Compound 11. A Mass graph of Compound 16 is shown in FIG. 11.

Preparation Example 2-1

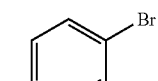

[Compound 22]

+

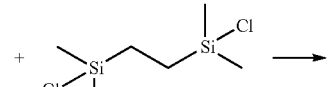

[Compound 23]

61

-continued

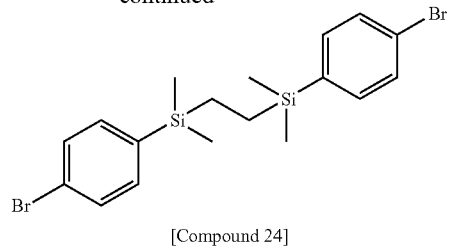

[Compound 24]

After dissolving Compound 22 (23.6 g) in THF (1000 ml), nBuLi (40 ml, 2.5 M in hexane) was added thereto at −78° C., and the result was stirred for 30 minutes, and then stirred for 1 hour at room temperature. Compound 23 (10 g) was added thereto, and the result was stirred for 2 hours. An ammonium chloride solution (200 ml) and water (200 ml) were added thereto, the result was stirred for 10 minutes, and after extracting the result with methylene chloride in a separatory funnel, the solvent was removed using a rotary evaporator. 27.9 g (yield: 61%) of Compound 24 was obtained through column chromatography. A Mass graph of Compound 24 is shown in FIG. 12.

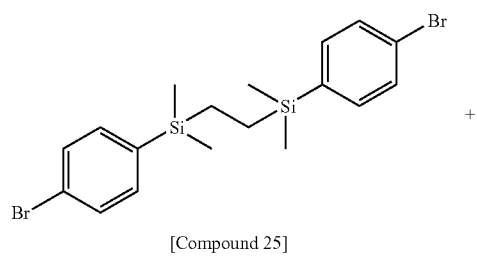 +

[Compound 25]

62

-continued

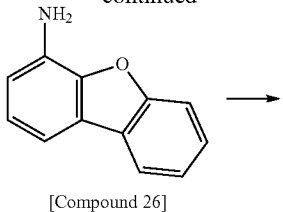

[Compound 26]

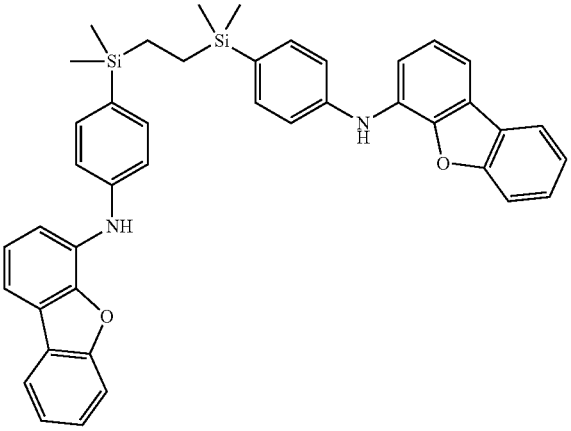

[Compound 27]

Compound 25 (6.6 g), Compound 26 (5.3 g), $Pd_2(dba)_3$ (662 mg), BINAP (1.35 g) and sodium tert-butoxide (2.09 g) were placed in a round flask, and dissolved by introducing toluene (75 mL) thereto, and then the result was stirred for 2 hours at 80° C. The result was cooled to room temperature, then passed through a celite pad, and extracted with ethyl acetate in a separatory funnel, and the solvent was removed using a rotary evaporator. 4.8 g (yield: 50%) of Compound 27 was obtained through column chromatography. A Mass graph of Compound 27 is shown in FIG. 13.

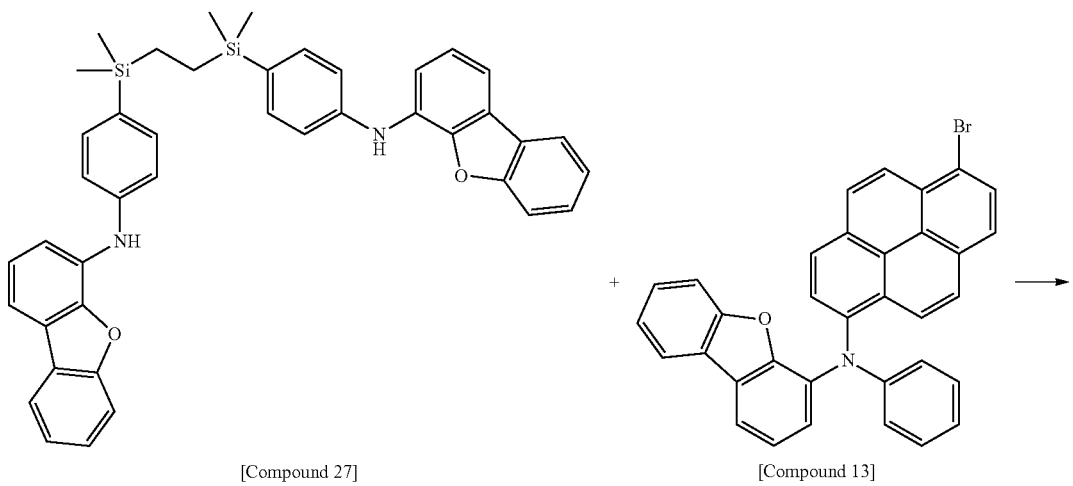

[Compound 27]                [Compound 13]

-continued
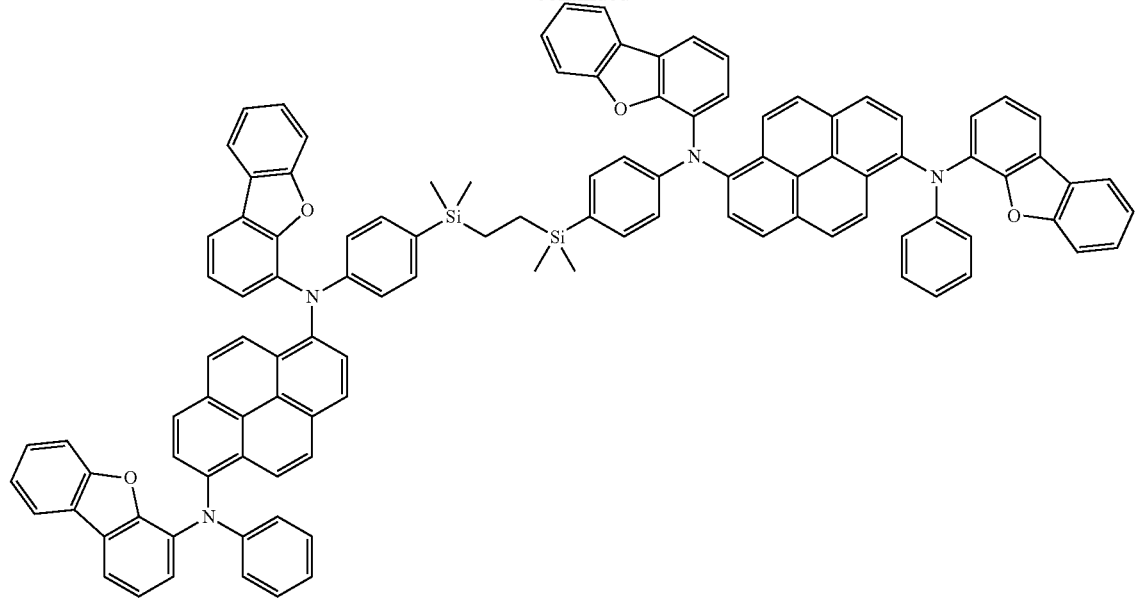
[Compound 28]
Compound 28 (1.85 g, 29%) was obtained in the same manner as in the method of Preparation Example 1-3 except that Compound 27 (2.64 g) was used instead of Compound 3. A Mass graph of Compound 28 is shown in FIG. 14.
Preparation Example 3-1
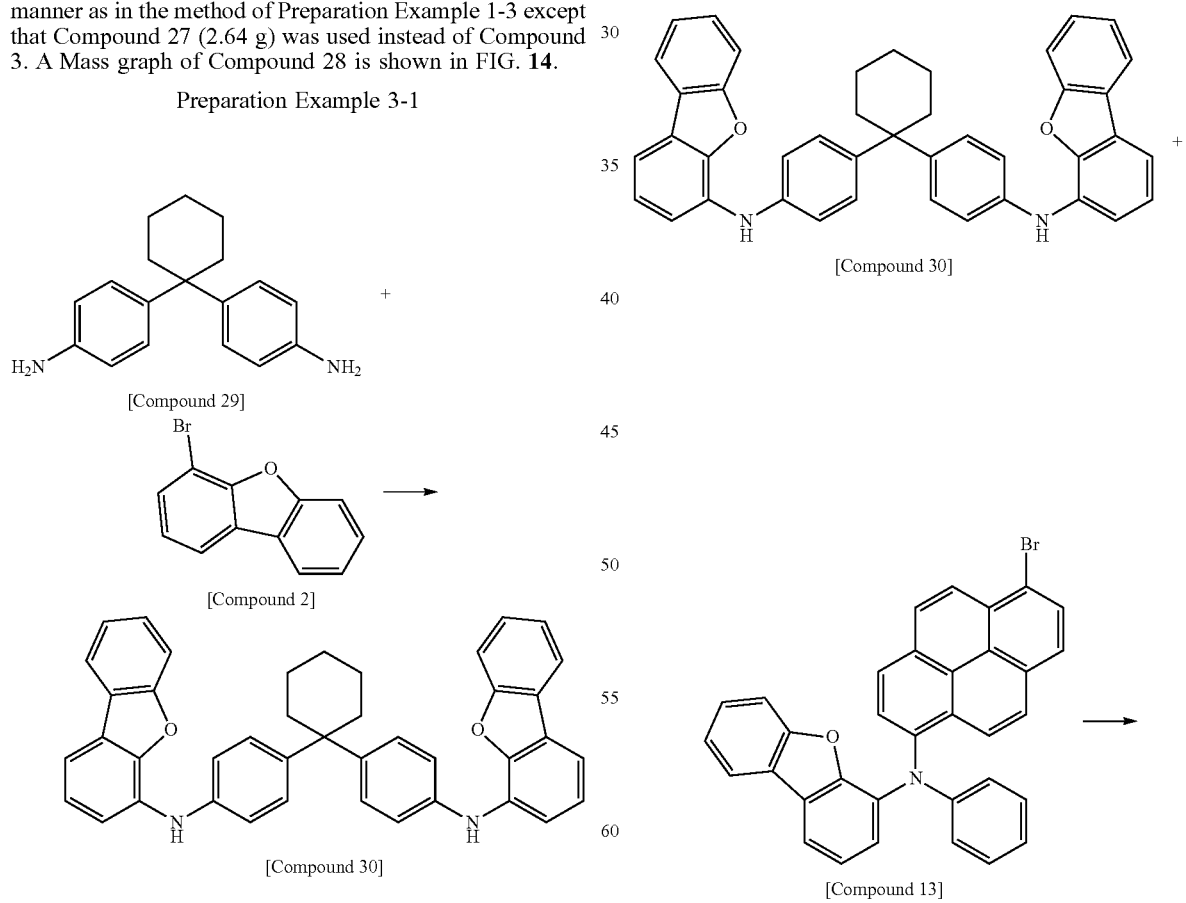
Compound 30 (18.5 g, 62%) was obtained in the same manner as in the method of Preparation Example 1 except that Compound 29 (13.3 g) was used instead of Compound 1. MS: [M+H]+=599

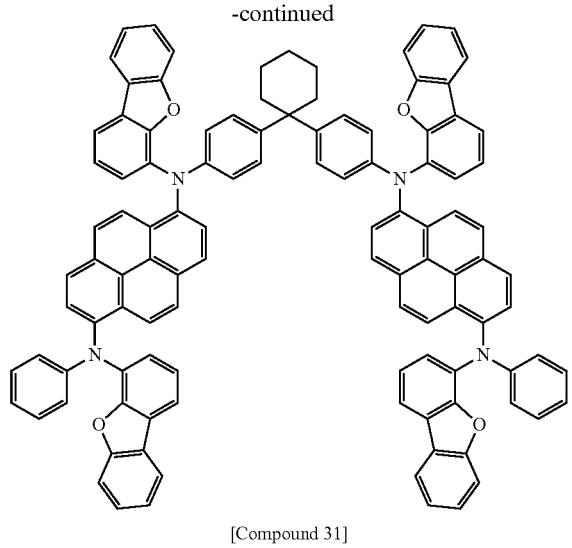

[Compound 31]

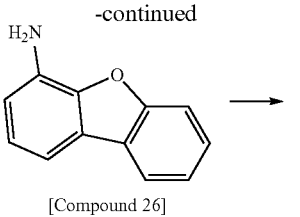

[Compound 26]

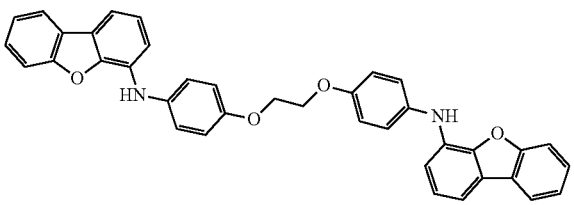

[Compound 33]

Compound 31 (2.11 g, 35%) was obtained in the same manner as in the method of Preparation Example 1-3 except that Compound 30 (2.4 g) was used instead of Compound 3. MS: [M+H]+=1514

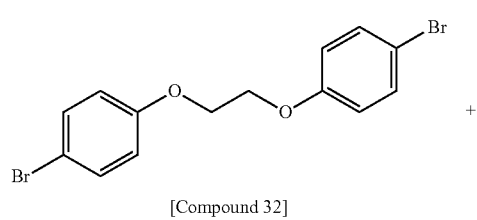

[Compound 32]

+

Compound 32 (3.72 g), Compound 26 (3.66 g), Pd$_2$(dba)$_3$ (916 mg), BINAP (1.87 g) and sodium tert-butoxide (2.88 g) were placed in a round flask, and dissolved by introducing toluene (100 mL) thereto, and then the result was stirred for 2 hours at 80° C. The result was cooled to room temperature, then passed through a celite pad, and extracted with ethyl acetate in a separatory funnel, and the solvent was removed using a rotary evaporator. 2.71 g (yield: 47%) of Compound 33 was obtained through column chromatography. MS: [M+H]+=577

[Compound 33]

+

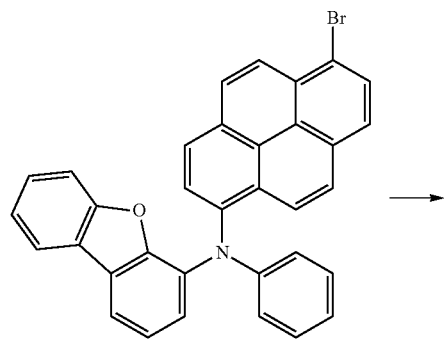

[Compound 13]

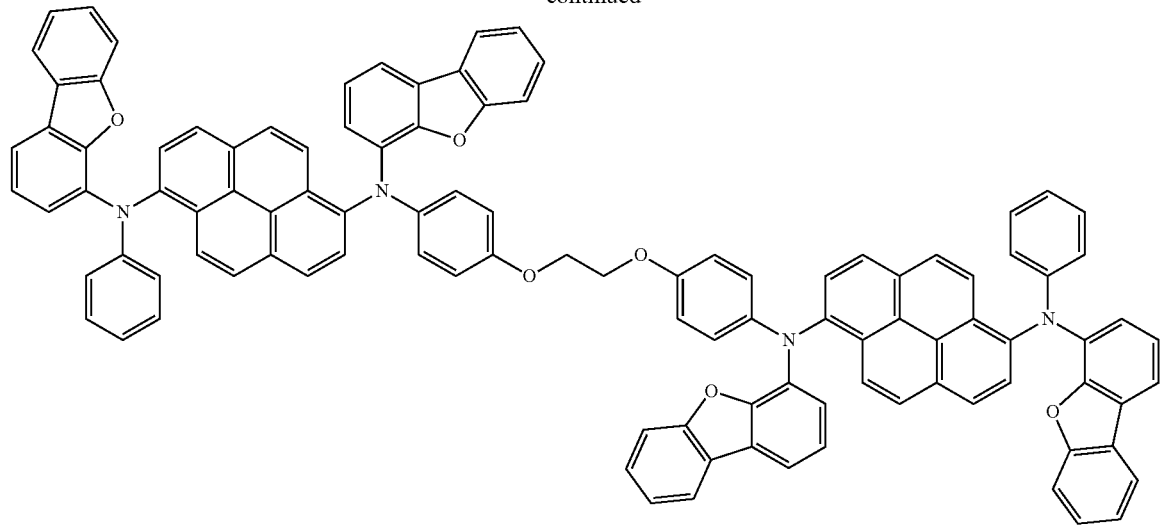

[Compound 34]

Compound 34 (2.15 g, 36%) was obtained in the same manner as in the method of Preparation Example 1-3 except that Compound 33 (2.30 g) was used instead of Compound 3. MS: [M+H]+=1492

Synthesis of Compound of Comparative Example 1

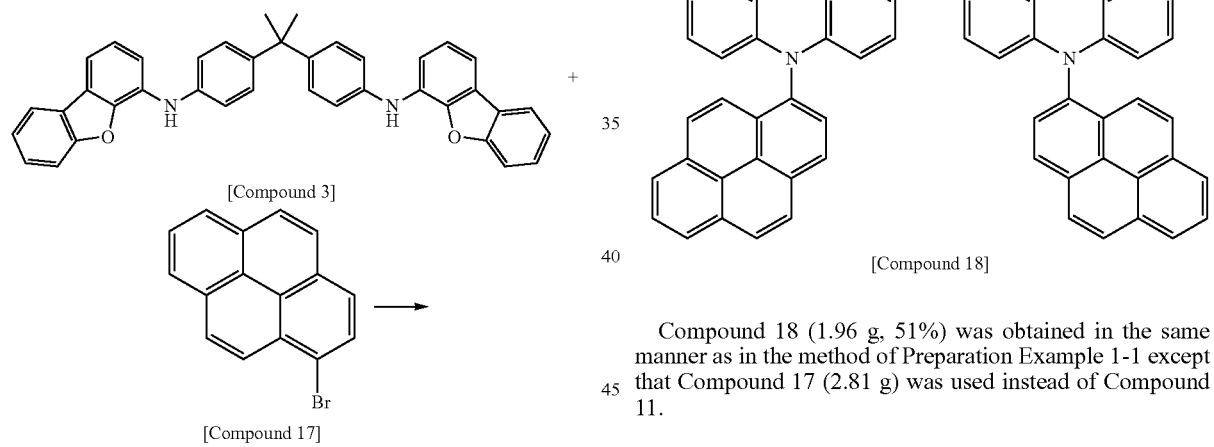

[Compound 18]

Compound 18 (1.96 g, 51%) was obtained in the same manner as in the method of Preparation Example 1-1 except that Compound 17 (2.81 g) was used instead of Compound 11.

Synthesis of Compound of Comparative Example 2

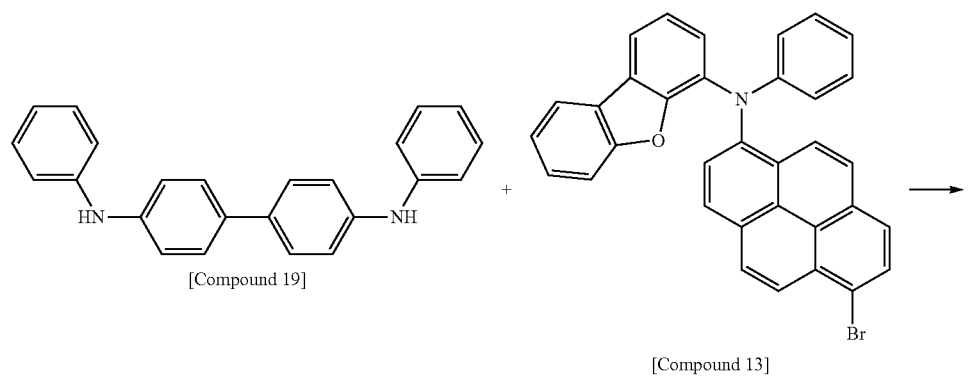

-continued

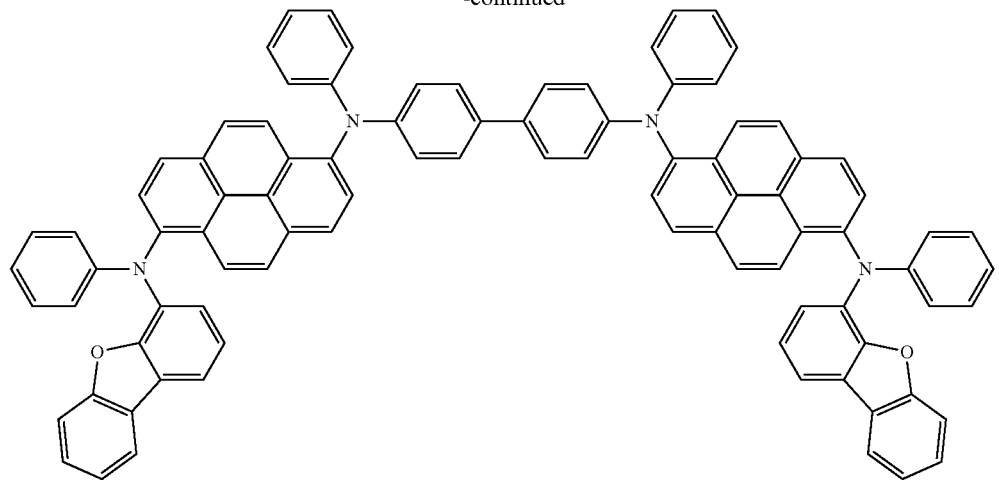

[Compound 20]

Compound 20 (1.90 g, 38%) was obtained in the same manner as in the method of Preparation Example 1-3 except that Compound 19 (1.35 g) was used instead of Compound 3.

Compound of Comparative Example 3

[Compound 21]

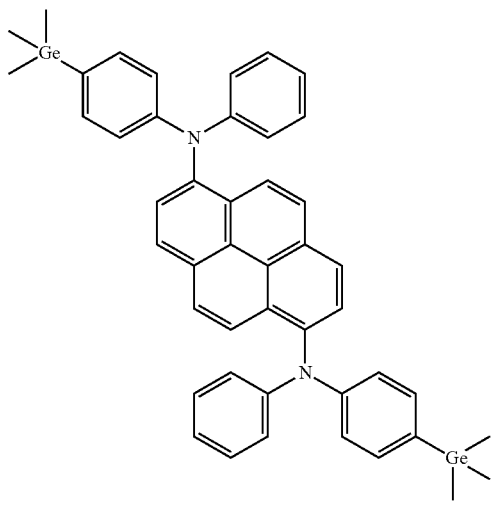

Example 1

A glass substrate on which indium tin oxide (ITO) was coated as a thin film to a thickness of 50 nm was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a 60 nm hole injection and transfer layer was formed by spin coating AI4083 (PEDOT/PSS polymer, CLEVIOS™ P VP AI 4083 of Heraeus Precious Metals GmbH & Co. KG) for 60 seconds at 1000 rpm, baking for 2 minutes at 80° C., and baking for 15 minutes at 120° C.

On the hole injection and transfer layer, a 0.5 wt % toluene solution prepared with poly(9,9-di-n-octylfluorenyl-2,7-diyl) (Sigma Aldrich) and Compound 14 of Preparation Example 1-1 in a weight ratio of 100:6 was 5000 rpm spin coated, baked for 2 minutes at 80° C., and baked for 30 minutes at 120° C. to form a light emitting layer having a thickness of 55 nm.

This was dried for 10 minutes at 130° C. under nitrogen gas atmosphere, and then lithium fluoride (LiF) was deposited to a film thickness of approximately 1 nm, and lastly, aluminum was deposited to a film thickness of 100 nm to form a cathode.

In the above-mentioned processes, the deposition rates of the lithium fluoride and the aluminum of the cathode were maintained at 0.3 Å/sec and 2 Å/sec, respectively, and the degree of vacuum during the deposition was maintained at $2 \times 10^{-7}$ to $5 \times 10^{-6}$ torr to manufacture an organic light emitting device.

Device structure: ITO (50 nm)/AI4083 (60 nm)/EML (55 nm)/LiF (1 nm)/Al (100 nm)

Example 2

An organic light emitting device was manufactured in the same manner as in Example 1 except that Compound 15 was used instead of Compound 14.

Example 3

An organic light emitting device was manufactured in the same manner as in Example 1 except that Compound 16 was used instead of Compound 14.

Example 4

An organic light emitting device was manufactured in the same manner as in Example 1 except that Compound 28 was used instead of Compound 14.

Example 5

An organic light emitting device was manufactured in the same manner as in Example 1 except that Compound 31 was used instead of Compound 14.

Example 6

An organic light emitting device was manufactured in the same manner as in Example 1 except that Compound 34 was used instead of Compound 14.

Comparative Example 1

An organic light emitting device was manufactured in the same manner as in Example 1 except that Compound 18 was used instead of Compound 14.

Comparative Example 2

An organic light emitting device was manufactured in the same manner as in Example 1 except that Compound 20 was used instead of Compound 14.

Comparative Example 3

An organic light emitting device was manufactured in the same manner as in Example 1 except that Compound 21 was used instead of Compound 14.

The invention claimed is:

1. A compound represented by the following Chemical Formula 1:

[Chemical Formula 1]

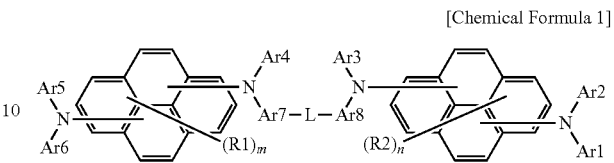

wherein, in Chemical Formula 1,

Ar1 to Ar6 are the same as or different from each other, and each independently a substituted or unsubstituted aryl group; or a substituted or unsubstituted heterocyclic group;

Ar7 and Ar8 are the same as or different from each other, and each independently a substituted or unsubstituted arylene group; or a substituted or unsubstituted divalent heterocyclic group;

R1 and R2 are the same as or different from each other, and each independently hydrogen; or a substituted or unsubstituted alkyl group;

m and n are the same as or different from each other, and each independently an integer of 0 to 8, and when m is 2 or greater, R1s are the same as or different from each other, and when n is 2 or greater, R2s are the same as or different from each other; and L is a substituted or unsubstituted alkylene group; a substituted or unsubstituted cycloalkylene group; or selected from among the following structural formulae, provided that when L is a substituted or unsubstituted cycloalkylene group, one of Ar1 or Ar2 is a substituted or unsubstituted dibenzofuran group, or a substituted or unsubstituted dibenzothiopehene group,

TABLE 1

| | Voltage (V) | Current Density (mA/cm$^2$) | Power Efficiency (Cd/A) | Light Emission Efficiency (lm/W) | Quantum Efficiency (%) | Luminance (Cd/m$^2$) | CIE x | CIE y | T80 (h) |
|---|---|---|---|---|---|---|---|---|---|
| Example 1 | 4.33 | 10.00 | 1.84 | 1.34 | 2.21 | 184.03 | 0.153 | 0.090 | 15.3 |
| Example 2 | 4.38 | 10.00 | 1.95 | 1.40 | 2.34 | 195.24 | 0.153 | 0.089 | 14.2 |
| Example 3 | 4.43 | 10.00 | 1.74 | 1.23 | 2.09 | 174.31 | 0.154 | 0.091 | 14.4 |
| Example 4 | 4.39 | 10.00 | 1.78 | 1.27 | 2.14 | 178.45 | 0.152 | 0.087 | 15.1 |
| Example 5 | 4.51 | 10.00 | 1.81 | 1.27 | 2.17 | 181.25 | 0.153 | 0.090 | 15.5 |
| Example 6 | 4.47 | 10.00 | 1.83 | 1.29 | 2.20 | 183.58 | 0.153 | 0.088 | 14.5 |
| Comparative Example 1 | 4.43 | 10.00 | 1.69 | 1.20 | 1.49 | 169.32 | 0.153 | 0.089 | 11.7 |
| Comparative Example 2 | 4.49 | 10.00 | 1.79 | 1.25 | 1.35 | 179.20 | 0.164 | 0.160 | 13.5 |
| Comparative Example 3 | 4.50 | 10.00 | 1.75 | 1.22 | 1.30 | 170.78 | 0.156 | 0.096 | 8.2 |

It was seen that, when using the compound according to the present specification as a blue dopant in the organic light emitting device, performance was superior in terms of voltage; efficiency; and lifetime, and particularly, the compound of the subject disclosure was superior compared to the compounds of the comparative examples in terms of a lifetime.

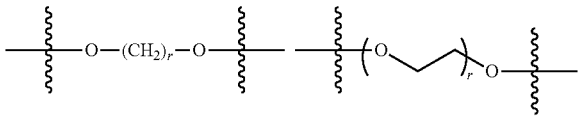

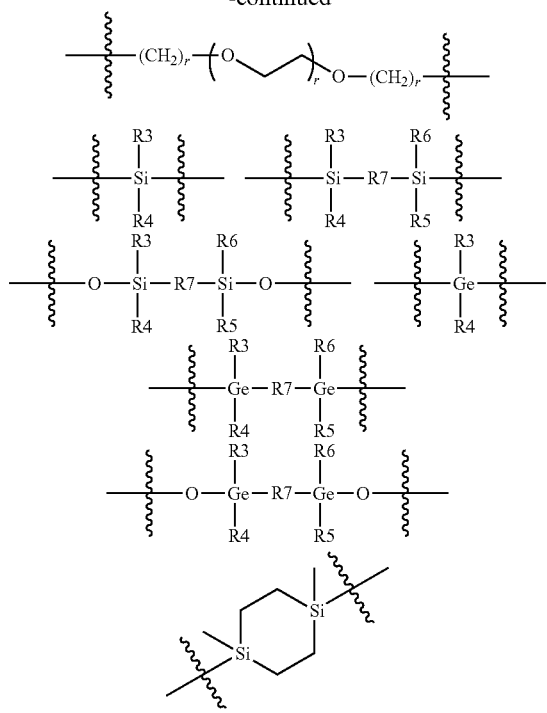

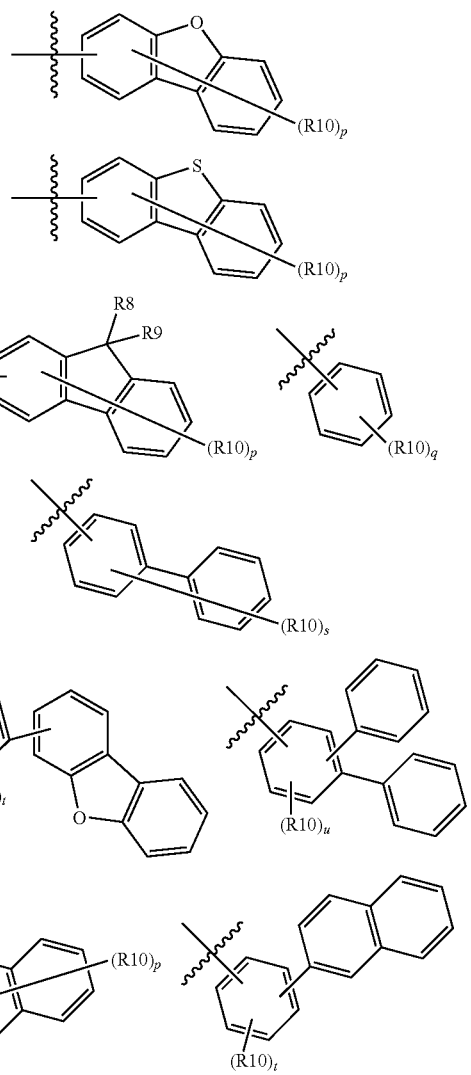

in the structural formulae, r is an integer of 1 to 20;

R3 to R6 are the same as or different from each other, and each independently a substituted or unsubstituted alkyl group; or a substituted or unsubstituted aryl group;

R7 is a direct bond; a substituted or unsubstituted alkylene group; a substituted or unsubstituted cycloalkylene group; or a substituted or unsubstituted arylene group; and

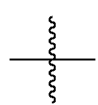

means a site bonding to Ar7 and Ar8.

2. The compound of claim 1, wherein Ar1 to Ar6 are the same as or different from each other, and each independently a substituted or unsubstituted phenyl group; a substituted or unsubstituted biphenyl group; a substituted or unsubstituted naphthyl group; a substituted or unsubstituted dibenzofuran group; a substituted or unsubstituted dibenzothiophene group; or a substituted or unsubstituted fluorene group; and Ar7 and Ar8 are the same as or different from each other, and each independently a substituted or unsubstituted phenylene group; a substituted or unsubstituted biphenylylene group; a substituted or unsubstituted divalent naphthalene group; a substituted or unsubstituted divalent dibenzofuran group; a substituted or unsubstituted divalent dibenzothiophene group; or a substituted or unsubstituted divalent fluorene group.

3. The compound of claim 1, wherein Ar1 to Ar6 are the same as or different from each other, and each independently selected from among the following structural formulae, in the structural formulae, R8 and R9 are the same as or different from each other, and each independently a substituted or unsubstituted alkyl group; or a substituted or unsubstituted aryl group;

R10 is hydrogen; deuterium; a halogen group; a cyano group; a substituted or unsubstituted alkyl group; a substituted or unsubstituted fluoroalkyl group; a substituted or unsubstituted silyl group; a substituted or unsubstituted aryl group; or a substituted or unsubstituted cycloalkyl group;

p is an integer of 1 to 7, q is an integer of 1 to 5, s is an integer of 1 to 9, t is an integer of 1 to 4, u is an integer of 1 to 3, and when p, q, s, t and u are 2 or greater, R10s are the same as or different from each other;

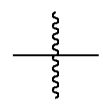

means a site bonding to N of Chemical Formula 1.

4. The compound of claim 3, wherein R10 is hydrogen; deuterium; a methyl group; an ethyl group; an isopropyl group; a tert-butyl group; a 2-ethylhexyl group; a trimethylsilyl group; a triphenylsilyl group; a tert-butyldimethylsilyl group; a cyclopropyl group; a cyclobutyl group; a cyclopentyl group; a cyclohexyl group; fluorine; a cyano group; or a trifluoromethyl group.

5. The compound of claim 3, wherein R8 and R9 are the same as or different from each other, and each independently an alkyl group having 1 to 20 carbon atoms.

6. The compound of claim 1, wherein R1 and R2 are hydrogen.

7. The compound of claim 1, wherein Ar2 to Ar5 are the same as each other, Ar1 and Ar6 are the same as each other, and Ar7 and Ar8 are the same as each other.

8. The compound of claim 1, wherein one of Ar1 or Ar2 is a substituted or unsubstituted dibenzofuran group; a substituted or unsubstituted dibenzothiophene group; or a substituted or unsubstituted fluorene group; and the other is a substituted or unsubstituted phenyl group; or a substituted or unsubstituted naphthyl group.

9. The compound of claim 1, wherein Chemical Formula 1 is represented by any one of the following structural formulae:

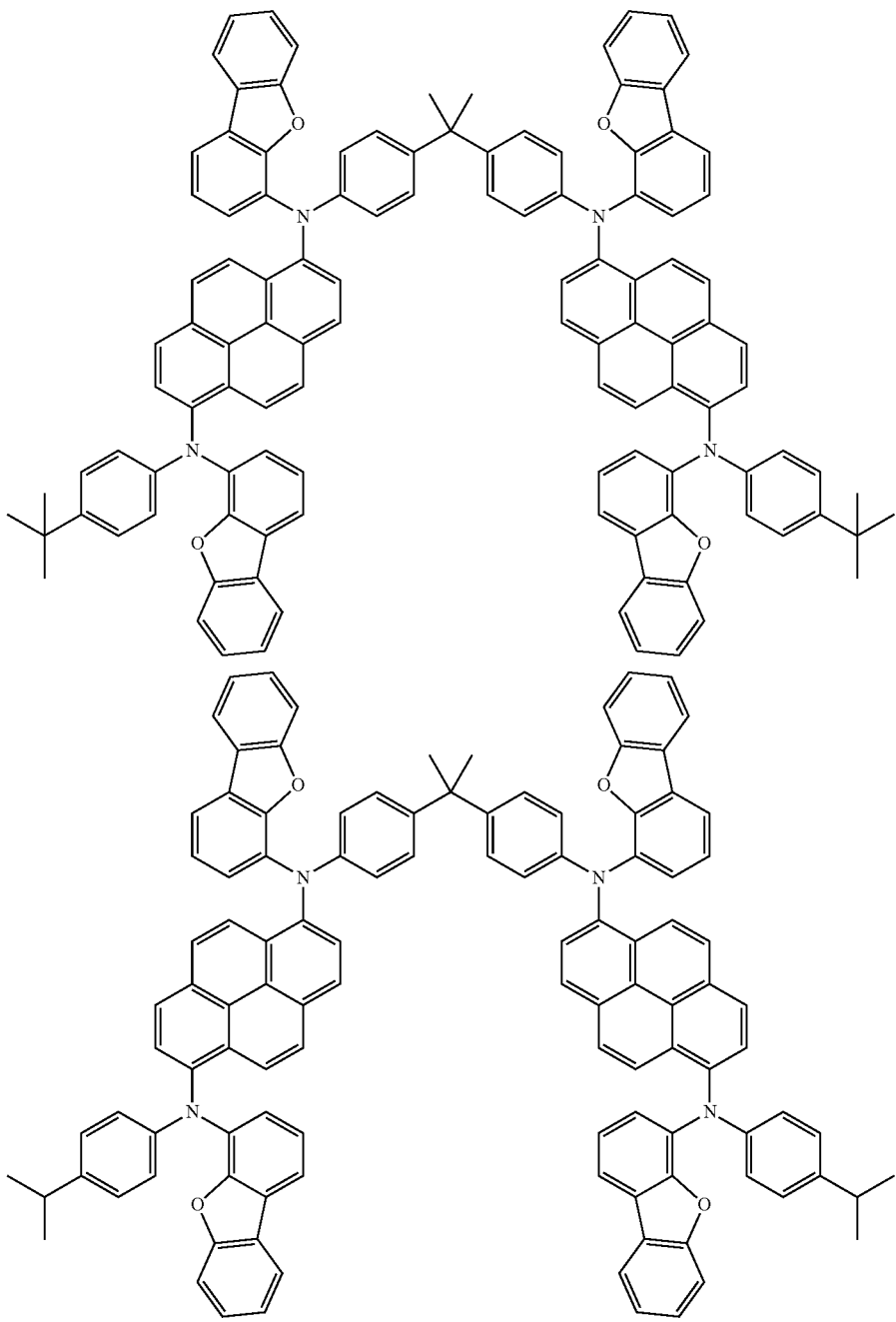

-continued
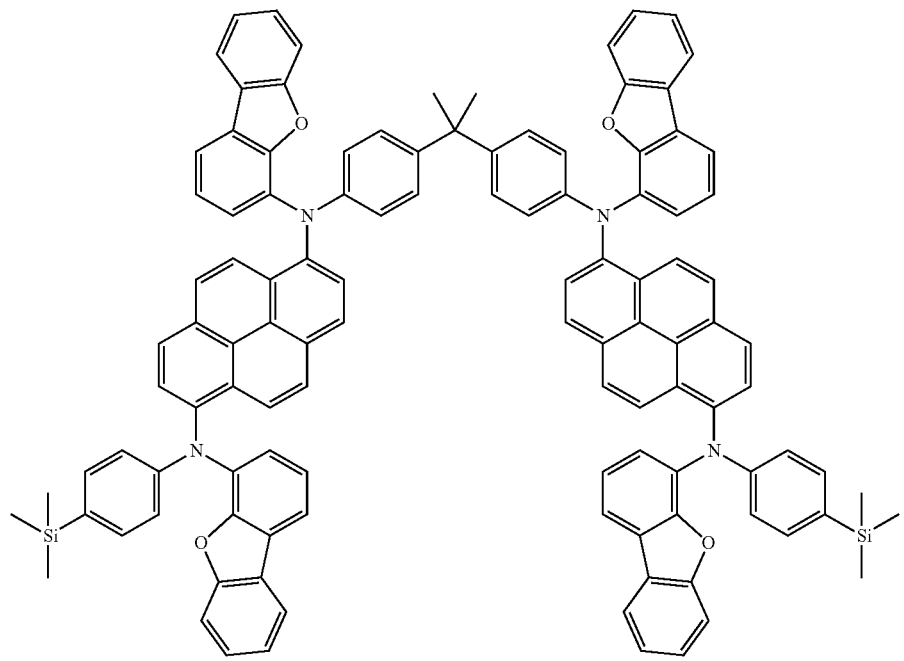
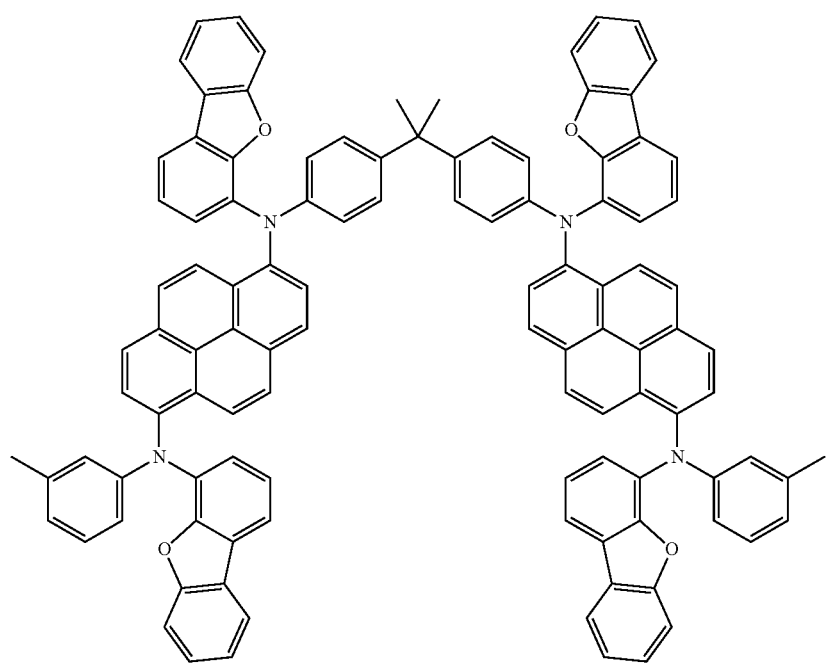

-continued
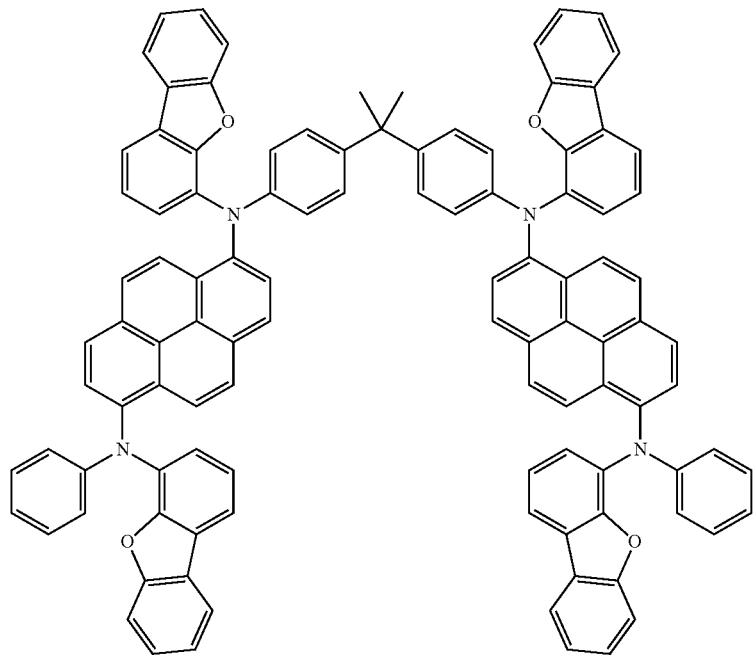
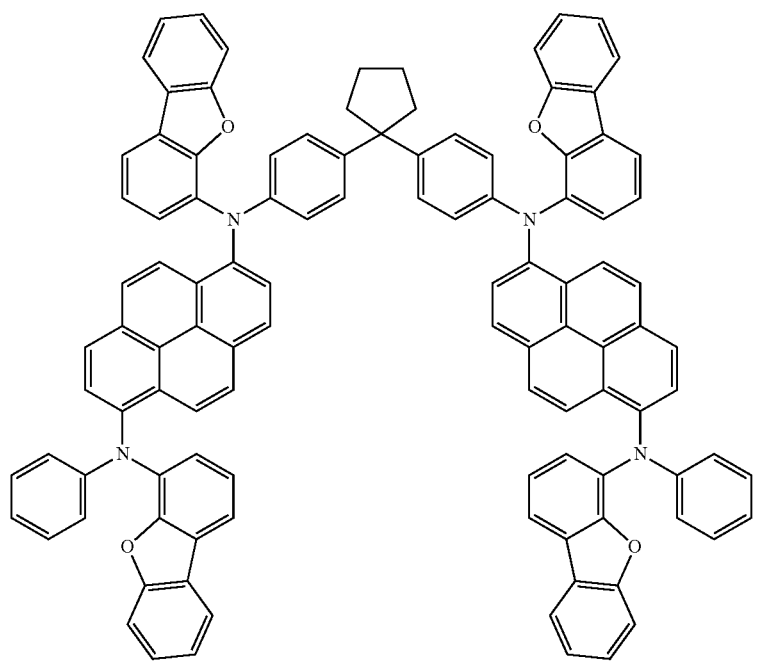

81
-continued
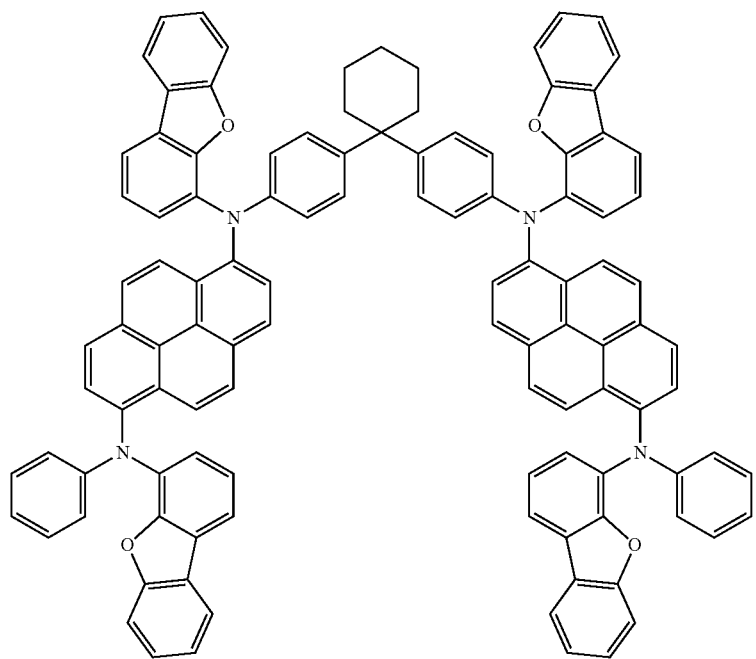
82
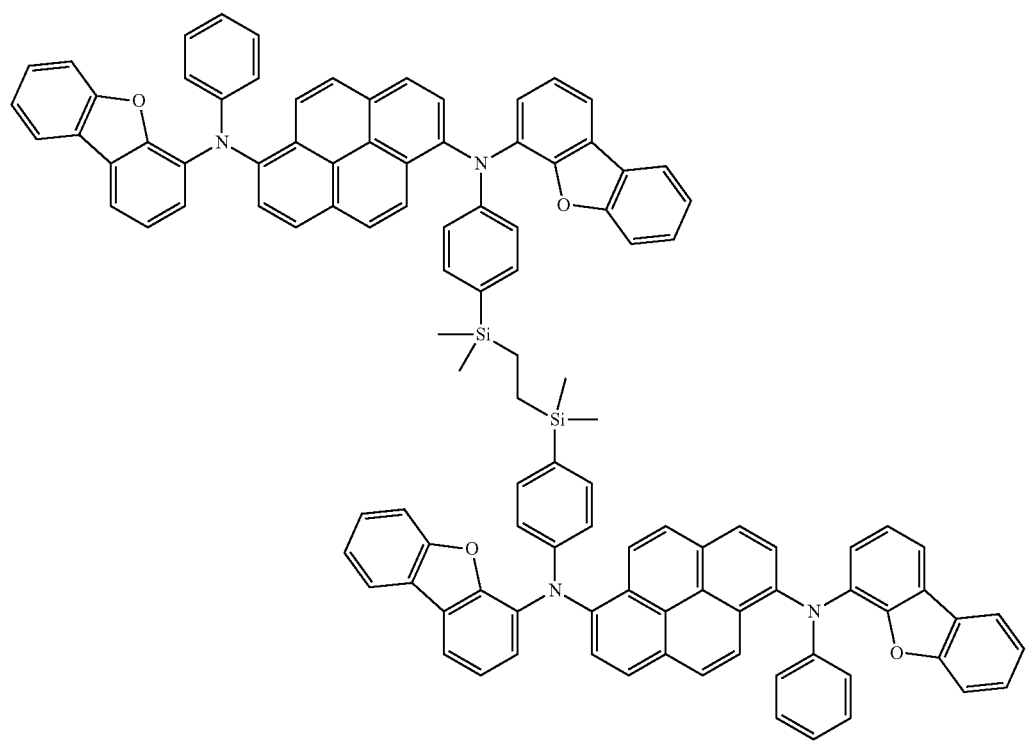

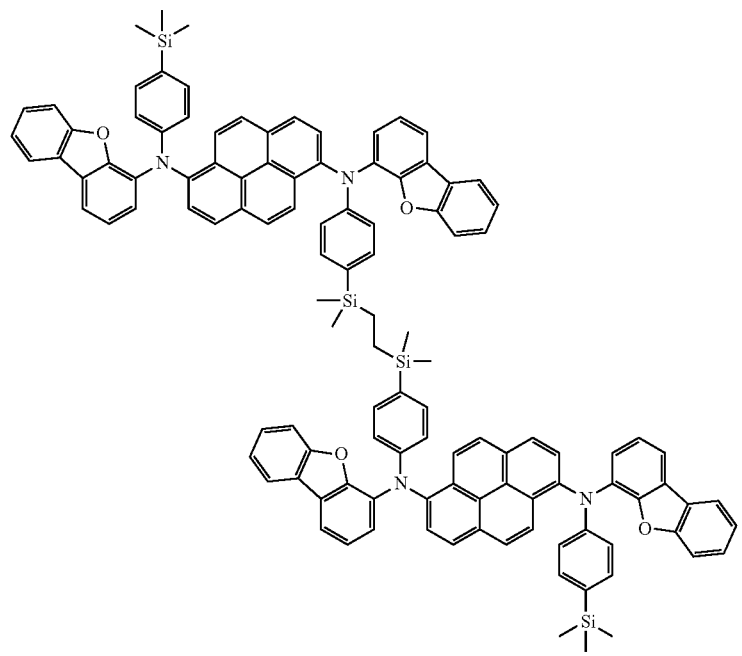 [SMILES: C[Si](C)(C)c1ccc(N(c2ccc3ccc4c(N(c5ccc([Si](C)(C)CC[Si](C)(C)c6ccc(N(c7ccc8ccc9c(N(c%10ccc([Si](C)(C)C)cc%10)c%10cccc%11c%10oc%10ccccc%10%11)ccc%10ccc7c8c%109)c7cccc8c7oc7ccccc78)cc6)cc5)c5cccc6c5oc5ccccc56)ccc5ccc2c3c54)c2cccc3c2oc2ccccc23)cc1]
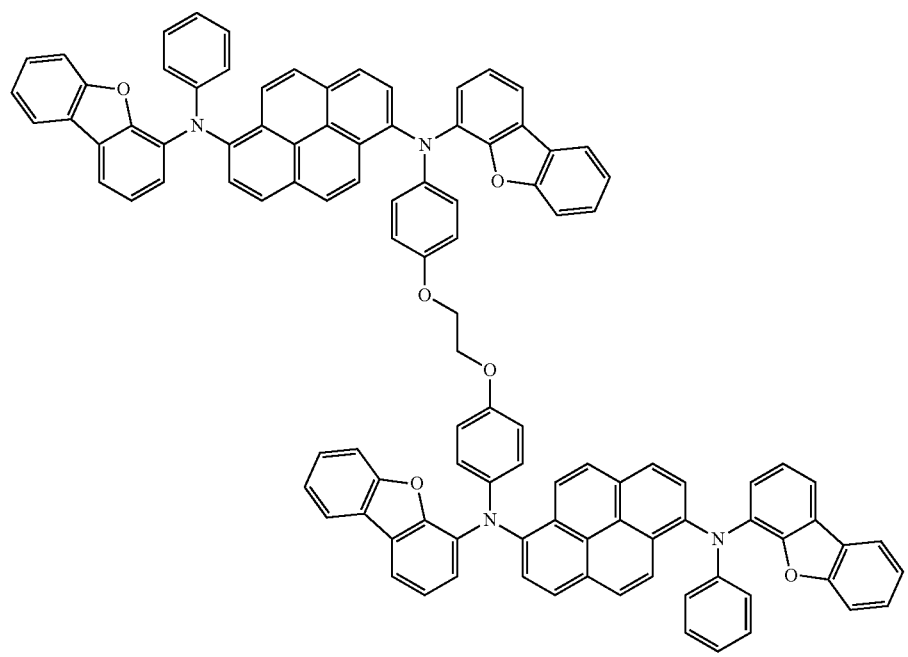

-continued
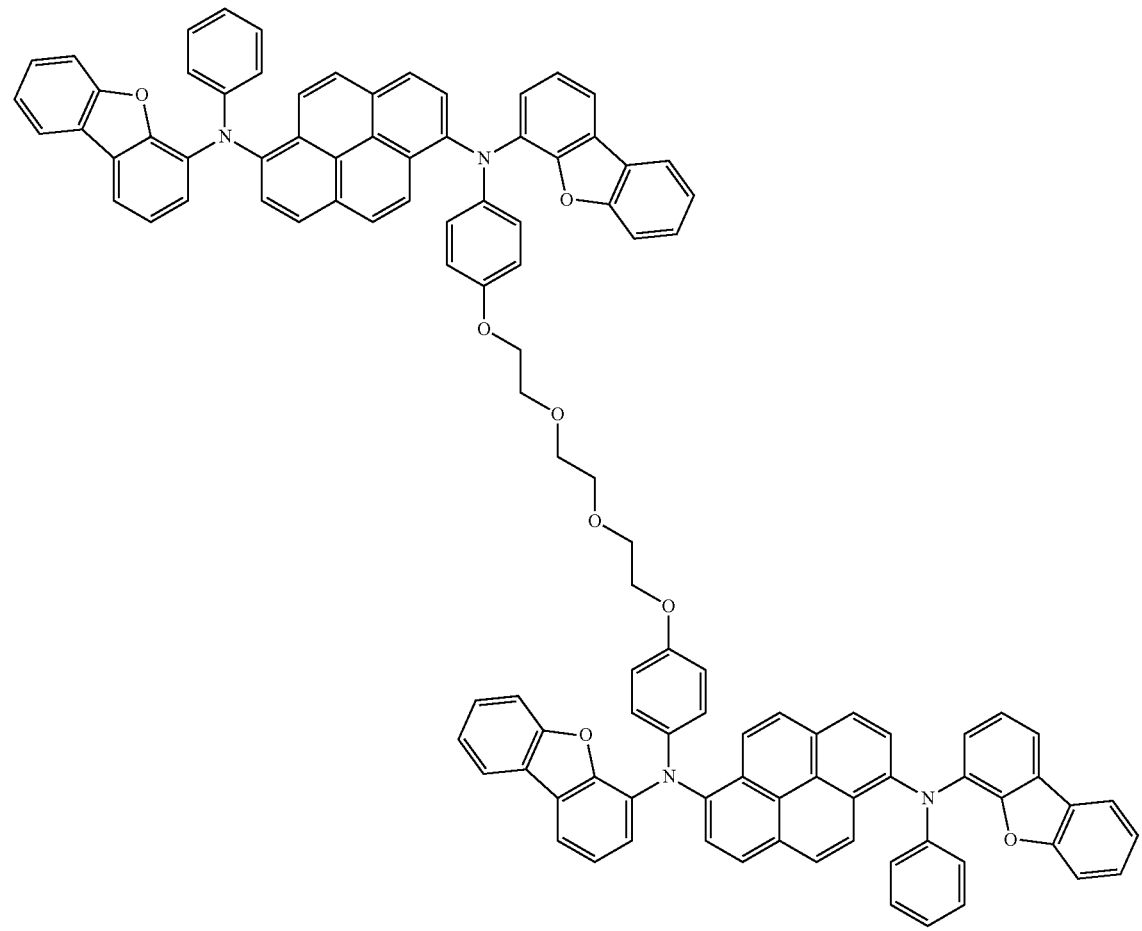
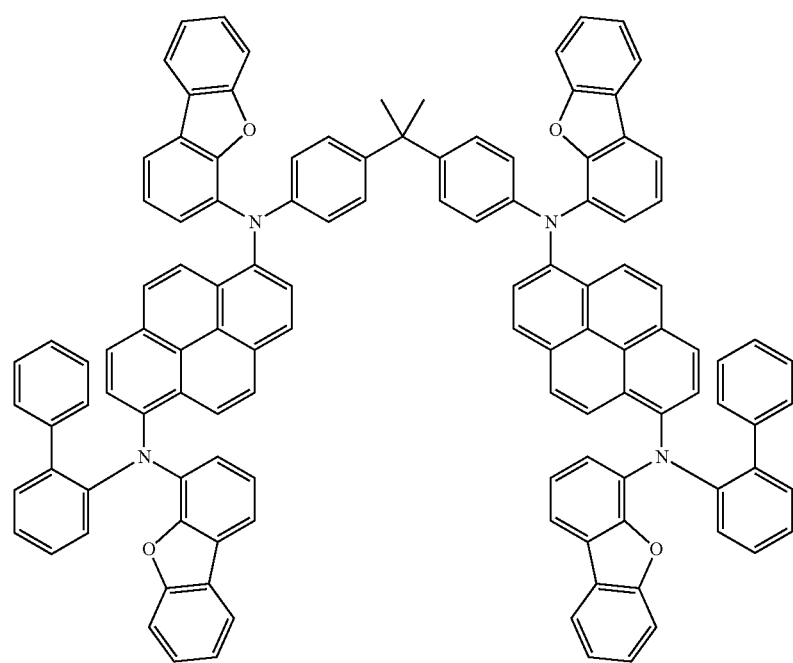

-continued
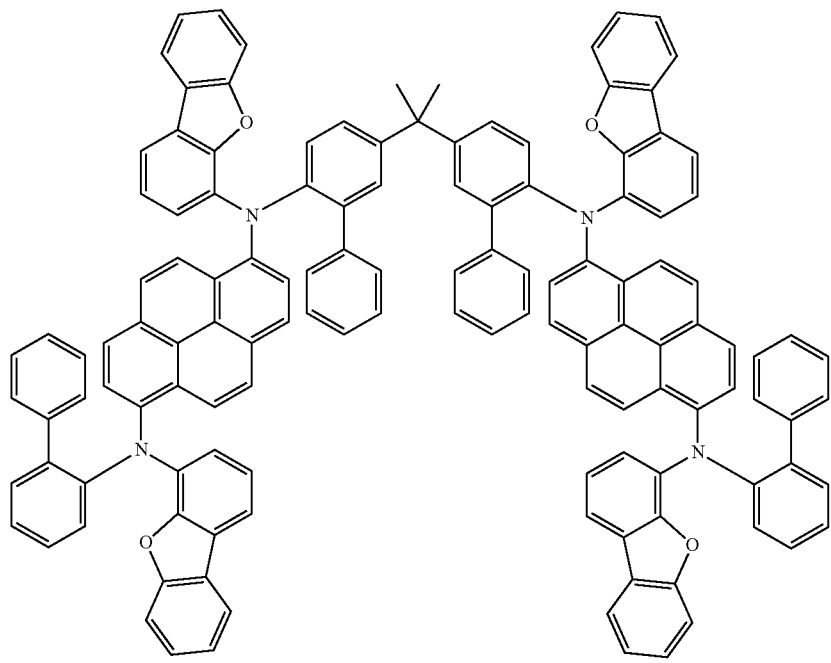
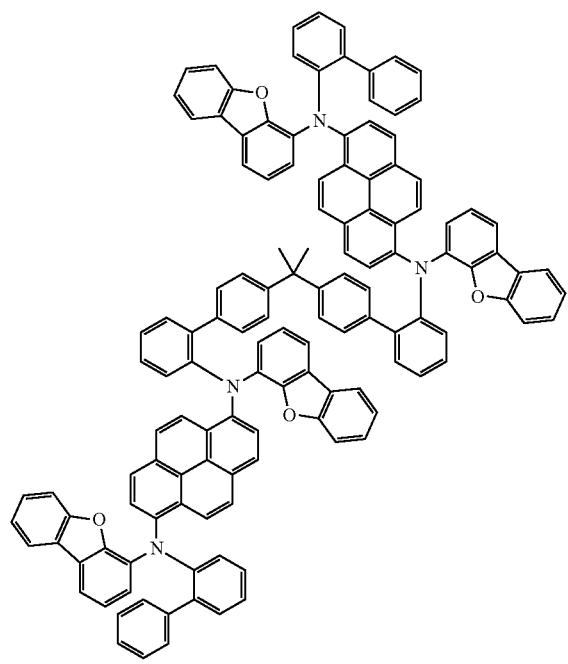

-continued
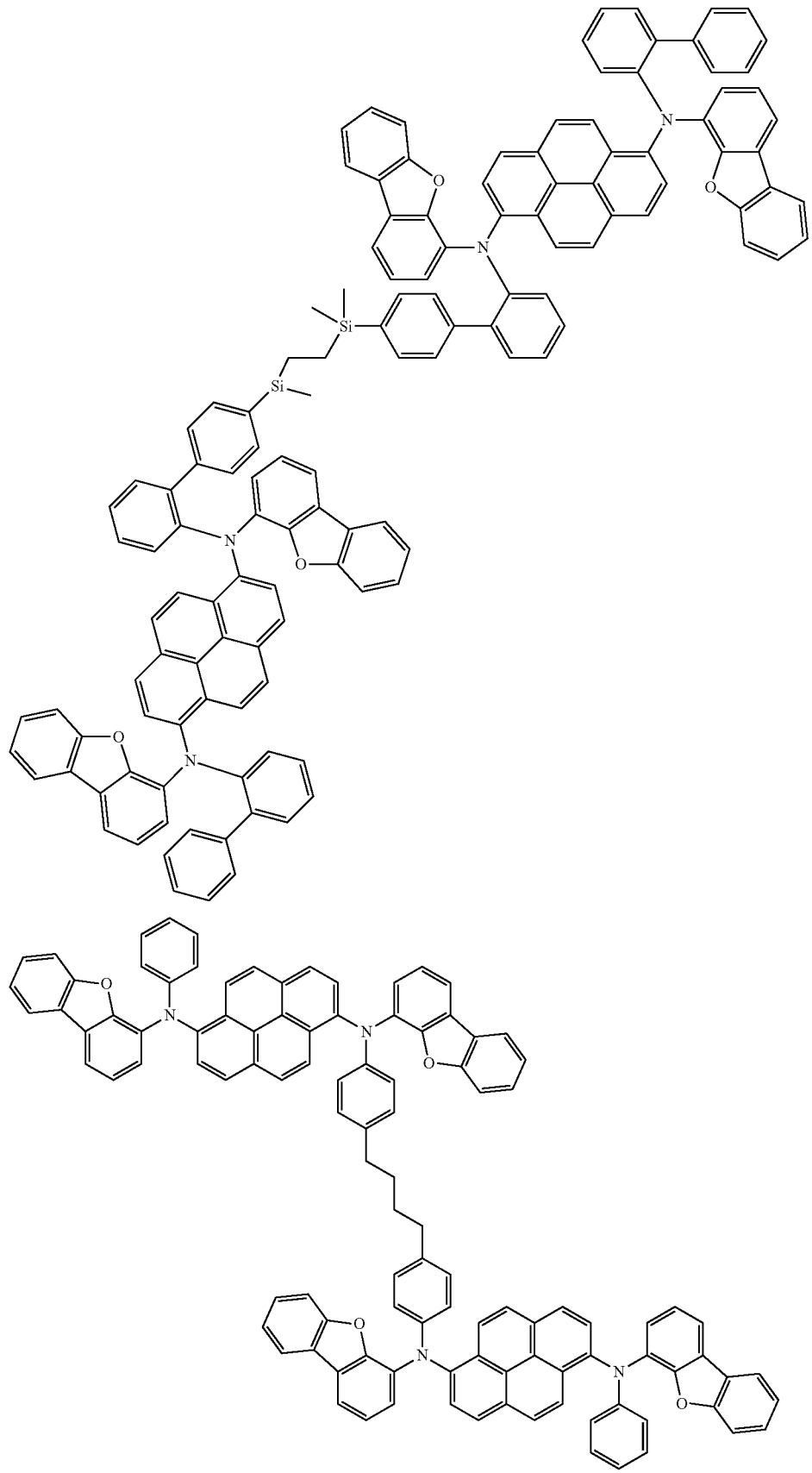

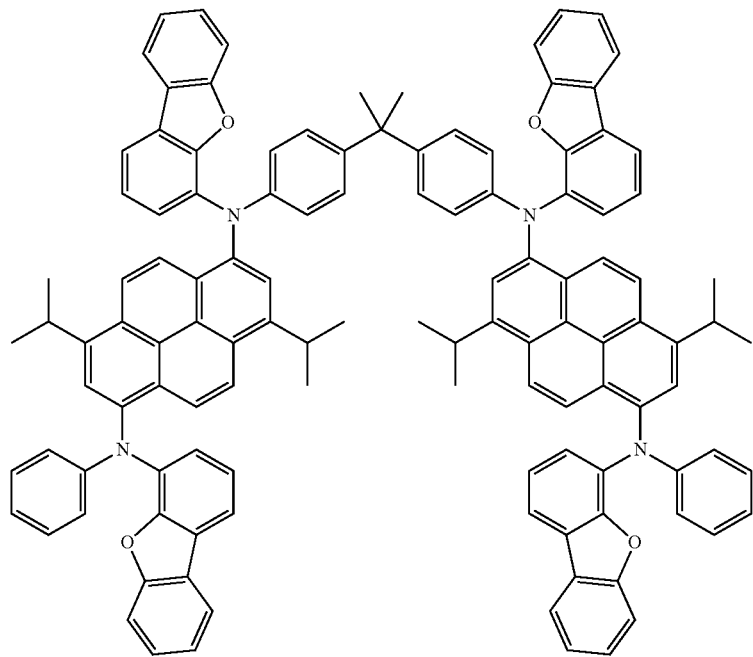
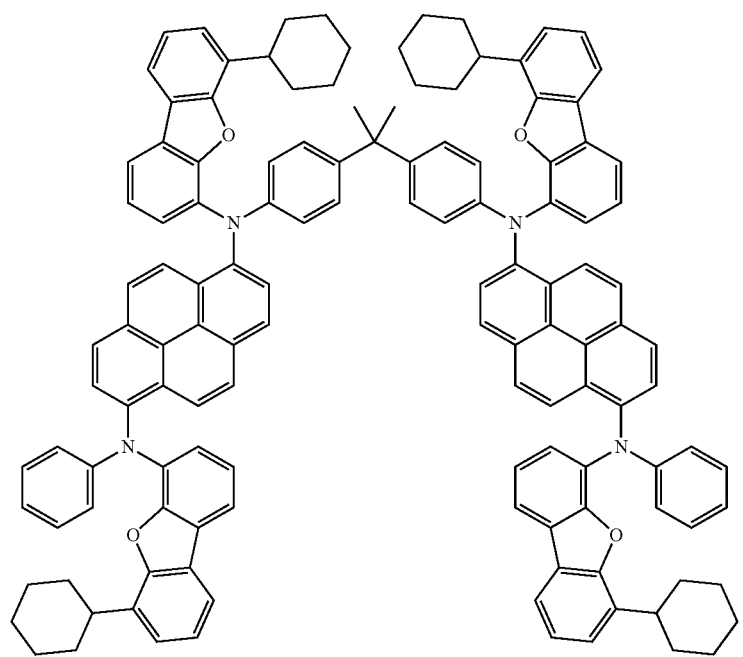

-continued
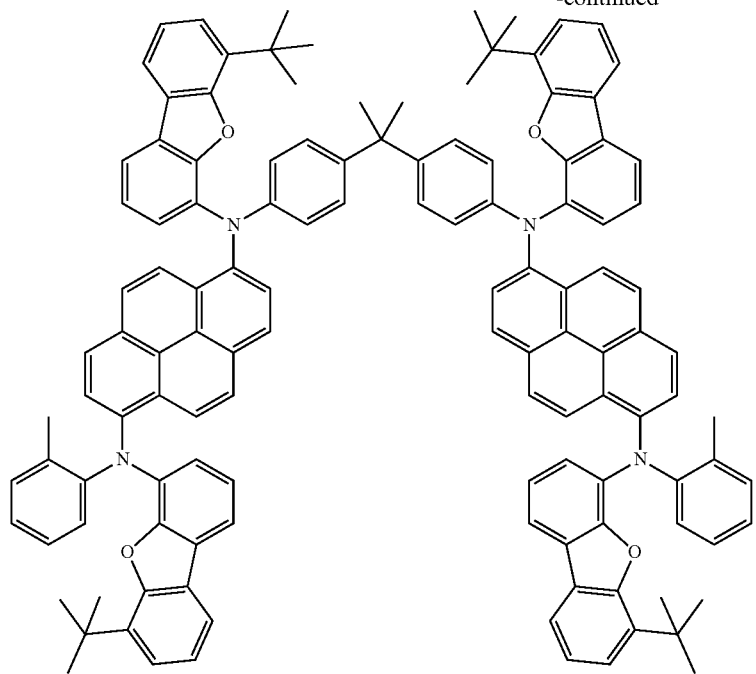
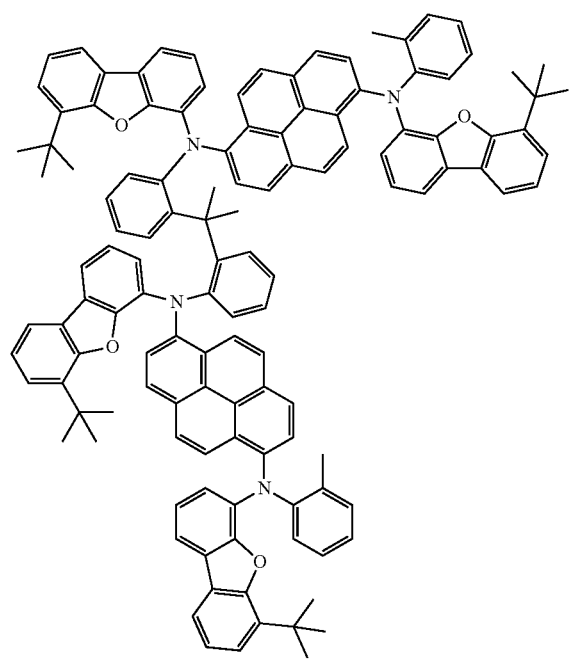

-continued
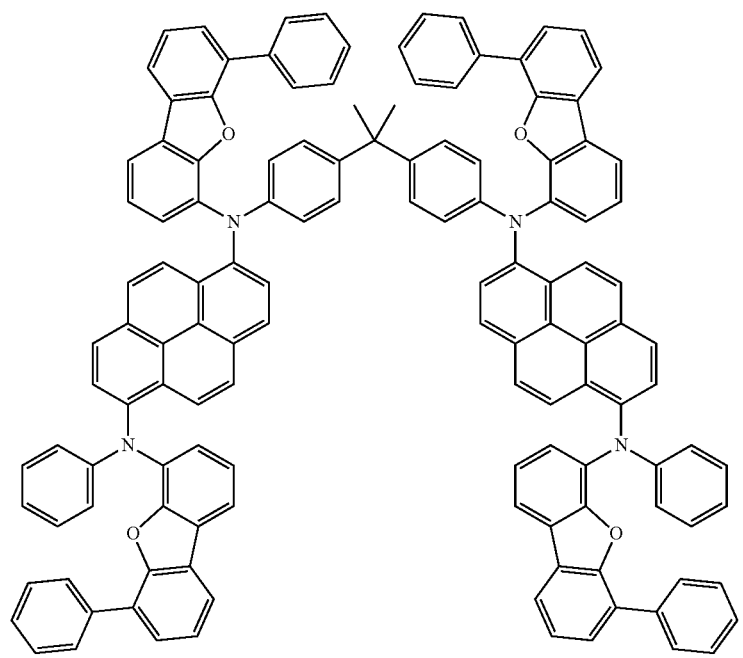
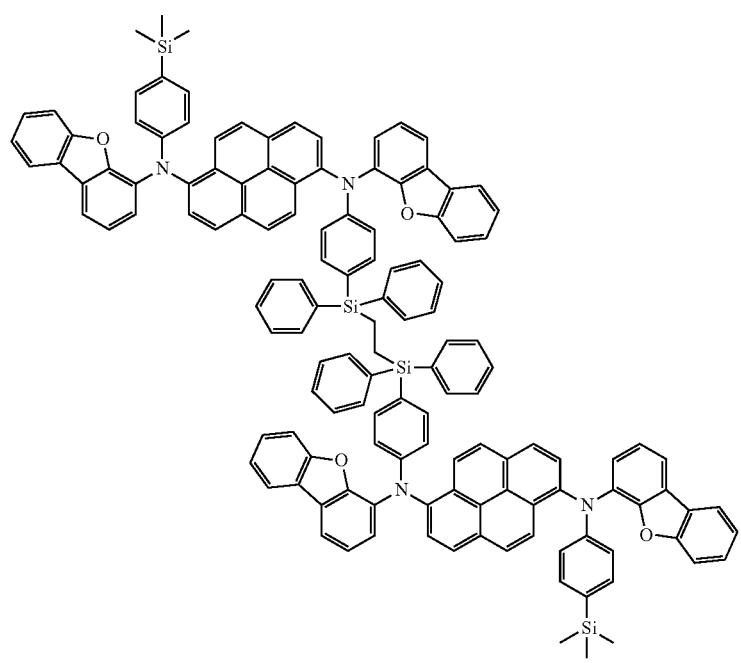

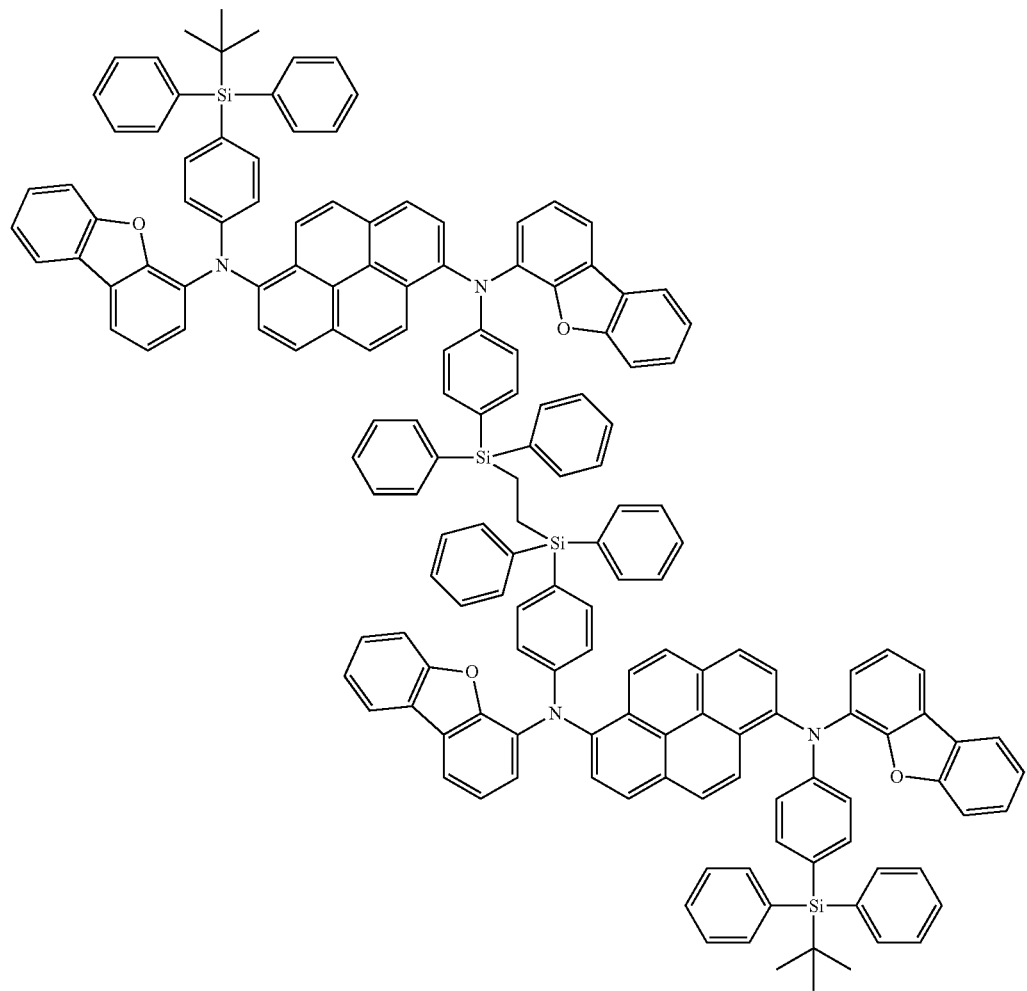

-continued
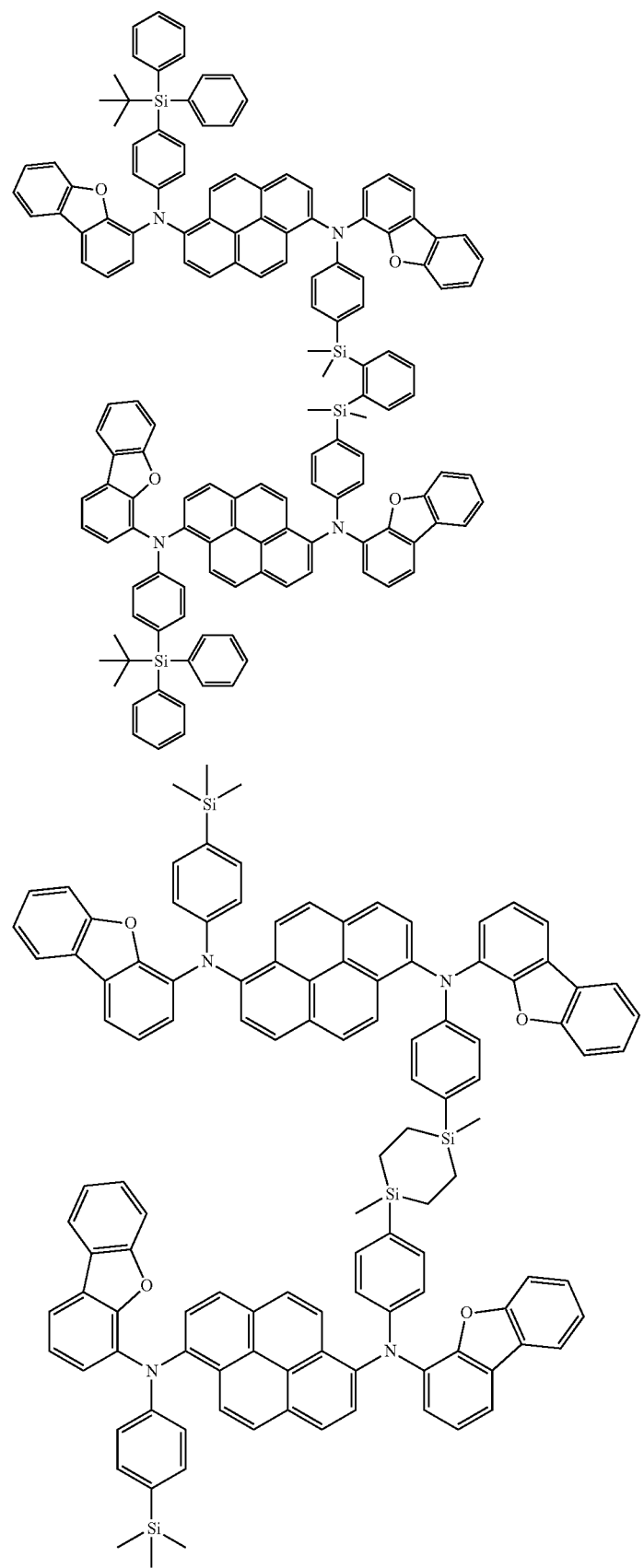

-continued
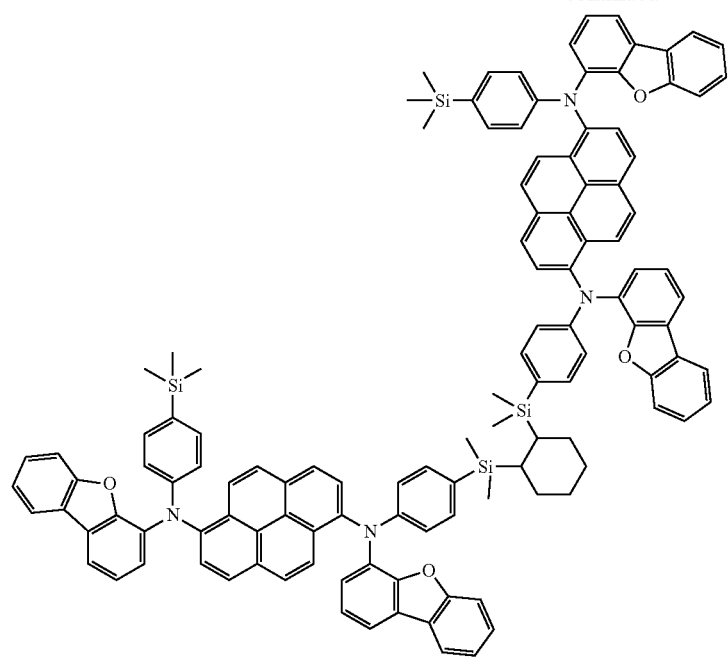
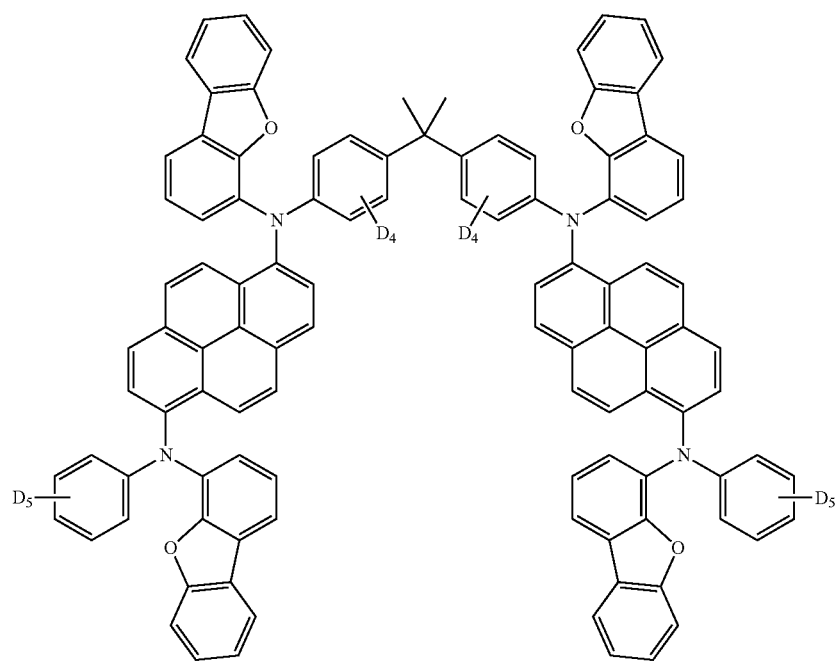

-continued
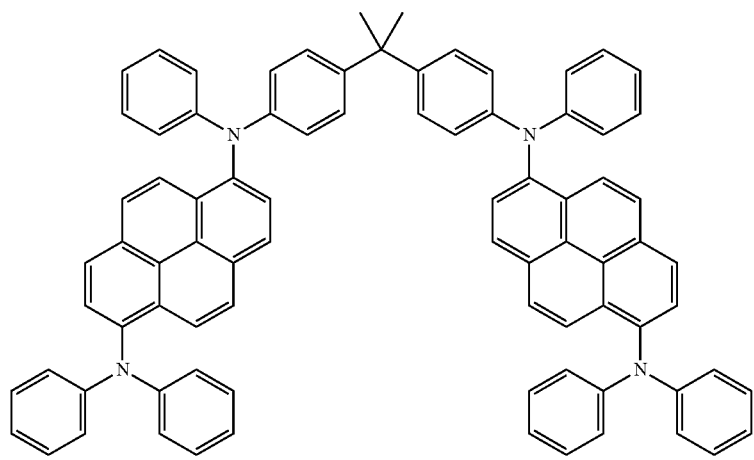
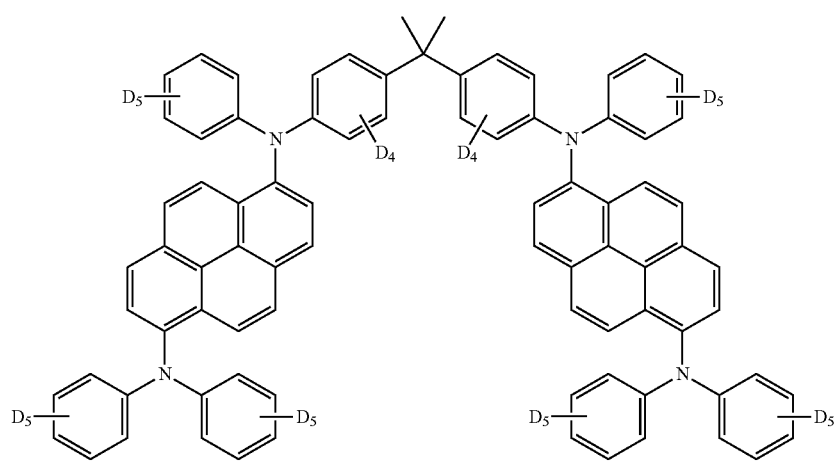
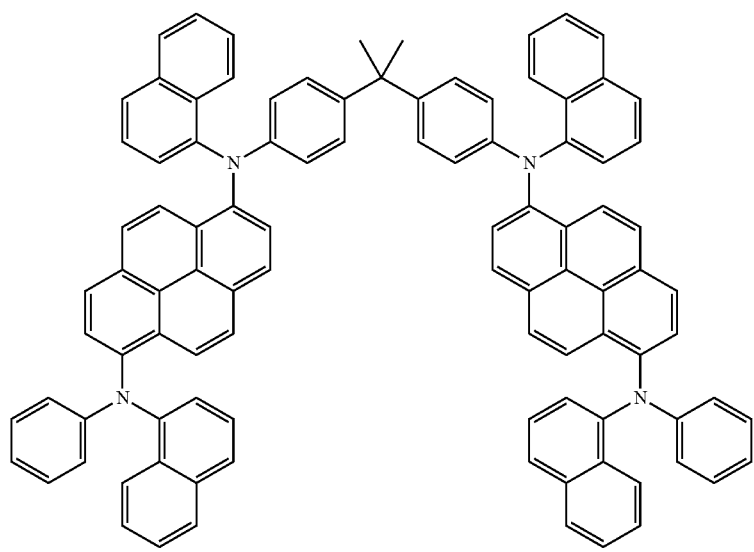

-continued
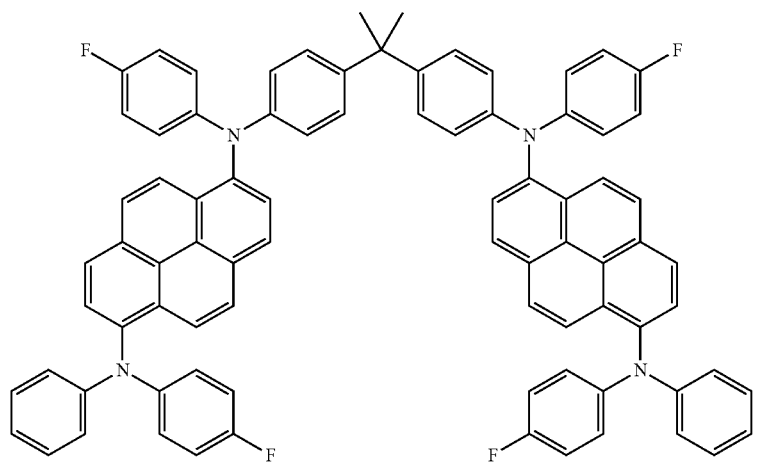
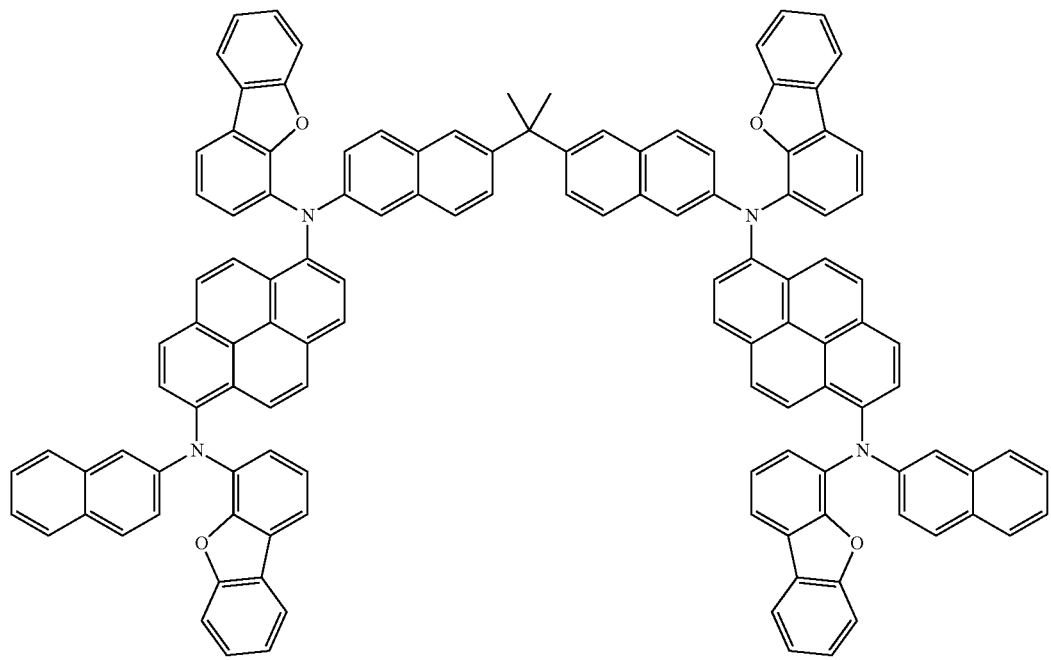

-continued

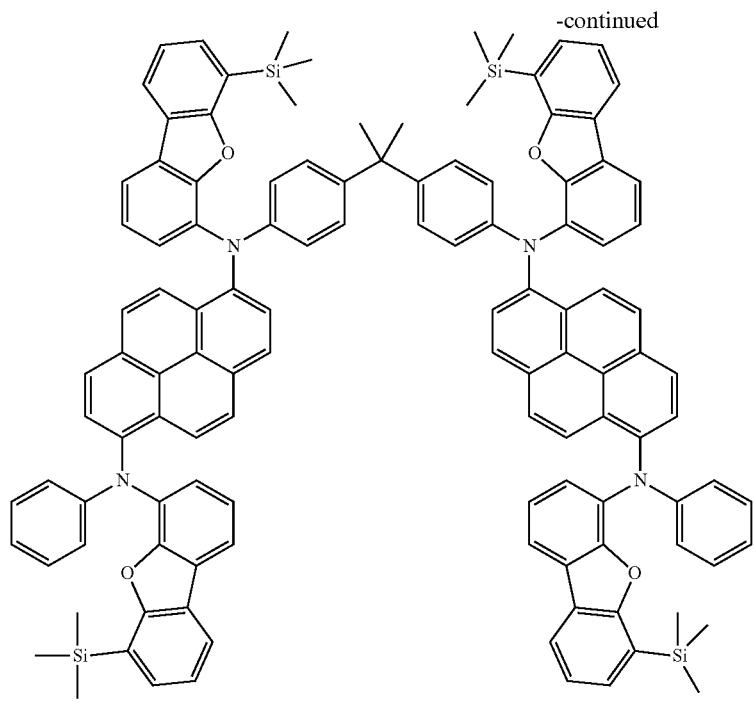

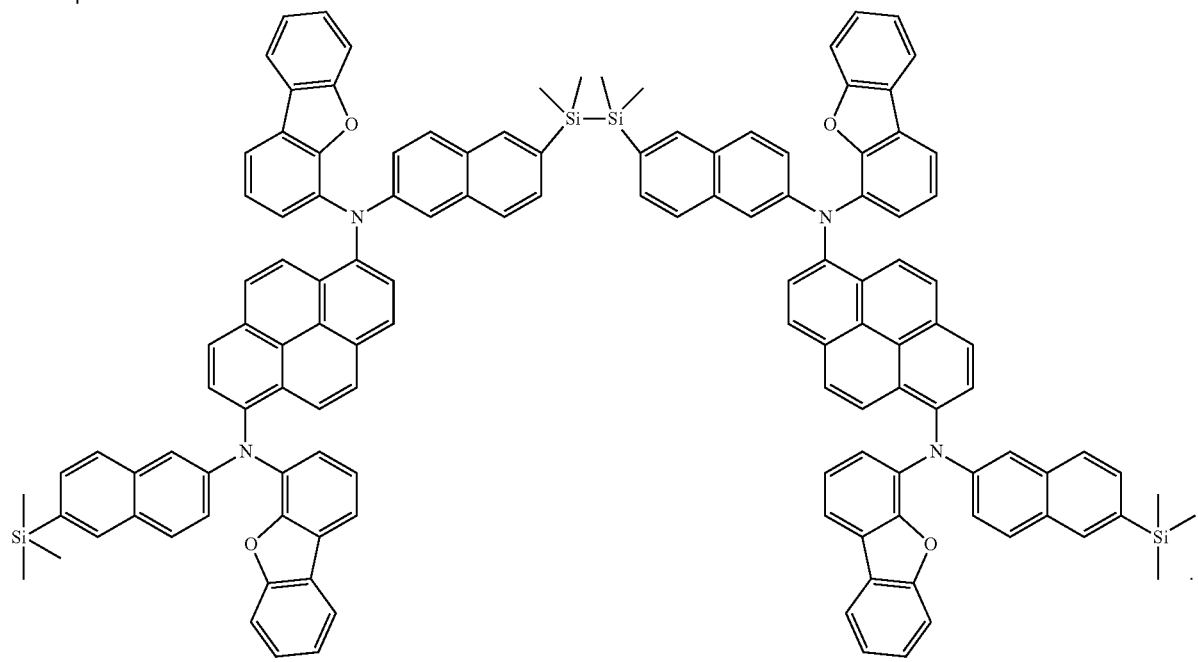

10. A coating composition comprising the compound of claim 1.

11. The coating composition of claim 10, which is for an organic light emitting device.

12. An organic light emitting device comprising:
a first electrode;
a second electrode provided opposite to the first electrode; and
one or more organic material layers provided between the first electrode and the second electrode,
wherein one or more layers of the organic material layers include the coating composition of claim 10.

13. The organic light emitting device of claim 12, wherein the coating composition is heat treated and dried.

14. The organic light emitting device of claim 12, wherein the organic material layer including the coating composition is a hole transfer layer, a hole injection layer, or a layer carrying out hole transfer and hole injection at the same time.

15. The organic light emitting device of claim 12, wherein the organic material layer including the coating composition is a light emitting layer.

16. The organic light emitting device of claim 15, wherein the light emitting layer comprises the compound as a dopant and further comprises a fluorene derivative as a host.

17. The coating composition of claim 10, further comprising a solvent.

18. The coating composition of claim 17, wherein the solvent comprises chlorine-based solvents; ether-based solvents; aliphatic hydrocarbon-based solvents; ketone-based solvents; ester-based solvents; polyalcohols; alcohol-based solvents; sulfoxide-based solvents; amide-based solvents; benzoate-based solvents; and tetraline.

19. The compound of claim 1, wherein L is an alkylene group; or selected from among the following structural formulae:

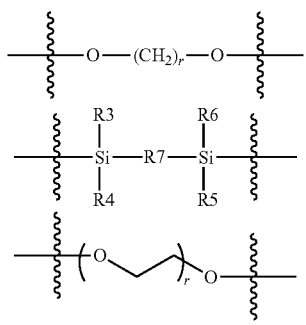

wherein r is an integer of 1 to 5, R7 is a direct bond, an ethylene group, a cyclohexylene group or a phenylene group, R3 to R6 are the same as or different from each other, and each independently a methyl group or a phenyl group.

20. The compound of claim 1, wherein L is selected from among the following structural formulae:

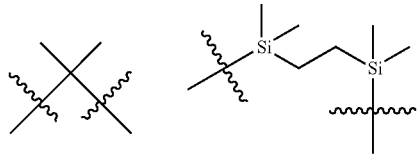

-continued

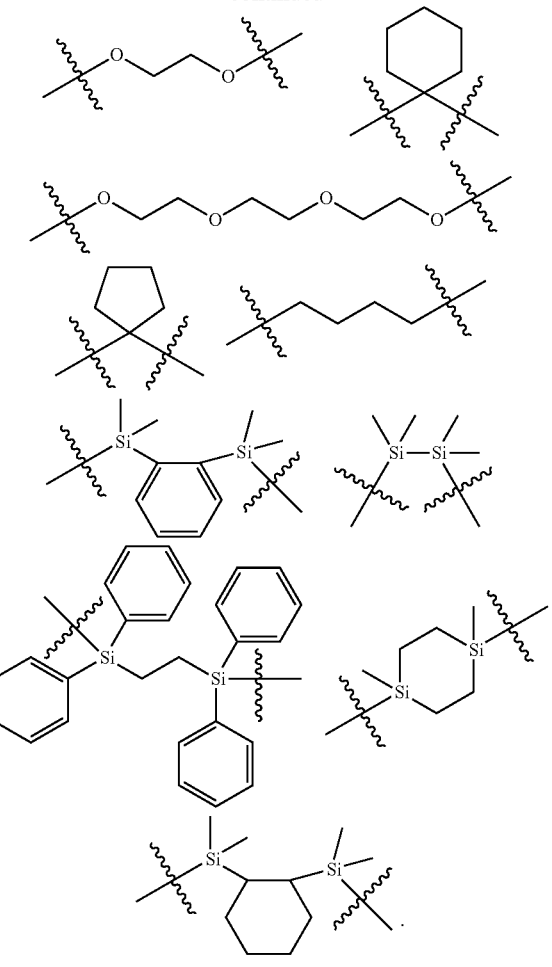

* * * * *